US009796969B2

(12) United States Patent
Kravit et al.

(10) Patent No.: US 9,796,969 B2
(45) Date of Patent: Oct. 24, 2017

(54) ENZYMES THAT CLEAVE NON-GLYCOSIDIC ETHER BONDS BETWEEN LIGNINS OR DERIVATIVES THEREOF AND SACCHARIDES

(71) Applicant: Tethys Research LLC, Bethesda, MD (US)

(72) Inventors: Nancy G. Kravit, Bangor, ME (US); Katherine A. Schmidt, Orono, ME (US)

(73) Assignee: TETHYS RESEARCH LLC, Bethesda, MD (US)

( * ) Notice: Subject to any disclaimer, the term of this patent is extended or adjusted under 35 U.S.C. 154(b) by 149 days.

(21) Appl. No.: 14/747,606

(22) Filed: Jun. 23, 2015

(65) Prior Publication Data

US 2015/0368631 A1    Dec. 24, 2015

Related U.S. Application Data

(60) Provisional application No. 62/050,594, filed on Sep. 15, 2014, provisional application No. 62/016,329, filed on Jun. 24, 2014.

(51) Int. Cl.
*C12N 9/00* (2006.01)
*C12N 9/88* (2006.01)
*C12Q 1/527* (2006.01)
*D21C 5/00* (2006.01)
*C12P 1/00* (2006.01)

(52) U.S. Cl.
CPC .............. *C12N 9/88* (2013.01); *C12P 1/00* (2013.01); *C12Q 1/527* (2013.01); *D21C 5/005* (2013.01); *C12Y 402/02* (2013.01)

(58) Field of Classification Search
CPC .................................... C12N 9/88; C12N 9/00
See application file for complete search history.

(56) References Cited

U.S. PATENT DOCUMENTS

2011/0214199 A1   9/2011  Coffin
2012/0202257 A1   8/2012  Chatterjee et al.

OTHER PUBLICATIONS

Kravit et al., "A novel enzyme that cleaves a phenolic ether bond between C6 of mannose and a monolignol analog", Poster Presenation at 32nd Symposium on Biotechnology for Fuels and Chemicals (2010).
Chang et al., "Synthesis of Fluorogenic Model Compoounds for Bioprospecting of Enzymes that Break Lignin-hemicellulose Bonds", Conference Proceedings from 2012 National Conference: Science for Biomass Feedstock Production and Utilization (2012).
MO BI TEC: Molecular Biotechnology, "Product Information and Instructions: Bacillus Subtilis Expression Vectors" (2005).
UNIPROT, "Nucleotide Sequence for Glycogen operon protein GlgX homolog", (2013).
GENBANK, "Nucleotide Sequence for Burkholderia vietnamiensis G4 chromosome 3", (2014).

*Primary Examiner* — Maryam Monshipouri
(74) *Attorney, Agent, or Firm* — Jeffrey N. Townes; LeClairRyan

(57) ABSTRACT

The patent application relates to isolated polypeptides that specifically cleave non-glycosidic ether bonds between lignins or derivatives thereof and saccharides, and to cDNAs encoding the polypeptides. The patent application also relates to nucleic acid constructs, expression vectors and host cells comprising the cDNAs, as well as methods of producing and using the isolated polypeptides for treating pulp and biomass to increase soluble saccharide yield and enrich lignin fractions.

17 Claims, 15 Drawing Sheets

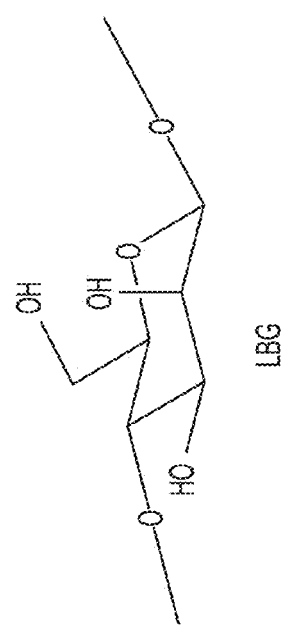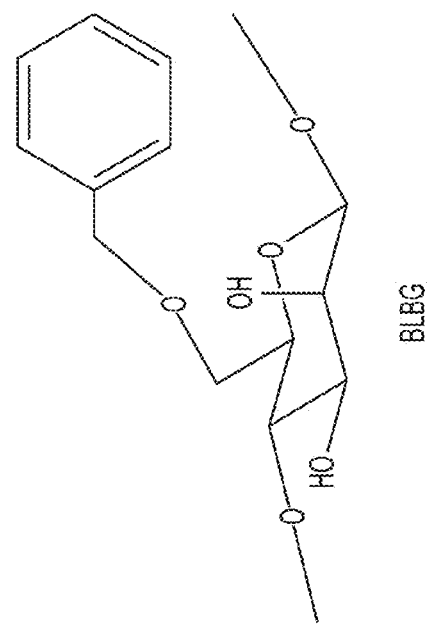
FIG. 3

FIG. 5

```
GTG AAG CGC GCC ATG CTG GCG ACG ATG TTC TCG CAC GGC ACG CCC ATG CTA CTG GGG GGC GAC
 V   K   R   A   M   L   A   T   M   F   S   H   G   T   P   M   L   L   G   G   D

GAG TTC GGC CGT ACG CAA CAG GGC AAC AAT GCC TAT TGC CAG GAC AAC GAA TTG
 E   F   G   R   T   Q   Q   G   N   N   A   Y   C   Q   D   N   E   L

TCA TGG TAC GAC TGG ATG AAG CTC TCG GCC ACG CAG GAG CAG CGA GAG CTT GAC TTC GTC GCG
 S   W   Y   D   W   M   K   L   S   A   T   Q   E   Q   R   E   L   D   F   V   A

CGG CTG GCA CGG TTG CGC GAA CAG CAC CCC ACG TTG ACC CAT TTC CTG CGT GGC GAT AAG
 R   L   A   R   L   R   E   Q   H   P   T   L   T   H   F   L   R   G   D   K

GAG GTC GCG CCC GGT ATG CGC GAA GTG GCA GTT GAC CTT TTC GAC GCG GCG AGT GGC GCC GAG ATG ACC CAG
 E   V   A   P   G   M   R   E   V   A   V   D   L   F   D   A   A   S   G   A   E   M   T   Q

GAA ACC TGG GGT TAT ACA GAG GGG CGG CTG GCC CTT CGT CGT GCC TAC GCC GAG AAG
 E   T   W   G   Y   T   E   G   R   L   A   L   R   R   A   Y   G   E   K

CGC GCC GCC GTC GAC ACC CTC TTG GTC ATC AAC GCC CCC GAG ACC CAT GTC TTC CAT CTG CCG GCA
 R   A   A   V   D   T   L   L   V   I   N   A   P   E   T   H   V   F   H   L   P   A

CCC GCG GCG GTC TGG CGG ATG CGC TGC AGT AGT AAC AGC GCA GCC GAC GCA ATC GAG GTC GCA TGG ACC
 P   A   A   V   W   R   M   R   C   S   S   N   S   A   A   D   A   I   E   V   A   W   T

GAT TCG ACC TTT GCG GTC GAA GGG CGG AGC GTC ATC CTG GGC AGC GTC ATC CTG GGC
 D   S   T   F   A   V   E   G   R   S   V   I   L   G   S   V   I   L   G

GCA TGA
 A  STOP

GCA TGA    (SEQ ID NO:3)
 A  STOP   (SEQ ID NO:4)
```

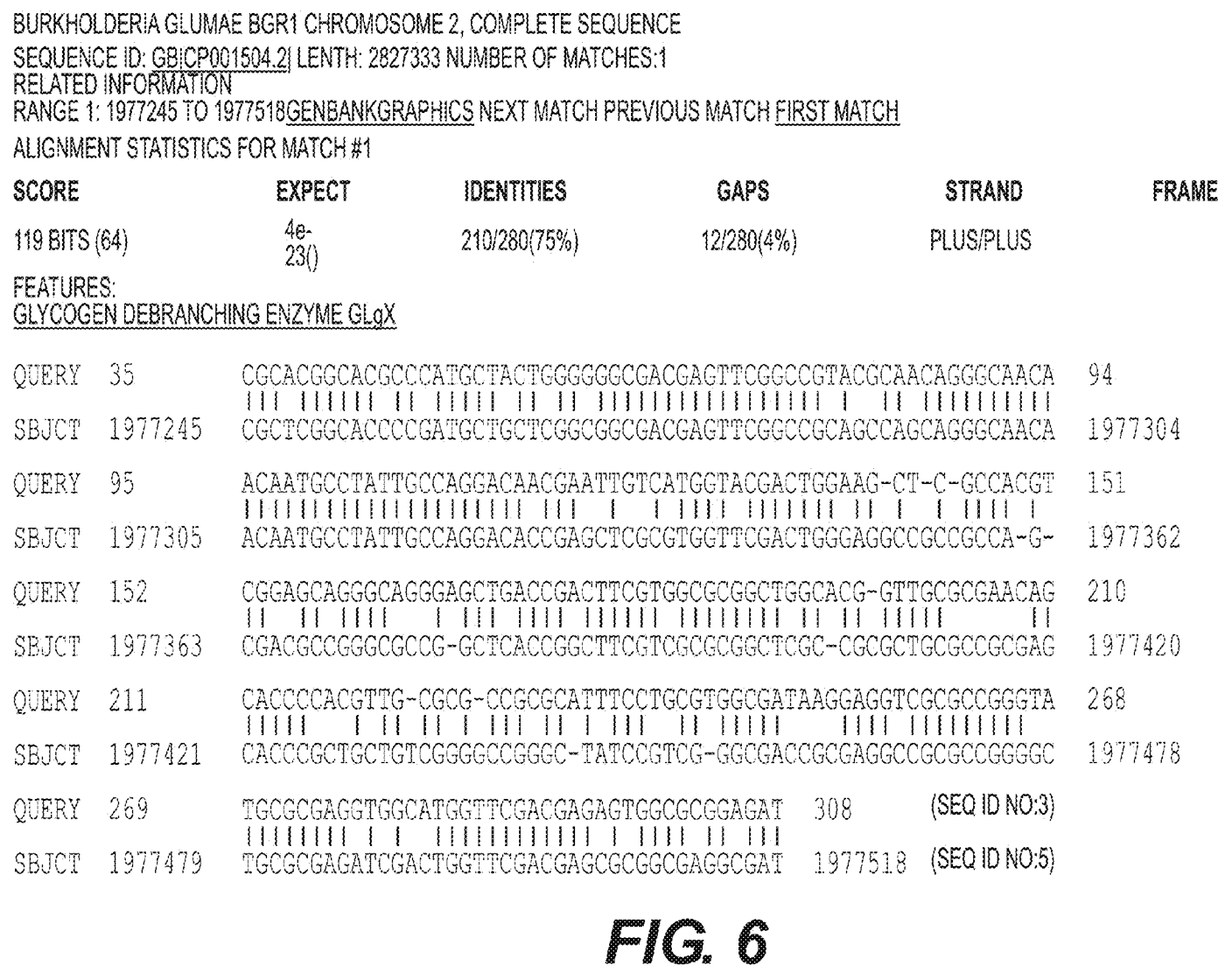

BURKHOLDERIA GLUMAE BGR1 CHROMOSOME 2, COMPLETE SEQUENCE

SEQUENCE ID: GB|CP001504.2| LENTH: 2827333 NUMBER OF MATCHES:1

RELATED INFORMATION

RANGE 1: 1977245 TO 1977518GENBANKGRAPHICS NEXT MATCH PREVIOUS MATCH FIRST MATCH

ALIGNMENT STATISTICS FOR MATCH #1

| SCORE | EXPECT | IDENTITIES | GAPS | STRAND | FRAME |
|---|---|---|---|---|---|
| 119 BITS (64) | 4e-23() | 210/280(75%) | 12/280(4%) | PLUS/PLUS | |

FEATURES:

GLYCOGEN DEBRANCHING ENZYME GLgX

```
QUERY  35       CGCACGGCACGCCCATGCTACTGGGGGGCGACGAGTTCGGCCGTACGCAACAGGGCAACA  94
SBJCT  1977245  CGCTCGGCACCCCGATGCTGCTCGGCGGCGACGAGTTCGGCCGCAGCCAGCAGGGCAACA  1977304

QUERY  95       ACAATGCCTATTGCCAGGACAACGAATTGTCATGGTACGACTGGAAG-CT-C-GCCACGT  151
SBJCT  1977305  ACAATGCCTATTGCCAGGACACCGAGCTCGCGTGGTTCGACTGGGAGGCCGCCGCCA-G-  1977362

QUERY  152      CGGAGCAGGGCAGGGAGCTGACCGACTTCGTGGCGCGGCTGGCACG-GTTGCGCGAACAG  210
SBJCT  1977363  CGACGCCGGGCGCCG-GCTCACCGGCTTCGTCGCGCGGCTCGC-CGCGCTGCGCCGCGAG  1977420

QUERY  211      CACCCCACGTTG-CGCG-CCGCGCATTTCCTGCGTGGCGATAAGGAGGTCGCGCCGGGTA  268
SBJCT  1977421  CACCCGCTGCTGTCGGGGCCGGGC-TATCCGTCG-GGCGACCGCGAGGCCGCGCCGGGGC  1977478

QUERY  269      TGCGCGAGGTGGCATGGTTCGACGAGAGTGGCGCGGAGAT  308      (SEQ ID NO:3)
SBJCT  1977479  TGCGCGAGATCGACTGGTTCGACGAGCGCGGCGAGGCGAT  1977518  (SEQ ID NO:5)
```

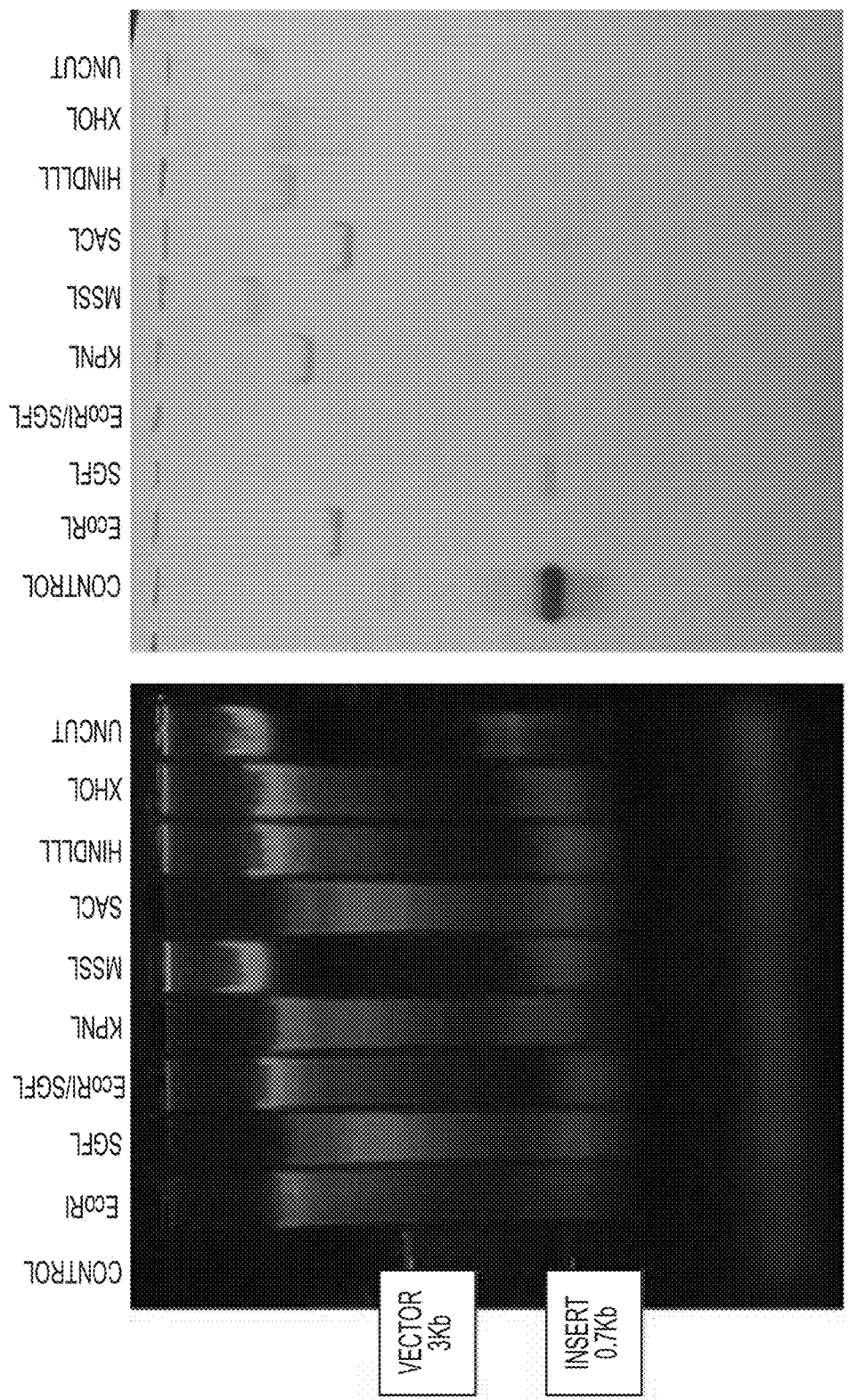

UPSTREAM SEQUENCE (SEQ ID NO:6)

```
TTTCCTGCGTAACCAGGGCGATGCCTGGCGCTGGACGCTGGACTTCCTGCGCCGCAGCTACGACGAGTACAGCCACTCCAAC
GATGACGAGCGCCGTGCGGAAATCGAAGCTGGCTACGATGCGTTCGCCGCCGCGGTGGGTACGCGTCTGGGCGAGCTGCAT
GCGCTGTTGGCGAAGCCGTCGGAGTTTCCGGCGTTCGATCGGAAGCGGCCACGGCGGCCGTGGCGCATGCCTGGCGCGAC
AGCGTTCGTGAGCAGGTGAAGCGCGCGGCGGGTTCGCTCGATCGTGCGACGGAGGTATCCGAAAGCGTCCACCGTGATATCG
AGGCGGTGCACGGACTCATCGGCGCGCTGGACAAGCGCATCGGGGAGCTGTCGAAGGCGGGCGAGGGTGCGTTGCTCACCC
GCACCCATGGCGATTCCATCTGGGTCAGATCCTCGTGGTCCAGGACGATGCCTACATCATCGATTTCGAAGGCGAGCCTGCC
CGCTCGCTGGAAGAACGCCGTGGCAAGCACACGCCACTGCGCGACGTCGCCGGCTTCCTGCGCTCACTGCATTACGCGGCC
GCCATGGCCCGCCGTGGTGAAGACGGCCTGGCACCGGTGGAAGACGAGGGCTTCGGTCAGTACCTGGCCCGATTCCGCGCG
CGCTCGTCGCGGGTTTCCTGGAAGCCTACCGGGCTGTACTGGATGCGGCGCCCGTGCGCTGGGTCAATGCAGGCGACCTCG
TGCCGCTGCTCGAACTTTTCATCATCGAAAAGGCGGCCTACGAGGTCAGCTACGAAGCGGCGAATCGGCCCGGCTGGCTCGA
CGTGCCACTGCGTGGCCTGCTCGATGCCGCCCGCGGCGATACCGCTACCGAACTGAAGGAGGGTACGTGACTGACGCACGTA
GCTACGGACTGAGCGACGCCGCCGCGGTGGCCGCGCTGGTGGAGGGCCGCCACGGCGACCCCTTCGCCCTGCTGGGACCG
CACACGGTCGACGGGCGGCGTGTCGTGCGCACCTTGCAACCCGGTGCGCTCGGTGTCGAACTGATCGACGCGGCAGGCAAG
CCGGTCGCGGAACTGCGGCGCGTCCACGACGGAGGTCTTTTCGCCGGGTGCGCTCCCGACGGCTCCGGGTACCGGCTGCGC
GTTCGCTGGTCCGGGCAAGCCATGACACGCACGATCCTTACAGCTTCGGCACCCTGTTGGCCGACGACGATCTCGCACGGA
TGGCCGAGGGGACGCATGTCGAACTGTTCCGCGTCCTCGGTGCGCATCCATCACCATCGATGGCGTGCACGGCGTACGCTT
CGCTGTCTGGGCACCGAACGCGCAGCGGGTAAGCGCGGTCGGCGACTTCGACAGCTGGGACGGACGCCGTCACCCGATGCG
AAAACGCGTGCCCTCGGGCGTGTGGGAACTGTTCGTTCCCGGCCTGCTCGCCGGCGCACGCTATAAATACGAGATCTGGGGA
GCTGATGGGTCGCTCACGCAACGTGCCGATCCGGTCGCGCTGGCCGCGGAACTGCCGCCGGCCACGGGATCCATCGTGGCC
GACCCGACCGCCTTCCACTGGACGGACGGGGAGTGGCTGCGCAAGCGTGGCGCGCTCCACCACGCCGGGTCGCCCGTTGTCG
ATCTACGAACTGCACGCCGGCTCCTGGCTGCGAGGCAAGGATAACGAAGAGCTGCACTGGGACGACATCGGCGAACGGCTGA
TTCCCTACGTCGCGGGGATGGGCTTCACGCACATCGAACTGCTGCCGATTTCAGAGCACCCGTTCGGTGGTTCGTGGGGGTA
CCAGCCCCTGGGCCAGTTCGCCCCGACATCGCCGTTTCGGTACGCCCGAAGCCTTCGCCCGGTTCGTGGACCGCTGCCATGAA
GCCGGCGTTGGCGTGATCGTCGACTGGGTGCCTGCGCATTTCCCCACCGATATCCACGGCCTGGCGCACTTCGACGGTACGC
CGTTGTACGAGCACGGGGACCCGCGCGAAGGTTTCCATCAGGACTGGAACACCCTGATCTTCAACCTCGGTCGCAACGAGGT
ATCGGCCTTCCTTGTCGCGAGCGCGCTGGCCTGGCTTGAACGTTTCCATGTCGACGGGCTTCGTGTCGATGCGGTCGCGTCG
ATGCTCTATCGCGACTACAGCCGCAAGCATGGCGAGTGGGTACCGAACAAGTACGGTGGCCGCGAGAACCTCGAATCGATCG
ACTTCCTGCGCCGGGTGAACCAGCTCGTTGCCGAACGCCATCCCGATTGCATGACCATTGCCGAGGAATCCACGGCGTGGCC
GGGCGTAACCCAGCCGGTGGAGCAGGGTGGGCTCGGCTTCACCTTCAAGTGGAACATGGGCTGGATGCACGATTCGCTCGAC
TTCATGACGCACGATCCGATCCATCGCCGCTGGCACCACGGCGAGATGACCTTCAGCATGGTTTATGCGTATTCGGAGAAGTT
CGTGCTTCCGCTGTCGCACGACGAAGTGGTGCACGGCAAGCGATCCCTCCTGGGTCGCATGCCTGGCGACGAGTGGCAGAAA
TTCGCCAACCTGCGTGCCTATTACGGCTTCATGTGGGGCACCCAGGCAAGAAGCTGCTGTTCACCGGCGGGAGATCGCCC
AGCCGCGCGAATGGAATCACGACGCGCAGATTGCCTGGAGTTGCTCGATCATCCGCTGCACCTGGCGTGCAGAACTGGTGCG
TGACCTAAACCAGCTCTACGCCGCCACCCCGGCACTCCATGCCTGGGATTCGGATCCCCGCGGGTTTCGCTGGGTCATCGGC
GACGATGCCGAGCAGAGTGTGTTCGCCTGGCTGCGCATGGCCGATGGCGGCCGCACCGTTCTGGTGGTCAGCAACATGACG
CCGACACACGGCATGCCTTCCGCATCGGCGTGCCCGAAGGCGGCCGTTGGCGTGAGGCGCTGAATTCCGACGCGGTCGAGT
ACGGCGGCTCGGGCATCGGCAACGAAGGTGAACGCCATGCCCAGGCGGTGCCTGCACACAGCTTCGCTCAGTCGCTCGTACT
CAGCTTGCCGCCGTTGTCGACGGTCATGTTCATAGCCGACTGACGAGGAAATCG
```

FIG. 8A

MLE GENE (SEQ ID NO:1)

```
ATGCCTGCACTTCCCGAACGCATGCAGTCCGGCACGTCCGGCCGTACCCCTGGGTGCGACCTGTGACGGCATGGGTACCAACTTTG
CCGTCTTCTCCGCCCACGCGGGAGCGGCCATCGAATTGTGCCTGTTCGATCCCTCCGGCAAGCGGGAGATCGCGCCTACGACCT
GCCGAGTGCACCGACGAAACTGGCATGGTTATCTGCCGCGGCGCTCCGGTGTGCACGCTACGGCTTCCGGGCGTACGG
GCCTACGGGCCCGAGGAGGGGCATGCTGCCATGATGGGTCGTCGGTTACCGGGCCATCGTGTCATTGTCGACCGGCACAGTGCCG
GTGCGCTGGTCGGACGGGCCCTGCAGTGGTGTGCTCGACGAGCCCATGCACTGGACCTGGACACGGTTTCACGCGGCACGGCAG
CGGCCATGCCCAAGGCGGTGGTGCTCGACGAGCCCATGCACTGGACCTGGACACGCGCCAACCGGCATACCCCGTGGAACAGAGA
CGATCATCTACGAGACCCTAGTAGTTCGGGGGTTTCACGGGCTAAAGCGAATTGCCAGAACGAGGCGGCACGTTCATTGC
CCTGGCCGATCCGTCTCACCGAGATGAAGCTGCCAATTACTGGGCATGGCCTCAAATCGGGCATCGGCTGAACTCCTGCCCGGCACGCCTTCGTGC
AGGACCGTCGTCACCGAGATACGGCCCGGGTTGCAGGGTTGCATCGCGGGGGGATCGAGGTGATCCTCGACGT
CATGCCCGAAGGAGCGCTCAACGAGATACCGGCCCGGGTTGCAGGGTTGCATGCGGGGGATCGAGGTGATCCTCGACGT
GGTCTACAACGACCACCCTGCGAGGCAGCGAACTGGTACGACGATGTCGTTCCGTGGGCTGACAACGGTCAACACGGTCAACAAAGCTATTACGG
CTCATCCCGGACAATCCGGCTACTGCATCGCCGTACCGACGATACCGGTACCGGCAACACGGTCAACACGGTCCTTCGATCTCGGCGTAAGCCTGGG
AGCTGGTGATGGACTCGCTGCCTACTGGCCCTGCGGCCCTGTTCGACGGCGATGCGCCAGGATCCCGTGCTCGCCAACGTGAAGTTG
ACGTGAGGACCAAGGGTTCGATCCCTGGCCACATCGGCGCCCTGTGGCTGCTATCACATGGGCATGGACTGGGACGCAGCAGGAGCTGCCAAGGCCAGT
ATCTCCAGCCGTGGGACATCCGGAAGTTCGGAAGGGCGATTCGAATATGCGGGGCATCCTTGCCCGGCCCAGGCATCCGGGA
TCCGGACGACGACATCCGTAAGTTCGGAAGGGCGATTCGAATATGCGGGGCATCCTTGCCCGGCCCAGGCATCCGGGA
ACTGTTCGATCACCAGCGGGCGAAAGCCCTGGCCCTCGGGGCGTGAACTTCGTCACCCGCCACGACGGCTTCACGCTGAAGACCTG
GTCAGCTACAACGACAAACAACGACGACAAACAATCGGATGCGGTGAACGCGGCAACGATAACGAGAGCTACAACCACG
GTGTGGAGGGCCGAGCGACGCACCCCATGCTACTCGGGGACGATCGGCCCGTTCGTTCGTATTCCGCGATCGCGTGAAGCGCCATGCGGTGACGATGTTCTT
CTCGACACCGCACGGCACCGCATGCTACTCGGGACCGGGAAGCCTGGGCCGACAGGGCCAACAGGCGCAACAATGCCTATTGCCAGGAC
AACGAATTGTCATGGTACGACCCCAGTTGCGGGCCGCCCAGTTTCCTGCGTGGCCCAGGGGAGCTGACCGACTTCGTGCCCGGCTGGCA
CGGTTGCGGAACAGCCACCCACGTTGCCGCCGCCGAGATGACCCAGGACCTGGGTTATACAACGGAAACCTGGCCGGTATGCGGCAG
GTGGCATGGTTCGACGAGAGTTCGGGGAGAGTGCCCGGGGTCAACTGCTGCGTGCTGATCAACGGCACCGGCCCGCGAGGGCCTGCTTGCCCTGCGT
CGGCCGGCACCCGCGTCAACTGCGCGATCCGCGAGATGCCTGCCTGAACAGTGCGGTCCTGACCGCAACCGGTCGCAATCCGGCCA
CTGCCGGACCCGCGCGTCAACTGCGCGATCCGCGAGATGCCTGCCTGAACAGTGCGGTCCTGACCGCAACCGGTCGCAATCCGGCCA
ACCATTGCCGGTCGAAGGGCGCAGCGGTGATCCTGCCTCGGCCTGCGATTGTCCGGACCGAACCGGCATGA
```

FIG. 8B

DOWNSTREAM SEQUENCE (SEQ ID NO:7)

```
GCGCCCGCTACGTGCGATGCGATGCCTTACGGCGCGGCGGGGGATCGCCTGGGCGATGGCACCACCCGTTTCCGGCTGTGGCACCTG
ATCTGGAAGCGGGTCGTCCGCTCGAGTGCGACACCGGCAGCCACCGGGCACACGGTCGCTCGACGACGGCTGGTTCGAGTCCA
TCTGCCCCCGCCCAGGTGGGCGTGGCCTACCACGGCTTCCCGGATCAACGGTCCTGGCCGTGCCGGATCCCGGTCGCGGGCC
AGCGCGGCGGCGGATGTGCGATGGTTATAGCGTCGTTACCGATCCTCGAGTGGCGCAATACGGCGTGGAAGGGAAG
GCCCTGGCCGGCGAGTCGCGTCATCTACGAGCTCCACGTGGGTGTGCCGATCGCGCCAGTTTCATGGCGTCGAAATGATCCTGCCGCAC
CTGGCGGTCACTTGGCGTCACGGCGATCGAGCTCATGCCGATCGCGCCAGTCTCAAGGCCGTGAGGGTAACTGGGGTTACGATGGCG
TGCTTCCGTACGCACCGGCCGAGCGTTACGGTTGCACACCATTTCGGGGCCGAGATCTCAAGGCCATGATCGACACAGCGACGATCTCGGTCT
GATGGTCTTCCTCGATGTGGTCTACAACCATTTCGGGCCCGATCGGTCTCATCGCCACAGGTGGGCGACTACTTTGTTCACAACGGCTCTAC
GGGAGTGCACACGCCCTGGGGTGCCCTGGATCGGTCTCATCGCCACAGGTGGGCGACTACTTTGTTCACAACGGCTCTAC
TGGATCCAGGAATTCCGCTTCCACGCCGTCGTTTCGACGGTCATGCCATGCCACCTGATCCTCGAGAACGAGGCCAACCAGCCAACCTGCT
CCAGCCGTCCACGCCGTCCGACCGGCGTCGGACCGGATCGCCATGCGACGACTTCCACAATGCGCTGCACGTACTGCTCACGGATGAGGTGAGGGT
CGGTCGCGGTCGCTGCCTTCGACGCCAGTGGAACGGACCAAGCTACTTAGGACGTTGCGGAAGGCTTTGCCTACCAGGCGAACTGATGGG
TATTACGCTCACTACAGGCGCCGATGGACAAGGTCACCTGGGCGCTGGCGCTTGGTGAACTTCCTGCAGAACCACGACCAGGTCG
CTCGGTCGTGTCGGAGCGACCGGAGCGCCCTGCGGCGCCTGCGGTCGATCCCGCAACGATGGAAGCGGCCGTTCTGTATTTCACCGACTTCAGCGATGACG
CAACCGGGCCTTCGGCGGATGCTTTTCATGGGCGGAGGAATGGGCGAGCCGCACGCCGAGCCCGTTCACCAGCTTCCCGAGCCCGAAGAATTCCCGATCCG
AACTTCGTGATCGGTTCGTGACGGTCGTCGGTTCCGATTCCCGAGCCGCGATATCACGAGGCGAGCATCGGCCGCCCGCTATATCCGGACC
AACGAGTACAGCACCTTCACCGGCCATAAATACTGGCGCCCTATATCGACGATGCACGTAGCCTCGGCGCCTGAAGCTCCGGTGAGCCTGCT
TGGTCGCCCTTCGCCATAAATACTGGCGCCCTATATCGACGATGCACGTAGCCTCGGCGCCTGAAGCTCCGGTGAGCCTGCT
TTCAAGGCGTGGTGTTCGCTCGGGCGGTGCTCGGGCGGTCAGTTACCGACCGTGTTCGTCAACCTCGGCAACACCGAGCTGCAGC
CACCATGCCCTCGGCGGTGGCTGGCTCGCGGCGGCGAGTTGCTCACGGGCCGCCGAGATTGCCCTCGTATCCGCCGCCTGCTTCCCGACGCC
GCACCGTTGCCGCGCCTGGAGTCCTGAGCCGTGAACGCCCGTGAACGCGCCCCCCCGAGATTGCCTCGCGCGACGATCGTCTCGCCCGCCAGTCCACACGTTACCCGACAGGGCGGGT
GTACGTGTATTGGCGCGACGCGGCTGGATCGCCTCAGTCGCCCAGTCCACGCCGCCGACGTCCTGCGGCCTT
```

FIG. 8C

>GENE MLE- 3   3077 - 5185   1663   702 aa, chain+
MPALPERMQSGTPYPLGATCDGMGTNFAVFSAHAERIELCLFDPSGKREIARYDLPECTD
ETWHGYLPRVRGGTLYGFRAYGPYEPEEGHRFNPNKLLLDPYARLLHGQVRWSDALHGYR
VSSPRADLSFDRRDSAAAMPKAVVVDEPMHWTGGNRPHTPWNETIYETHLRGFTRTLKR
IRQNERGTFTALADPYVIDYLVKLGITAVELLPVHAFVQDRRLTEMKLRNYWGYNTLAFF
APEPGYMAEGALNEIRAAVQALHAAGIEVTLDVYNHTCEGSELGTTMSFRGLDNKSYYR
LMPDNPRYCINDTGTGNTVNTAHPRVIQLVMDSLRYWVQTFHIDGFREDLGVSLGREDQG
FDFCCGLFDAMRQDPVLANVKLISEPWDIGPGGYQLGNHPPGFAEWNGQFRDDIRKFWKG
DSNMRGILAGRLQASGELFDHQRRKPWASVNFVTAHDGFTLEDLVSYNDKHNDANGEENR
DGGNDNESYNHGVEGPSDDPAVRIPRDRVKRAMLATMFFSHGTPMLLGGDEFGRTQQGNN
NAYCQDNELSWYDWKLATSEQGRELTDFVARLARLREQHPTLRAAHFLRGDKEVAPGMRE
VAWEDESGAEMTQETWGYTEGRLLALRRAQAYGEKRADVTIVLINATPETHVFHLPAPAV
NWRMRCNSAVPDATEVAWTDSTIAVEGRSVILLGSIVRTEPA (SEQ ID NO:2)

*FIG. 9*

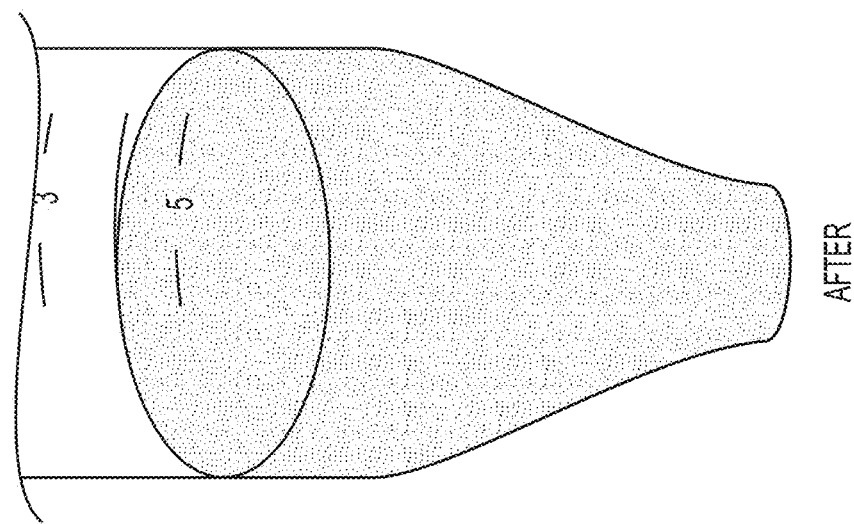
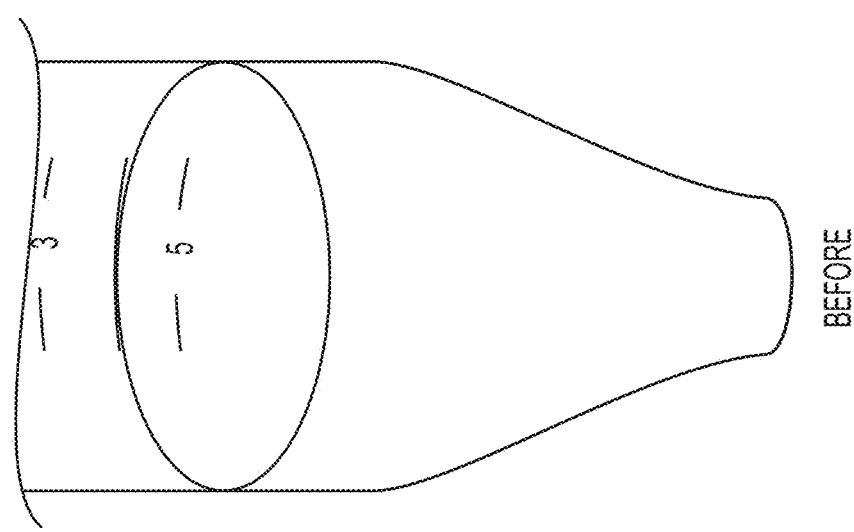
FIG. 10

DNA SEQUENCE OF XLE

ATGCGAAGAAAAGGAAAGATGCTTTGCCTGATGGTGCTGTTCAGTCTTTTGATTGCC
ATGATGCCTGCTAACGTCACGAATGCGGCTCCGACCTGGAATTTGGTATGGAGCGAT
GAATTTAACGGAACTTCTTTGGACAAGTCCAATTGGAAAGCGGAAATCGGAACCGG
CAGCGGCGGGTGGGGCAACAACGAGCTTCAGTATTACACGGACCGCCCGGAGAATG
TCCAGGTGACGGGTGGAAATCTGGTCATTACCGCTCGCAAAGAAGCCTACGGCGGG
ATGAATTACACGTCGGCACGGATTAAAACGCAAGGGCTGCGCAGCTTTACGTACGG
AAAGATCGAAGCGCGTATCAAGCTGCCGTCGGGACAAGGATTATGGCCGGCTTTTT
GGATGCTGGGAACGAACATCGATTCCGTCGGATGGCCCAAGAGCGGAGAAACGGAC
ATTATGGAGCGGGTCAACAACAATCCTTACGTAAACGGTACCGTGCACTGGGATGC
CAATGGCCAAGCCGATTATGGGCAGGTATCCGGAAATCTTGATTTTACCCAATATCA
TGTATATAGCGTTGAATGGGATTCCAAGTATATTAAATGGTTCGTCGACGGCCAGCA
GTATAACGCATTCTACATCGAAAACGGTACAGGTAACACGGAGGAATTCCAACTGC
CGTTCTTCCTGCTGCTGAATCTGGCGGTCGGTGGCAATTGGCCGGGTAGCCCGAATA
ATTCTACGCAGTTCCCTGCCCAAATGCTGGTCGATTACGTACGGGTATATCAGAGCT
CTGATGCGCCCAATATTGTGAGCGGCGGCATTTACACGATCGGGAACAAGGCCAGC
GGCAAAGTCATGGATGTGGTCGATGTATCGACGGCCAGCGGAGCGAAGATTCAGCA
GTGGACCAACTACAGCGCCAATAACCAAAGATTCAAGATCGAAAGCACCGGAGACG
GCTTCTATAAGCTCACGGCCGTGCACAGCGGGAAGGTACTGGACGTGCCGAATTCTT
CGACAGCGACCGGCGTTCAGCTGCAGCAATGGGACGACAACGGGACGAATGCGCA
GCGGTGGAGCACCGTGGATGTCGGAGGCGGATATTACAAACTGGTATCCAAAGTGA
GCGGACTGGTCGCCGACTTATCGGGATCTTCCAGCGCTGACGGGGCCGTGGTCCAGC
AGTGGAGCGACAACGGTACCGATGCCCAGAAGTGGTCGTTTACGAAAGTGAATTAA (SEQ ID NO: 49)

FIG. 12

AMINO ACID SEQUENCE OF XLE

MRRKGKMLCLMVLFSLLIAMMPANVTNAAPTWNLVWSDEFNGTSLDKSNWKAEIGTG
SGGWGNNELQYYTDRPENVQVTGGNLVITARKEAYGGMNYTSARIKTQGLRSFTYGKI
EARIKLPSGQGLWPAFWMLGTNIDSVGWPKSGETDIMERVNNNPYVNGTVHWDANGQ
ADYGQVSGNLDFTQYHVYSVEWDSKYIKWFVDGQQYNAFYIENGTGNTEEFQLPFFLL
LNLAVGGNWPGSPNNSTQFPAQMIVDYVRVQSSDAPNIVSGGIYTIGNKASGKVMDV
VDVSTASGAKIQQWTNYSANNQRFKIESTGDGFYKLTAVHSGKVLDVPNSSTATGVQL
QQWDDNGTNAQRWSTVDVGGGYYKLVSKVSGIVADLSGSSSADGAVVQQWSDNGT
DAQKWSFTKVN (SEQ ID NO: 50)

*FIG. 13*

ENZYMES THAT CLEAVE NON-GLYCOSIDIC ETHER BONDS BETWEEN LIGNINS OR DERIVATIVES THEREOF AND SACCHARIDES

CROSS-REFERENCE TO RELATED APPLICATIONS

This application claims the benefit of priority of U.S. Provisional Patent Application Ser. No. 62/050,594, filed Sep. 15, 2014, and U.S. Provisional Patent Application Ser. No. 62/016,329, filed Jun. 24, 2014; which are hereby incorporated by reference in their entirety.

GOVERNMENT SUPPORT

This invention was made with government support under National Science Foundation Grants 1046844 and 1315023, Department of Energy Grant DE-FG02-07ER84788, Maine Technology Institute Grants SG1537, SG1793, SG3446, DA708 and DA1613 and two Department of Transportation Sun Grant Initiative Awards. The government has certain rights in the invention.

REFERENCE TO A SEQUENCE LISTING

This application contains a Sequence Listing, named "39858.0202_ST25.txt" and having a size of 33,302 bytes and created Jun. 23, 2015, is incorporated herein by reference.

FIELD OF THE INVENTION

The patent application relates to isolated polypeptides that specifically cleave a non-glycosidic ether bond between a lignin or a derivative thereof and a saccharide, and cDNAs encoding the polypeptides. The patent application also relates to nucleic acid constructs, expression vectors and host cells comprising the cDNAs as well as methods of producing and using the isolated polypeptides for treating pulp and biomass to increase soluble saccharide content and enrich lignin content.

BACKGROUND OF THE INVENTION

Today, the United States imports vast amounts of petroleum to help satisfy its energy requirements. Volatile pricing, supply limitations, greenhouse gas emissions and the political and military costs associated with fossil fuels have all led to renewed interest in energy alternatives. But in addition to its use for fuel, many important basic chemical commodities are produced from oil. In fact, approximately 5% of the total output of a petroleum refinery is used by the chemical processing industry as raw materials (See Ragauskas, A. J. et al., The path forward for biofuels and biomaterials, Science 311:484-489 (2006), which is hereby incorporated by reference in its entirety) and as the cost of oil rises, so too does the cost of downstream commodity chemicals like plastic resins.

Fortunately, biomass can be a substitute feedstock for the production of fuel as well as many of the building block chemicals that are currently produced from oil. Because petroleum and biomass are both carbon-based, chemicals (including relatively linear polymers and polymer building blocks) that are based on non-renewable petroleum products can also be produced from renewable biomass using current fermentation techniques.

Unfortunately, the use of agricultural crops as a source of biomass for chemicals and energy suffers from at least two disadvantages. First, raising crops is oil intensive. Farm equipment needs fuel to weed, till and harvest. Moreover, fertilizers and pesticides are often produced from petroleum. Second, crops and land are needed to feed both humans and domestic animals, and their use to produce an industrial feedstock escalates competition between the use of land for food or for fuel. The United Nations Food & Agricultural Organization (FAO) reports that the average price of corn increased 85% between the years of 2000 and 2007 as a direct result of rising farm energy costs and increased demand from ethanol and bioplastics producers. In fact, in 2007 about 25% of the US corn crop was diverted into ethanol production and the rate is accelerating. See ICIS Chemical Business, Biofuels backlash grows in fuel versus food debate, Simon Robinson, London, Feb. 11, 2008, which is hereby incorporated by reference in its entirety.

A better alternative to the use of agricultural biomass is selective tree cutting, which is sustainable and requires little cultivation. Due to vertical tree growth, it produces a much greater yield of biomass per acre. In a recent report, the Pacific Northwest National Laboratory (PNNL) and the National Renewable Energy Laboratory (NREL) summarized the results of an extensive screening study of the possibilities for processing the sugars derived from woody biomass into basic chemicals. See Werpy, T. and Peterson, G., Top value added chemicals from biomass, Volume I, Results of screening for potential candidates from sugars and synthesis gas, produced for the NREL, Publication No. DOE/GO-102004-1992, August 2004, which is hereby incorporated by reference in its entirety. Among the 300 possible products listed were the top 30 building block chemicals of industry. Of particular interest are itaconic acid and lactic acid, the bifunctional organic acids derived from fermentation that can be made into a wide variety of plastic products.

North American forests contain huge amounts of woody biomass and the cost per ton of raw material is significantly less than for agricultural biomass. However, the drawback to using wood for chemical production and biofuels has been, and continues to be, the difficulty and inefficiency of fractionating wood into its three basic components, namely, cellulose, hemicellulose and lignin. Effective separation would allow the hemicellulose (a branched and relatively short chain of simple sugars) to be utilized for fermentation into chemical products, instead of being burned as waste. It is estimated that 60-80% of the cost of manufacturing chemical products from agricultural biomass is incurred in separating fermentable sugars from the starting material. See Ragauskas, A. J. et al., 2006, supra. For forest biomass, with complex linkages between its three components, this percentage is likely larger. Therefore, decreasing the cost and increasing the efficiency of separation will have a substantial effect on the economic feasibility of using forest biomass for chemical and biofuel production.

The first step toward cost-effective use of forest biomass has been the conceptualization of the integrated forest biorefinery (IFBR) co-located with pulp and paper mills. In such a system, value is maximized by diverting high-value cellulose to papermaking, in effect subsidizing the separation cost. The lignin and hemicellulose can then be made available for further processing instead of being burned for energy, as is currently the case. At present, IFBRs are targeting hardwood as a raw material. This is because softwoods are more extensively cross-linked, making it harder to extract their hemicellulose. However, the predominant softwood hemicellulose (mannan) is made of more easily fermentable sugars. A cost-effective method of extracting mannan and xylan from softwoods and hardwoods would yield superior hemicellulose feedstreams.

Therefore, there is a need to develop innovative, efficient, cost-effective and non-damaging procedures for fractionating woody biomass (e.g. hardwoods and softwoods) for chemical and fuel production. There is also a need to develop methods for separating woody biomass into hemicellulose, cellulose and lignin components that are clean and gentle and at conditions that maintain the functionality and downstream use of each of these components. This invention answers those needs.

SUMMARY OF THE INVENTION

This invention relates to complementary DNA (cDNA) molecules that encode isolated polypeptides that specifically cleave non-glycosidic ether bonds between lignins or derivatives thereof and saccharides. The cleavage of non-glycosidic ether bonds can be between aromatic or non-aromatic carbons of the lignins or derivatives thereof and the saccharides.

Examples of the saccharides may include monosaccharides, disaccharides, oligosaccharides, and polysaccharides. Hemicellulose is an example of a polysaccharide.

The isolated polypeptides may include the amino acid sequence of SEQ ID NO:2 and SEQ ID NO:4, which correspond to the sequences derived from the genomic clone and non-genomic clone (see catalytic fragment as shown in FIG. 5), respectively. The isolated polypeptides have at least about 80% or at least about 90-95% sequence identity to the amino acid sequence of SEQ ID NO:2 or SEQ ID NO:4. Alternatively, the amino acid sequences of the isolated polypeptides can have at least about 96%, at least about 97%, at least about 98% or at least about 99% sequence identity to the amino acid sequence of SEQ ID NO:2 or SEQ ID NO: 4.

The isolated polypeptides may also include the amino acid sequence of SEQ ID NO:50, which correspond to the sequence derived from the genomic clone of XLE. The isolated polypeptides have at least about 80%, at least about 85%, or at least about 90-95% sequence identity to the amino acid sequence of SEQ ID NO:50. Alternatively, the amino acid sequences of the isolated polypeptides can have at least about 96%, at least about 97%, at least about 98% or at least about 99% sequence identity to the amino acid sequence of SEQ ID NO:50.

The isolated polypeptides can specifically cleave a non-glycosidic ether bond between a lignin or a derivative thereof and a saccharide. The saccharide can be a monosaccharide, a disaccharide, an oligosaccharide or a polysaccharide. The polysaccharide can be a hemicellulose. The isolated polypeptides are encoded by their respective cDNAs, namely SEQ ID NOS. 1 and 3, respectively. The isolated polypeptides may include (a) a polypeptide having at least about 80% sequence identity to the mature polypeptide of SEQ ID NO:2; (b) a polypeptide having at least about 90-95% sequence identity to the mature polypeptide of SEQ ID NO:2; (c) a polypeptide encoded by a polynucleotide that hybridizes under medium to high stringency conditions with (i) the mature polypeptide coding sequence of SEQ ID NO:1 or (ii) the full length complement of (i); (d) a polypeptide encoded by a polynucleotide having at least about 80% sequence identity to the mature polypeptide coding sequence of SEQ ID NO:1; (e) a polypeptide encoded by a polynucleotide having at least about 90-95% sequence identity to the mature polypeptide coding sequence of SEQ ID NO:1; (f) a variant of the mature polypeptide of SEQ ID NO:2 comprising a substitution, deletion and/or insertion at one or several positions; and (g) a fragment of the polypeptide of (a), (b), (c) (d) or (e) that specifically cleaves a non-glycosidic ether bond between a lignin or a derivative thereof and a saccharide.

Alternatively, the isolated polypeptide is encoded by its cDNA, e.g., SEQ ID NO 49. The isolated polypeptide may include: (a) a polypeptide having at least about 80%, or at least about 85% sequence identity to the mature polypeptide of SEQ ID NO:50; (b) a polypeptide having at least about 90-95% sequence identity to the mature polypeptide of SEQ ID NO:50; (c) a polypeptide encoded by a polynucleotide that hybridizes under medium to high stringency conditions with (i) the mature polypeptide coding sequence of SEQ ID NO:49 or (ii) the full length complement of (i); (d) a polypeptide encoded by a polynucleotide having at least about 80%, or at least about 85% sequence identity to the mature polypeptide coding sequence of SEQ ID NO:49; (e) a polypeptide encoded by a polynucleotide having at least about 90-95% sequence identity to the mature polypeptide coding sequence of SEQ ID NO:49; (f) a variant of the mature polypeptide of SEQ ID NO:50 comprising a substitution, deletion and/or insertion at one or several positions; and (g) a fragment of the polypeptide of (a), (b), (c) (d) or (e) that specifically cleaves a non-glycosidic ether bond between a lignin or a derivative thereof and a saccharide.

The isolated polypeptide may also include (a) a catalytic domain having at least about 80% sequence identity to the amino acids of SEQ ID NO:4; (b) a catalytic domain having at least about 90-95% sequence identity to the amino acids of SEQ ID NO:4; (c) a catalytic domain encoded by a polynucleotide that hybridizes under medium to high stringency conditions with (i) the nucleotide sequence of SEQ ID NO:3 or (ii) the full length complement of (i); (d) a catalytic domain encoded by a polynucleotide having at least about 80% sequence identity to the nucleotide sequence of SEQ ID NO:3; and (e) a catalytic domain encoded by a polynucleotide having at least about 90-95% sequence identity to the nucleotide sequence of SEQ ID NO:3.

The isolated polypeptides may be a mannan:lignin etherase or xylan:lignin etherase. The isolated polypeptide may cleave (a) the non-glycosidic ether bond between an aromatic carbon of the lignin or the derivative thereof and the saccharide or (b) the non-glycosidic ether bond between a non-aromatic carbon of the lignin or the derivative thereof and the polysaccharide. Examples of non-aromatic carbons of the lignin may include α-linked benzyl carbon or β-linked benzyl carbon.

Also disclosed herein is a method of treating a pulp or biomass containing cross-linked lignin-saccharide complexes, which comprises contacting the pulp or biomass with the isolated polypeptide for a sufficient amount of time to allow the polypeptide to break at least some of the non-glycosidic ether bonds between lignin-saccharide complexes, thereby causing the lignins and saccharides to be released from the lignin-saccharide complexes in the pulp or biomass without significant concomitant degradation of the isolated lignins and saccharides. The method for pulp or biomass treatment may further comprise co-incubating concurrently or sequentially the pulp or biomass with a hemicellulase such that intact hemicellulose is not removed from the pulp or biomass. Examples of saccharides as used herein are monosaccharides, disaccharides, oligosaccharides and polysaccharides. An example of a polysaccharide is hemicellulose.

The method for pulp or biomass treatment involves cleavage of the non-glycosidic ether bond between an aromatic or non-aromatic carbon of the lignin or the derivative thereof and the saccharide. Examples of non-aromatic carbons of the lignin are α-linked benzyl carbon and β-linked benzyl carbon.

Another method relates to the identification of an enzyme that specifically cleaves a non-glycosidic ether bond between a lignin and a saccharide. The method encompasses (a) providing a fluorogenic lignin analog that is capable of forming a non-glycosidic ether bond with the saccharide; (b) derivatizing the fluorescent lignin analog onto the saccharide via the non-glycosidic ether bond, wherein the formation of the non-glycosidic ether bond changes the fluorescent property of the lignin analog; and (c) contacting an enzyme with the lignin analog-derivatized saccharide, wherein a change in the fluorescent property of the lignin analog after contacting indicates that the enzyme specifically cleaves the non-glycosidic ether bond between the lignin-analog and the saccharide. An example of a fluorogenic lignin analog is 4-methylumbelliferyl acetate (4-MU). The saccharides can be monosaccharides, disaccharides, oligosaccharides and polysaccharides. An example of a polysaccharide is hemicellulose.

Also described herein are nucleic acid constructs or expression vectors that include the cDNA molecules encoding the isolated polypeptides of the application, wherein the cDNA molecules are operably linked to one or more control sequences that direct the expression of the polypeptides in the expression hosts. Examples of the nucleic acid constructs or expression vectors are selected from the group consisting of pHIS525-cMLE, pHIS525-cfMLE, pAES40-cMLE, pAES40-cfMLE, pHT43-cMLE, pHT43-cfMLE, pBluescript SK⁻-cMLE, pBluescript SK⁻-cfMLE, pFN6A-cMLE and pFN6A-cfMLE.

Transformed host cells can include the expression vectors that comprise the cDNA molecules of the application. Examples of the transformed host cells described in the application are *B. megaterium* (pHIS525-cMLE), *B. subtilis* (pHIS525-cMLE), *B. megaterium* (pHIS525-cfMLE), *B. subtilis* (pHIS525-cfMLE), *E. coli* (pAES40-cMLE), *E. coli* (pAES40-cfMLE), *B. subtilis* (pHT43-cMLE), *B. subtilis* (pHT43-cfMLE), *E. coli* (pBluescript cMLE), *E. coli* (pBluescript SK⁻-cfMLE), *E. coli* (pFN6A-cMLE) and *E. coli* (pFN6A-cfMLE).

Another feature of the invention is a method of producing heterologous polypeptides that specifically cleave non-glycosidic ether bonds between lignins or derivatives thereof and saccharides. The method involves (a) cultivating the transformed host cells containing the expression vectors that comprise the cDNA molecules under conditions conducive for the production of the heterologous polypeptides; and (b) recovering the heterologous polypeptides.

Additional aspects, advantages and features of the invention are set forth in this specification, and in part will become apparent to those skilled in the art on examination of the following, or may learned by practice of the invention. The inventions disclosed in this application are not limited to any particular set of or combination of aspects, advantages and features. It is contemplated that various combinations of the stated aspects, advantages and features make up the inventions disclosed in this application.

BRIEF DESCRIPTION OF THE DRAWINGS

FIG. 3 shows the synthesis of benzylated locust bean gum (BLBG).

FIG. 5 shows the nucleotide and translated amino acid sequences (SEQ ID NOS:3 and 4, respectively) of mannan:lignin etherase (MLE)-ORF (open reading frame).

FIG. 6 shows the alignment of cDNA open reading frame of mannan:lignin etherase (SEQ ID NO:3) to a glycogen debranching enzyme from *Burkholderia glumae* BGR1 (SEQ ID NO:5).

FIGS. 7A-7B show a Southern analysis of putative etherase (MLE) cDNA. FIG. 7A shows ethidium bromide stained gel before transfer. FIG. 7B shows southern blot probed with biotinylated probe to cDNA from clone 17-2.

FIGS. 8A-8C show a predicted gene sequence for the mannan:lignin etherase (MLE) gene (FIG. 8B; SEQ ID NO:1) and its surrounding regions (an upstream sequence (FIG. 8A; SEQ ID NO:6) and a downstream sequence (FIG. 8C; SEQ ID NO:7)) identified using—gene prediction software (FGENES) from Softberry, Inc.

FIG. 9 shows the deduced amino acid sequence for mannan:lignin etherase (MLE; SEQ ID NO:2).

FIG. 10 shows a concentrated culture supernatant before and after incubation with softwood kraft pulp.

FIG. 12 shows the DNA sequence (SEQ ID NO: 49) of xylan:lignin etherase (XLE).

FIG. 13 shows the translated amino acid sequence (SEQ ID NO: 50) of xylan:lignin etherase (XLE).

DETAILED DESCRIPTION OF THE INVENTION

Figure 1:
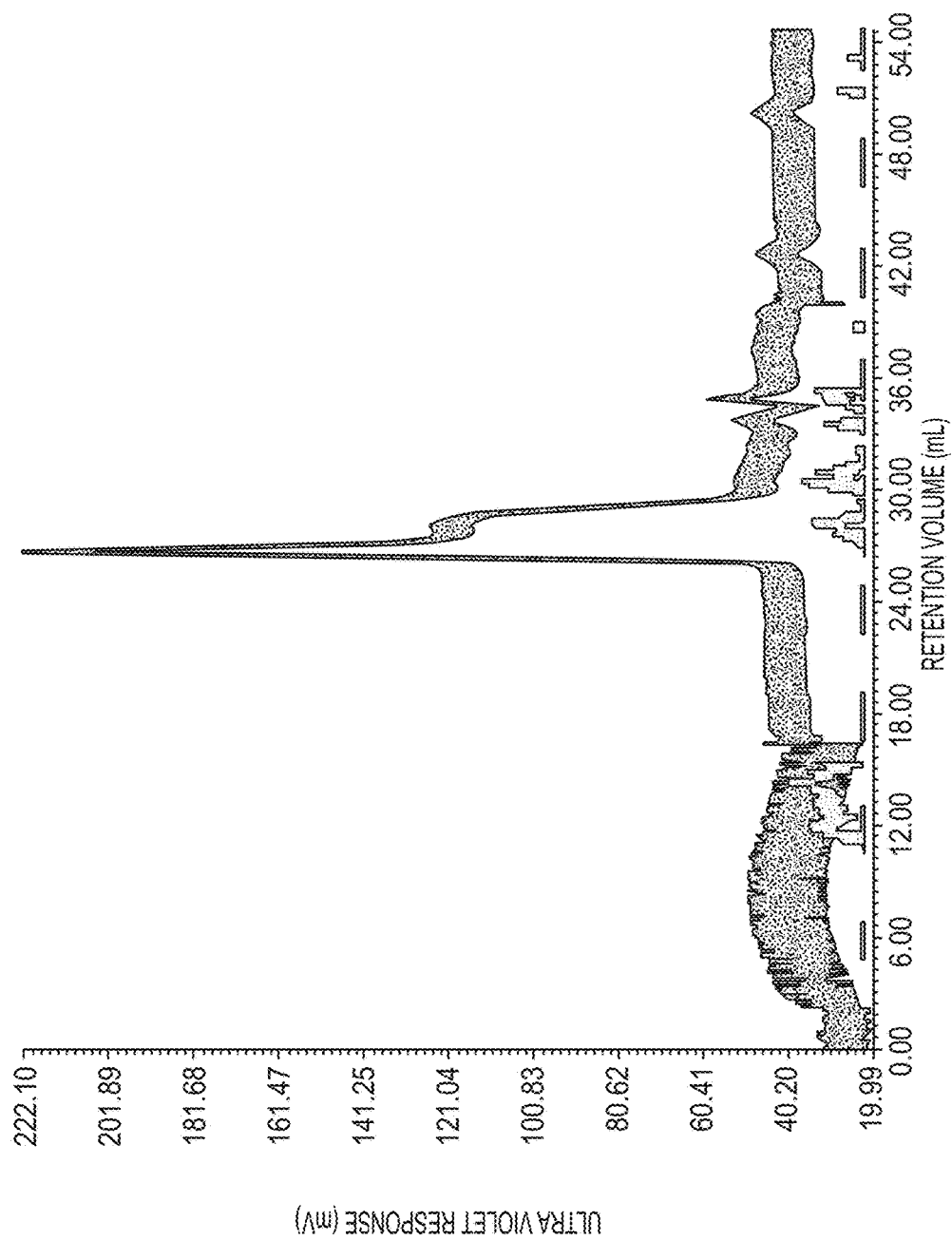
FIG. 1 shows a gel permeation high pressure liquid chromatography (GP-HPLC) of 4-methylumbelliferyl-locust bean gum (4-MU-LBG) and locust bean gum (LBG).

The fractionation of wood biomass into hemicellulose, cellulose and lignin, as described hereinbelow, improves pulp yield and facilitates the separation and release of sugars from their raw material sources. These sugars can then be available for fermentation into biofuels and other basic bioproducts.

Ether bonds between lignin and hemicellulose are a primary reason for the strength of both hardwoods and softwoods and for the difficulty of fractionating both types of wood into their component macromolecules. The polypeptides or enzymes, as described herein, can be used in the early stages of the pulping process to increase the separation of lignin, hemicellulose and cellulose without the concomitant degradation that occurs with current technology. Because the polypeptides or enzymes described herein will not depolymerize any of the polysaccharides, such enzyme pretreatment will lead to increased cellulose yield for the papermaking industry while creating production of separate streams of hemicellulose and lignin for further processing. The enzyme treatment can also be used further downstream (e.g., to brighten paper and decrease the need for chemical bleaching) reducing associated chemical and environmental costs for the pulp and paper industry. Besides improving the quantity and quality of cellulose for paper production, the ability to separate biomass into three distinct feedstocks is advantageous in various other ways.

For example, uses for hemicellulose include fermentation into building blocks for polymers, fine chemicals and chiral chemicals, or into biofuels. Alternatively, the hemicelluloses can be used in animal feed. Most hemicellulose in pulp mills is currently extracted with the black liquor and burned. As a source of heat, hemicelluloses are worth only about $50 per oven-dry metric ton. See van Heiningen, A., Converting a kraft pulp mill into an integrated forest biorefinery, Pulp and Paper Canada, 107:38-43 (2006), which is hereby incorporated by reference in its entirety. If they could be efficiently extracted from wood components and used in a biorefinery as feedstock for the production of ethanol and acetic acid, the downstream value of hemicellulose would approach $1,000 per ton. It is estimated that the $5.5 billion U.S. pulp industry could generate an additional $3.3 billion annually if as few as 100 mills were routinely extracting high-grade hemicelluloses. See van Heiningen, A., 2006, supra.

The remaining lignin can still be burned for heat and energy or sold for synthesis of aromatic fine chemicals. Until now, uses for lignin in fine chemical synthesis have been limited. However, the basic coumaryl substructure of lignin does lend itself to certain classes of chemical syntheses, such as the manufacture of aromatic organic solvents like benzene and phenol. Polymers based on monolignols are being developed, since they can have unique and potentially useful properties due to their hydrophobicity.

A final benefit is that lignins and hemicelluloses are also present in cellulosic agricultural biomass (like corn stover or wheat grass). While the structure of non-woody biomass is simpler, separation still accounts for 60-80% of the production cost for a typical cellulosic fermentation product. See Ragauskas, A. J. et al., 2006, supra. Application of an enzymatic separation method also has the potential to significantly decrease costs for agricultural biomass-derived products.

Definitions

All publications and patent applications mentioned in this specification are herein incorporated by reference in their entirety to the same extent as if each individual publication or patent application was specifically and individually indicated to be incorporated by reference.

Before the invention is disclosed and described in detail, it is to be understood that this invention is not limited to particular compounds, configurations, method steps, substrates, and materials disclosed herein as such compounds, configurations, method steps, substrates, and materials may vary somewhat. It is also to be understood that the terminology employed herein is used for the purpose of describing particular embodiments only and is not intended to be limiting since the scope of the present invention is limited only by the appended claims and equivalents thereof.

If nothing else is defined, any terms and scientific terminology used herein are intended to have the meanings commonly understood by those of skill in the art to which this invention pertains.

The term "about" as used in connection with a numerical value throughout the description and the claims denotes an interval of accuracy, familiar and acceptable to a person skilled in the art. Said interval is ±10%.

As used herein and in the appended claims, the singular "a," "an" and "the" include the plural reference unless the context clearly dictates otherwise. Thus, for example, reference to a "host cell" includes a plurality of such host cells.

Unless otherwise indicated, nucleic acids are written left to right in 5' to 3' orientation; amino acid sequences are written left to right in amino to carboxy orientation, respectively.

As used herein, "hemicellulose:lignin etherases" or "HLEs" are a variety of enzymes that specifically cleave a non-glycosidic ether bond between a lignin or a derivative thereof and a saccharide. The cleavage of non-glycosidic ether bond by HLE may be between an aromatic or a non-aromatic carbon of the lignin or the derivative thereof and the saccharide. HLEs can specifically and gently loosen the lignin away from hemicellulose without significant concomitant degradation. Examples of HLEs may include but are not limited to mannan:lignin etherase ("MLE") and xylan:lignin etherase ("XLE"). HLEs differ from traditional pulping enzyme in that these enzymes break the non-glycosidic ether bonds between lignin and hemicellulose, which are sites of lignin-hemicellulose crosslinks. The end result of HLE action is an intact hemicellulose that can be used either intact or depolymerized by hemicellulases into sugars. Bonds between sugars and lignin are broken, increasing sugar yields and giving purer lignin fractions.

Traditional pulping enzymes (e.g., cellulases and hemicellulases) are glycosidases that only break the glycosidic bonds between the sugars in the hemicellulose and do not break lignin-hemicellulose bonds. In doing this, the hemicellulose structure is destroyed leaving some sugars still attached to the lignin where they are wasted. Under this scenario, the pulp or biomass can be incubated with HLE and a hemicellulase and/or a cellulase, either concurrently or sequentially, to break many of the non-glycosidic bonds between lignin and hemicellulose and most of the glycosidic bonds between sugars.

As used herein, a "mannan:lignin etherase" or "MLE" is a polypeptide that specifically targets mannan, the major hemicellulose of softwoods. An MLE polypeptide is a type of HLE that specifically breaks or cleaves non-glycosidic ether bonds between lignin and mannan. The model substrate is a mannan that has been derivatized with a lignin monomer analog (e.g., 4-methylumbelliferone or 4-MU) at some of the C6 residues of mannan.

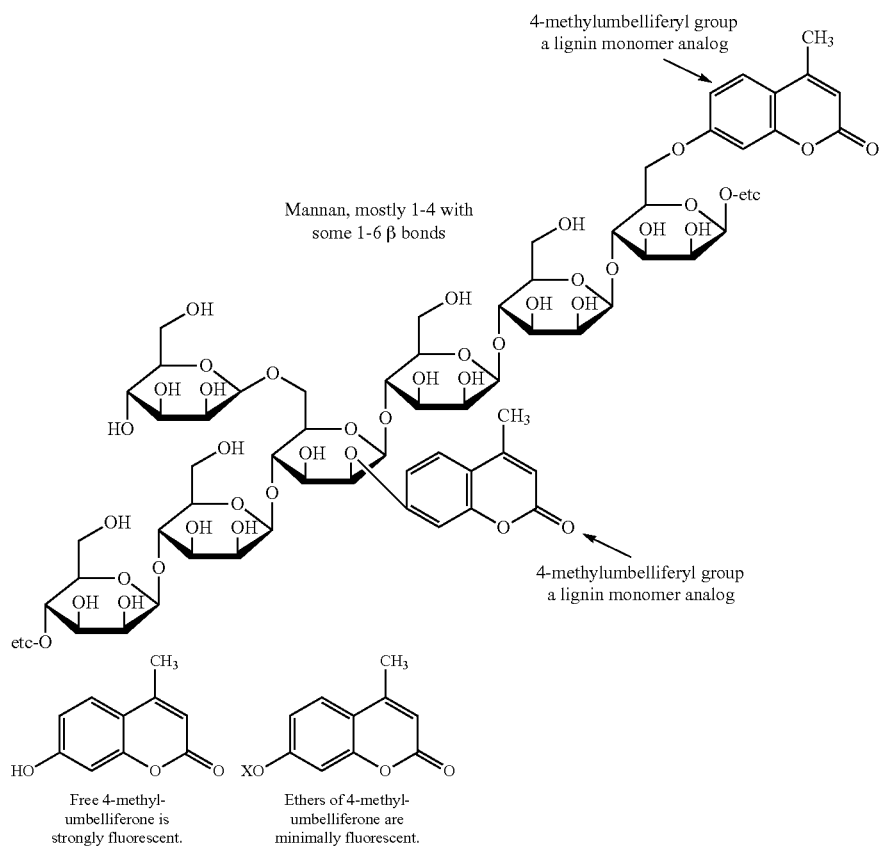

Microorganisms that can Cleave Phenyl Ether Bonds Between 4-Methylumbeliferone and $C_6$ of Residues of Mannan Will Generate Florescence As used herein, a "xylan:lignin etherase" or "XLE" is a polypeptide that specifically cleaves or breaks the phenyl ether bonds between lignin and xylan. The model substrate is xylan that has been derivatized with a lignin monomer analog, 4-methylumbelliferone (4-MU) at some of the 2' and 3' hydroxyl groups.

As discussed above, hemicellulose is linked to lignin by ether bonds and MLE and XLE are enzymatically targeted to the non-glycosidic ether bonds at the aromatic carbon of lignins. However, hemicellulose can also be linked to lignin via non-glycosidic ether bonds at its non-aromatic carbon bonds, e.g., the α- and β-benzyl carbon bonds of lignin. In another embodiment of the invention, hemicellulose:lignin etherases (HLEs) may also include enzymes that break the α- and β-benzyl ether bonds between mannose and lignin. Examples of mannose bonded to a lignin monomer via α- and β-benzyl bonds are provided hereinbelow:

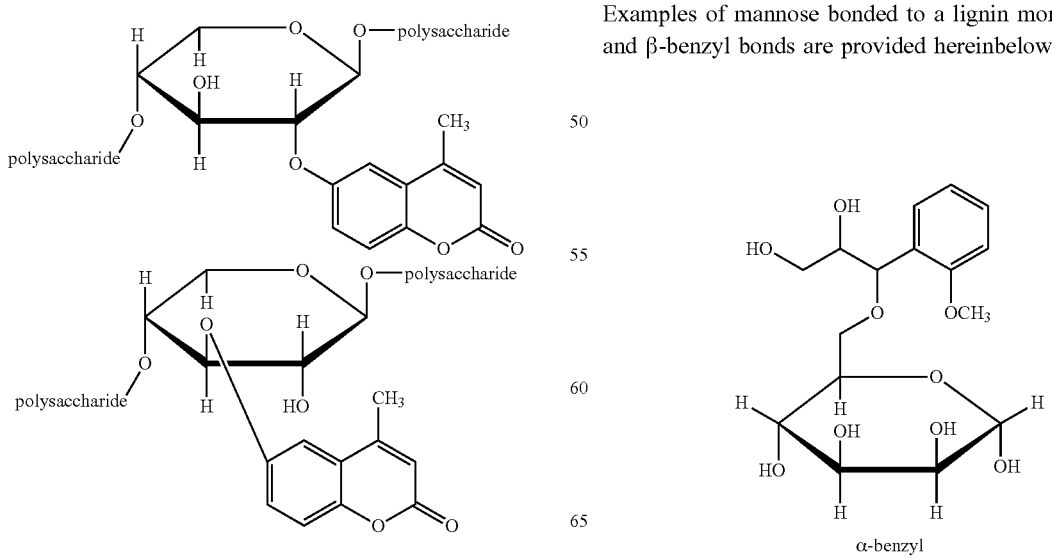

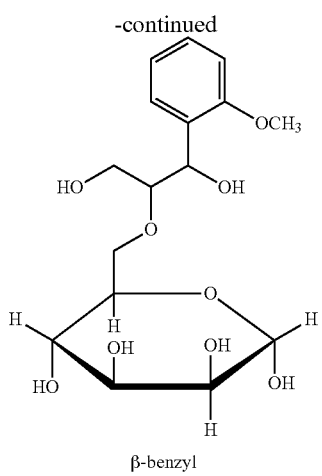

β-benzyl

Examples of softwood include *Araucaria* (e.g. *A. cunninghamii, A. angustifolia, A. araucana*); softwood Cedar (e.g. *Juniperus virginiana, Thuja plicata, Thuja occidentalis, Chamaecyparis thyoides, Callitropsis nootkatensis*); Cypress (e.g. *Chamaecyparis, Cupressus Taxodium, Cupressus arizonica, Taxodium distichum, Chamaecyparis obtusa, Chamaecyparis lawsoniana, Cupressus sempervirens*); European Yew; Fir (e.g. *Abies balsamea, Abies alba, Abies procera, Abies amabilis*); Hemlock (e.g. *Tsuga canadensis, Tsuga mertensiana, Tsuga heterophylla, Tsuga heterotallica*), Douglas fir (*Pseudotsuga menzisii*), Kauri; Kaya; Larch (e.g. *Larix decidua, Larix kaempferi, Larix laricina, Larix occidentalis*); Pine (e.g. *Pinus nigra, Pinus banksiana, Pinus contorta, Pinus radiata, Pinus ponderosa, Pinus resinosa, Pinus sylvestris, Pinus strobus, Pinus monticola, Pinus lambertiana, Pinus taeda, Pinus palustris, Pinus rigida, Pinus echinate, Pinus halepensis, Pinus elliotti, Pinus caribiae*); Redwood (*Sequoia sempervirens*); Rimu; Spruce (e.g. *Picea abies, Picea mariana, Picea rubens, Picea sitchensis, Picea glauca*); Sugi; and combinations/hybrids thereof.

Examples of hardwood include *Acacia* (e.g. *Acacia melanoxylon, Acacia homalophylla, Acacia magnium*); Afzelia; *Synsepalum duloificum*; Albizia; Alder (e.g. *Alnus glutinosa, Alnus rubra*); Applewood; Arbutus; Ash (e.g. *F. nigra, F. quadrangulata, F. excelsior, F. pennsylvanica lanceolata, F. latifolia, F. profunda, F. americana*); Aspen (e.g. *P. grandidentata, P. tremula, P. tremuloides*); Australian Red Cedar (*Toona ciliata*); Ayna (*Distemonanthus benthamianus*); Balsa (*Ochroma pyramidale*); Basswood (e.g. *T. americana, T. heterophyllaI*); Beech (e.g. *F. sylvatica, F. grandifolia*); Birch; (e.g. *Betula populifolia, B. nigra, B. papyrifera, B. lenta, B. alleghaniensis/B. lutea, B. pendula, B. pubescens*); Blackbean; Blackwood; Bocote; Boxelder; Boxwood; Brazilwood; Bubinga; Buckeye (e.g. *Aesculus hippocastanum, Aesculus glabra, Aesculus flava/Aesculus octandra*); Butternut; Catalpa; Cherry (e.g. *Prunus serotina, Prunus pennsylvanica, Prunus avium*); Crabwood; Chestnut; Coachwood; Cocobolo; Corkwood; Cottonwood (e.g. *Populus balsamifera, Populus deltoides, Populus sargentii, Populus heterophylla*); Cucumbertree; Dogwood (e.g. *Cornus florida, Cornus nuttallii*); Ebony (e.g. *Diospyros kurzii, Diospyros melanida, Diospyros crassiflora*); Elm (e.g. *Ulmus americana, Ulmus procera, Ulmus thomasii, Ulmus rubra, Ulmus glabra*); Eucalyptus (e.g. *Eucalyptus grandis, Eucalyptus urograndis*, and *Eucalyptus globulus*); Greenheart; Grenadilla; Gum (e.g. *Nyssa sylvatica, Eucalyptus globulus, Liquidambar styraciflua, Nyssa aquatica*); Hickory (e.g. *Carya alba, Carya glabra, Carya ovata, Carya laciniosa*); Hornbeam; Hophornbeam; Ip; Iroko; Ironwood (e.g. *Bangkirai, Carpinus caroliniana, Casuarina equisetifolia, Choricbangarpia subargentea, Copaifera* spp., *Eusideroxylon zwageri, Guajacum officinale, Guajacum sanctum, Hopea odorata, Ipe, Krugiodendron ferreum, Lyonothamnus lyonii (L. floribundus), Mesua ferrea, Olea* spp., *Olneya tesota, Ostrya virginiana, Parrotia persica, Tabebuia serratifolia*); Jacaranda (*Jacaranda acutifolia*); Jotoba; Lacewood; Laurel; Limba; Lignum vitae; Locust (e.g. *Robinia pseudacacia, Gleditsia triacanthos*); Mahogany; Maple (e.g. *Acer saccharum, Acer nigrum, Acer negundo, Acer rubrum, Acer saccharinum, Acer pseudoplatanus, Acer campestre, Acer platanoides*); Meranti; Mpingo; Oak (e.g. *Quercus macrocarpa, Quercus alba, Quercus stellata, Quercus bicolor, Quercus virginiana, Quercus michauxii, Quercus prinus, Quercus muhlenbergii, Quercus chrysolepis, Quercus lyrata, Quercus robur, Quercus petraea, Quercus rubra, Quercus velutina, Quercus laurifolia, Quercus falcata, Quercus nigra, Quercus phellos, Quercus texana*); Obeche; Okoume; Oregon Myrtle; California Bay Laurel; Pear; Poplar (e.g. *P. balsamifera, P. nigra, Populus balsamifera, P. fremontii* and *P. nigra* Hybrid Poplar (*Populus×canadensi*)); Ramin; Red cedar; Rosewood; Sal; Sandalwood; Sassafras; Satinwood; Silky Oak; Silver Wattle; Snakewood; Sourwood; Spanish cedar; American sycamore; Teak; Walnut (e.g. *Juglans nigra, Juglans regia*); Willow (e.g. *Salix nigra, Salix alba*); Yellow poplar (*Liriodendron tulipifera*); Bamboo; Palmwood; and combinations/hybrids thereof.

"Lignin" is a polyphenolic material comprised of methoxylated phenyl propane units linked by ether and carbon-carbon bonds. Lignins can be highly branched and can also be crosslinked. Lignins can have significant structural variation that depends, at least in part, on the plant source involved. Lignin fills spaces in the cell wall and between cellulose, hemicellulose, and, if present, pectin components.

As used herein, the term "native lignin" refers to lignin in its natural state, in plant material.

Native lignin is a naturally occurring amorphous complex cross-linked organic macromolecule that comprises an integral component of all plant biomass. The chemical structure of lignin is irregular in the sense that different structural units (e.g., phenylpropane units) are not linked to each other in any systematic order. Extracting native lignin from lignocellulosic biomass during pulping generally results in lignin fragmentation into numerous mixtures of irregular components. Furthermore, the lignin fragments may react with any chemicals employed in the pulping process. Consequently, the generated lignin fractions can be referred to as lignin derivatives and/or technical lignins. As it is difficult to elucidate and characterize such complex mixture of molecules, lignin derivatives are usually described in terms of the lignocellulosic plant material used, and the methods by which they are generated and recovered from lignocellulosic plant material, i.e., hardwood lignins, softwood lignins, and annual fiber lignins.

Native lignins are partially depolymerized during the pulping processes into lignin fragments which dissolve in the pulping liquors and are subsequently separated from the cellulosic pulps. Post-pulping liquors containing lignin and polysaccharide fragments, and other extractives are commonly referred to as "black liquors" or "spent liquors," depending on the pulping process. Such liquors are generally considered a by-product, and it is common practice to combust them to recover some energy value in addition to recovering the cooking chemicals. However, it is also possible to precipitate and/or recover lignin derivatives from these liquors. Each type of pulping process used to separate cellulosic pulps from other lignocellulosic components produces lignin derivatives that are very different in their physico-chemical, biochemical, and structural properties.

As used herein, the terms "lignin derivatives" and "derivatives of native lignin" refer to lignin material extracted from lignocellulosic biomass. Usually, such material will be a mixture of chemical compounds that are generated during the extraction process. A lignin derivative may include a lignin mimic.

A "lignin mimic" can refer to a compound, either chemically synthesized or in its natural form, that is capable of mimicking the conformation and desirable features of a natural lignin.

The term "hemicellulose" can refer to polysaccharides comprising mainly sugars or combinations of sugars (e.g., xylose). Hemicellulose can be highly branched. Hemicellulose can be chemically bonded to lignin and can further be randomly acetylated, which can reduce enzymatic hydrolysis of the glycosidic bonds in hemicellulose. See Samuel, R. et al., Structural changes in switchgrass lignin and hemicelluloses during pretreatments by NMR analysis, Polym. Degrad. Stabil., 96(11):2002-2009, (2011), which is hereby incorporated by reference in its entirety. Examples of a hemicellulose include but are not limited to xyloglucan, xylan, mannan, galactomannan, arabinoglucuronoxylan, glucuronoxylan, glucomannan and galactoglucomannan. In one embodiment, the hemicellulose is at least one selected from the group consisting of xylan, arabinoglucuronoxylan, glucuronoxylan, glucomannan, galactomannan and galactoglucomannan.

"Hemicellulose derivative" refers to a structural component of plant cell walls other than cellulose and lignin, or a derivative thereof. Hemicelluloses are heterogeneous and vary depending on the origin of the plant material, but the most commonly found components include xylans, glucomannans, galactans, glucans, and xyloglucans. Thus, upon hydrolysis, hemicellulose may yield glucose, galactose, mannose, xylose, arabinose and/or derivatives thereof.

"Saccharide" refers to monomeric, dimeric oligomeric, or polymeric aldose and ketose carbohydrates. Monosaccharides are simple sugars with multiple hydroxyl groups and exist preferably as cyclic hemiacetals and hemiketals but may also exist in acyclic forms. Stereoisomers of cyclic monosaccharides can exist in α- or β forms and in D- or L-forms. Disaccharides are two monosaccharides that are covalently linked by a glycosidic bond. Saccharides are also found in modified form, either as natural products or as a result of chemical modification during hydrolysis or industrial processing. Saccharide derivatives include those modified by deoxygenation or addition of moieties such as acetyl, amino, or methyl groups. In oligosaccharides and polysaccharides, saccharide monomers are connected by characteristic glycosidic linkages, e.g., β1-4, α1-6, α1-2, α1-3, or β1-2. In some polymers, such as cellulose, the linkages are uniform throughout the polymer, while in others, primarily hemicellulosic materials, the linkages may be mixed. Short (typically 1-3 saccharides) branched side chains may also be present in polysaccharides, typically from hemicellulose.

The term "polysaccharide" is used herein to denote polymeric carbohydrate structure form of monosaccharides joined together by glycosidic bonds. A "heteropolysaccharide" is a polysaccharide with two or more different monosaccharide units. A "homopolysaccharide" is a polysaccharide with one type of monosaccharide unit. "Hemicellulose" is a cell wall polysaccharide of land plants with an amorphous structure. "Wood hemicellulose" is a polysaccharide found in softwoods (conifers) and hardwoods (eudicotyledons).

"Arabinose" refers to the monosaccharide arabinopentose and its derivatives, occurring primarily as L-arabinofuranose in xylans and xyloglucans.

"Galactose" refers to the monosaccharide galacto-hexose and its derivatives, occurring primarily as D-galactopyranose in xylans and glucomannans.

"Glucose" refers to the monosaccharide gluco-hexose and its derivatives, occurring primarily as D-glucopyranose in cellulose, glucomannans, and xyloglucans.

"Hexose" refers to C6 sugars and their derivatives, which may occur in pyranose or furanose form. The hexoses most commonly found in plant material are glucose, galactose, and mannose.

"Mannose" refers to manno-hexose and its derivatives, occurring primarily as D-mannopyranose in glucomannans.

"Pentose" refers to C5 sugars and their derivatives, which may occur in pyranose or furanose form. The pentoses most commonly found in plant material are arabinose and xylose.

"C6 and/or C5 sugar" refers to monosaccharides including, for example, hexose ("C6") sugars (e.g., aldohexoses such as glucose, mannose, galactose, gulose, idose, talose, aldohexose, allose altrose; and ketohexoses such as psicose, fructose, sorbose, tagatose; or others, singly or in any combinations thereof), and/or pentose ("C5") sugars (e.g., aldopentoses such as xylose, arabinose, ribose, lyxose; ketopentoses such as ribulose, xylulose; and others, singly or in any combinations thereof). Hexose is a monosaccharide with six carbon atoms, having the chemical formula $C_6H_{12}O_6$. Hexoses can be classified, for example, by a functional group, with aldohexoses having an aldehyde functional group at position 1, and ketohexoses having a ketone functional group at position 2. As known, 6-carbon aldose sugars can form cyclic hemiacetals, which can include a pyranose structure. In solution, open-chain forms and cyclic forms of 6-carbon aldose sugars can exist in equilibrium, or be present in other relative fractions to each other. Pentose is a monosaccharide with five carbon atoms, having the chemical formula $C_5H_{10}O_5$. Pentose can be classified, for example, into two groups, with aldopentoses having an aldehyde functional group at position 1, and ketopentoses having a ketone functional group at position 2. As known, 5-carbon aldose sugars also can have cyclic hemiacetal forms, which can include a furanose structure or a pyranose structure. The hemiacetal cyclic forms of 5-carbon aldose sugars may spontaneously open and close, wherein mutarotation may occur.

"Xylose" refers to xylo-pentose and its derivatives, occurring primarily as D-xylopyranose in xylans and xyloglucans.

The terms "glycosidic bond" and "glycosidic linkage" refer to a linkage between the hemiacetal group of one saccharide unit and the hydroxyl group of another saccharide unit.

Saccharification is the process of hydrolyzing polymers of the source material, such as cellulose and hemicellulose, or starch, into fermentable mono- and di-saccharides such as cellobiose, glucose, xylose, arabinose, mannose, and galactose. For cellulosic polysaccharides, methods for saccharification include autohydrolysis, acid hydrolysis, and enzymatic hydrolysis. Saccharification and variations thereof refer to the process of converting polysaccharides (e.g., hemicellulose) to fermentable sugars, e.g., through the hydrolysis of glycosidic bonds. Saccharification can be effected with enzymes or chemicals. Enzymes, such as hemicellulases can be added to biomass directly (e.g., as a solid or liquid enzyme additive) or can be produced in situ by microbes (e.g., yeasts, fungi, bacteria, etc.). Saccharification products include, for example, fermentable sugars, such as glucose and other small (low molecular weight) oligosaccharides such as monosaccharides, disaccharides, and trisaccharides.

"Suitable conditions" for saccharification refer to various conditions known to one of skill in the art including pH, temperature, biomass composition, and enzyme composition.

"Fermentation" refers to the biological conversion of a carbon source into a bioproduct by a microorganism. Fermentation may be aerobic or anaerobic. Anaerobic fermentation takes place in a medium or atmosphere substantially free of molecular oxygen.

The term "enzyme" refers to a protein that catalyzes a chemical reaction. In particular, enzymes may include those polypeptides that can specifically cleave or break bonds between saccharides or sugars and lignins at non-glycosidic positions. More particularly, enzymes may include the polypeptides that cleave a non-glycosidic ether bond between a lignin or a derivative thereof and a saccharide. The cleavage of the non-glycosidic ether bond can be between an aromatic or non-aromatic carbon of the lignin or the derivative thereof and the saccharide.

The term "catalytic domain" means the region of an enzyme containing the catalytic machinery of the enzyme. In one embodiment, the catalytic domain comprises amino acids 509-702 of SEQ ID NO:2 or the amino acids of SEQ ID NO:4 having hemicellulose:lignin etherase (HLE) activity.

The term "subsequence" means a polynucleotide having one or more (e.g., several) nucleotides absent from the 5' and/or 3' end of a mature polypeptide coding sequence; wherein the subsequence encodes a catalytic fragment having hemicellulose:lignin etherase (HLE) activity. In one aspect, a subsequence contains at least 585 nucleotides (e.g., nucleotides 1525-2109 of SEQ ID NO:1 and 1-585 of SEQ ID NO:3).

The term "variant" means a polypeptide having hemicellulose:lignin etherase (HLE) activity comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding an amino acid adjacent to and immediately following the amino acid occupying a position. An example of a variant includes the amino acids of SEQ ID NO:4 having hemicellulose:lignin etherase (HLE) activity.

The term "cDNA" means a DNA molecule that can be prepared by reverse transcription from a mature, spliced, mRNA molecule obtained from a eukaryotic or prokaryotic cell. A cDNA lacks intron sequences that may be present in the corresponding genomic DNA. The initial, primary RNA transcript is a precursor to mRNA that is processed through a series of steps, including splicing, before appearing as mature spliced mRNA. A cDNA, according to the embodiment of the invention, encodes a polypeptide that cleaves a non-glycosidic ether bond between a lignin or a derivative thereof and a saccharide. The cleavage of the non-glycosidic ether bond can be between an aromatic or non-aromatic carbon of the lignin or the derivative thereof and the saccharide. In one embodiment, a cDNA encompasses a nucleotide sequence of SEQ ID NO:1 or SEQ ID NO:3.

In one embodiment, a cDNA encompasses a nucleotide sequence of SEQ ID NO:49.

The term "coding sequence" means a polynucleotide which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

The term "control sequences" means nucleic acid sequences necessary for expression of a polynucleotide encoding a mature polypeptide of the present invention. Each control sequence may be native (i.e., from the same gene) or foreign (i.e., from a different gene) to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

The control sequence may also be an appropriate promoter sequence which is recognized by a host cell for expression of the isolated polynucleotide sequence of the present invention. The promoter sequence contains transcriptional control sequences which mediate the expression of the HLEs. The promoter may be any nucleic acid sequence which shows transcriptional activity in the host cell of choice including mutant, truncated, and hybrid promoters, and may be obtained from genes encoding extracellular or intracellular polypeptides either homologous or heterologous to the host cell.

The term "expression" includes any step involved in the production of a polypeptide including, but not limited to, transcription, post-transcriptional modification, translation, post-translational modification, and secretion.

The term "expression vector" means a linear or circular DNA molecule that comprises a polynucleotide encoding a polypeptide and is operably linked to control sequences that provide for its expression. Examples expression vectors include but are not limited to pHIS525-cMLE, pHIS525-cfMLE, pAES40-cMLE, pAES40-cfMLE, pHT43-cMLE, pHT43-cfMLE, pBluescript SK$^-$-cMLE, pBluescript SK$^-$-cfMLE, pFN6A-cMLE and pFN6A-cfMLE.

The term "host cell" means any cell type that is susceptible to transformation, transfection, transduction, or the like with a nucleic acid construct or expression vector comprising the isolated polynucleotide of the present invention. The term "host cell" encompasses any progeny of a parent cell that is not identical to the parent cell due to mutations that occur during replication. Examples of host cells include but are not limited to *Escherichia coli, Bacillus megaterium*, and *Bacillus subtilis*.

Recombinant host cells, according to the embodiment of the invention comprise a complementary DNA (cDNA) sequence encoding a polypeptide that cleaves a non-glycosidic ether bond between a lignin or a derivative thereof and a saccharide.

The term "purified" or "isolated," in relation to an enzyme or nucleic acid, indicates the enzyme or nucleic acid is not in its natural medium or form. The term "isolated" thus includes an enzyme or nucleic acid removed from its original environment, e.g., the natural environment if it is naturally occurring. For instance, an isolated enzyme is typically devoid of at least some proteins or other constituents of the cells to which it is normally associated or with which it is normally admixed or in solution. An isolated enzyme includes said enzyme naturally-produced contained in a cell lysate or secreted into a culture supernatant; the enzyme in a purified or partially purified form, the recombinant enzyme, the enzyme which is expressed or secreted by a bacterium, as well as the enzyme in a heterologous host cell or culture. In relation to a nucleic acid, the term isolated or purified indicates e.g., that the nucleic acid is not in its natural genomic context (e.g., in a vector, as an expression cassette, linked to a promoter, or artificially introduced in a heterologous host cell).

As used herein, "heterologous" in reference to a nucleic acid (cDNA or polynucleotide) or protein (polypeptide) includes a molecule that has been manipulated by human intervention so that it is located in a place other than the place in which it is naturally found. For example, a nucleic acid sequence from one organism (e.g. from one strain or species) may be introduced into the genome of another organism (e.g. of another strain or species), or a nucleic acid sequence from one genomic locus may be moved to another genomic or extrachromosomal locus in the same organism. A heterologous protein includes, for example, a protein expressed from a heterologous coding sequence or a protein expressed from a recombinant gene in a cell that would not naturally express the protein.

The term "nucleic acid construct" means a nucleic acid molecule, either single- or double-stranded, which is isolated from a naturally occurring gene or is modified to contain segments of nucleic acids in a manner that would not otherwise exist in nature or which is synthetic that comprises one or more control sequences.

The term "operably linked" means a configuration in which a control sequence is placed at an appropriate position relative to the coding sequence of a polynucleotide such that the control sequence directs expression of the coding sequence.

As used herein, "identity" and "percent identity," in the context of two or more polypeptide sequences, refers to two or more sequences or subsequences that are the same or have a specified percentage of amino acid residues that are the same (e.g., share at least about 70%, at least about 75%, at least about 80%, at least about 85%, at least about 88% identity, at least about 89%, at least about 90%, at least about 91%, at least about 92%, at least about 93%, at least about 94%, at least about 95%, at least about 96%, at least about 97%, at least about 98%, or at least about 99% identity) over a specified region to a reference sequence, when compared and aligned for maximum correspondence over a comparison window, or designated region as measured using a sequence comparison algorithms or by manual alignment and visual inspection.

In some embodiments, the terms "percent identity," "% identity," "percent identical," and "% identical" are used interchangeably herein to refer to the percent amino acid or polynucleotide sequence identity that is obtained by ClustalW analysis (version W 1.8 available from European Bioinformatics Institute, Cambridge, UK) or by Clustal Omega analysis (see Sievers F., et al., Fast, scalable generation of high-quality protein multiple sequence alignments using Clustal Omega, Mol. Syst. Biol., 7(539):1-6 (2011), which is incorporated herein by reference in its entirety) that is available from University College Dublin (Dublin, Ireland), counting the number of identical matches in the alignment and dividing such number of identical matches by the length of the reference sequence, and using the following ClustalW parameters to achieve slow/more accurate pairwise optimal alignments—DNA/Protein Gap Open Penalty: 15/10; DNA/Protein Gap Extension Penalty: 6.66/0.1; Protein weight matrix: Gonnet series; DNA weight matrix: Identity.

Two sequences are "aligned" when they are aligned for similarity scoring using a defined amino acid substitution matrix (e.g., BLOSUM62), gap existence penalty and gap extension penalty so as to arrive at the highest score possible for that pair of sequences. Amino acid substitution matrices and their use in quantifying the similarity between two sequences are well known in the art. See, e.g., Dayhoff et al., in Dayhoff (ed.), Atlas of Protein Sequence and Structure," Vol. 5, Suppl. 3, Natl. Biomed. Res. Round., Washington, D.C. (1978); pp. 345-352; and Henikoff, S. and Henikoff, J. G., Proc. Natl. Acad. Sci. USA, 89:10915-10919 (1992), both of which are incorporated herein by reference in their entirety). The BLOSUM62 matrix is often used as a default scoring substitution matrix in sequence alignment protocols such as Gapped BLAST 2.0. The gap existence penalty is imposed for the introduction of a single amino acid gap in one of the aligned sequences, and the gap extension penalty is imposed for each additional empty amino acid position inserted into an already opened gap. The alignment is defined by the amino acid position of each sequence at which the alignment begins and ends, and optionally by the insertion of a gap or multiple gaps in one or both sequences so as to arrive at the highest possible score. While optimal alignment and scoring can be accomplished manually, the process is facilitated by the use of a computer-implemented alignment algorithm (e.g., gapped BLAST 2.0; See, Altschul et al., Nucleic Acids Res., 25:3389-3402 (1997), which is incorporated herein by reference in its entirety, and made available to the public at the National Center for Biotechnology Information Website). Optimal alignments, including multiple alignments can be prepared using readily available programs such as PSI-BLAST (See e.g., Altschul et al., 1997, supra).

The present invention also provides a recombinant nucleic acid construct comprising a polynucleotide sequence that hybridizes under stringent hybridization conditions to the complement of a polynucleotide which encodes a polypeptide having the amino acid sequence of SEQ ID NO:2 and/or 4.

The present invention also provides a recombinant nucleic acid construct comprising a polynucleotide sequence that hybridizes under stringent hybridization conditions to the complement of a polynucleotide which encodes a polypeptide having the amino acid sequence of SEQ ID NO:50.

Two nucleic acid or polypeptide sequences that have 100% sequence identity are said to be "identical." A nucleic acid or polypeptide sequence is said to have "substantial sequence identity" to a reference sequence when the sequences have at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99%, or greater sequence identity as determined using the methods described herein, such as BLAST using standard parameters.

As used herein, a "secretion signal peptide" can be a propeptide, a prepeptide or both. For example, the term "propeptide" refers to a protein precursor that is cleaved to yield a "mature protein." The signal peptide is cleaved from the pre-protein by a signal peptidase prior to secretion to result in the "mature" or "secreted" protein. The terms "prepeptide" and "pre-protein" refer to a polypeptide synthesized with an N-terminal signal peptide that targets it for secretion. Accordingly, a "pre-pro-peptide" is a polypeptide that contains a signal peptide that targets the polypeptide for secretion and which is cleaved off to yield a mature polypeptide. Signal peptides can be found at the N-terminus of the protein and may typically compose of between 6 to 136 basic and hydrophobic amino acids.

The term "mature polypeptide" means a polypeptide having HLE activity or capable of specifically cleaving a non-glycosidic ether bond between a lignin or a derivative thereof and a polysaccharide in its final form following translation and any post-translational modifications. It is known in the art that a host cell may produce a mixture of two of more different mature polypeptides (i.e., with a different C-terminal and/or N-terminal amino acid) expressed by the same polynucleotide. The mature polypeptide can be predicted using the SignalP program. See Nielsen et al., Protein Engineering 10:1-6 (1997), which is hereby incorporated by reference in its entirety.

The term "mature polypeptide coding sequence" is defined herein as a nucleotide sequence that encodes a mature polypeptide having HLE activity or capable of specifically cleaving a non-glycosidic ether bond between a lignin or a derivative thereof and a saccharide. The mature polypeptide coding sequence can be predicted using the SignalP program. See Nielsen et al., 1997, supra.

The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 70° C.

The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 65° C.

The term "medium-high stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 60° C.

The term "medium stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 55° C.

The term "low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 50° C.

The term "very low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 45° C.

In an embodiment, the present invention relates to isolated polypeptides having a sequence identity to the polypeptide of SEQ ID NO:2 or SEQ ID NO:4 or an allelic variant thereof or a fragment thereof, of at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or 100%; which have HLE activity or are capable of specifically cleaving a non-glycosidic ether bond between a lignin or a derivative thereof and a saccharide or a derivative thereof (such as an acetylated saccharide). In one aspect, the polypeptides differ by up to 10 amino acids, e.g., 1, 2, 3, 4, 5, 6, 7, 8, 9, or 10 from the polypeptide of SEQ ID NO:2, or SEQ ID NO:4.

In an embodiment, the present invention relates to isolated polypeptides having a sequence identity to the polypeptide of SEQ ID NO:50 or an allelic variant thereof or a fragment thereof, of at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or 100%; which have HLE activity or are capable of specifically cleaving a non-glycosidic ether bond between a lignin or a derivative thereof and a saccharide or a derivative thereof (such as an acetylated saccharide). In one embodiment, the polypeptides differ by up to 10 amino acids, e.g., 1, 2, 3, 4, 5, 6, 7, 8, 9, or 10 from the polypeptide of SEQ ID NO:50.

An isolated polypeptide of the present invention preferably comprises or consists of the amino acid sequence of SEQ ID NO:2, SEQ ID NO:4 or an allelic variant thereof; or a fragment thereof having HLE activity or capable of specifically cleaving a non-glycosidic ether bond between a lignin or a derivative thereof and a saccharide. In another aspect, the polypeptide comprises or consists of the mature polypeptide of SEQ ID NO:2 or SEQ ID NO:4. In another aspect, the isolated polypeptide comprises or consists of amino acids 509 to 702 of SEQ ID NO:2. In another aspect, the polypeptide comprises or consists of amino acids of SEQ ID NO:4. In another embodiment, the present invention relates to isolated polypeptides having HLE activity that are encoded by polynucleotides that hybridize under very low stringency conditions, low stringency conditions, medium stringency conditions, medium-high stringency conditions, high stringency conditions, or very high stringency conditions with (i) the polypeptide coding sequence of SEQ ID NO:1 or the cDNA sequence thereof, the mature polypeptide coding sequence of SEQ ID NO:3 or the cDNA sequence thereof, or (ii) the full-length complement of (i). See Sambrook et al., 1989, Molecular Cloning, A Laboratory Manual, 2d edition, Cold Spring Harbor, N.Y., which is hereby incorporated by reference in its entirety.

An isolated polypeptide of the present invention preferably comprises or consists of the amino acid sequence of SEQ ID NO:50 or an allelic variant thereof; or a fragment thereof having HLE activity or capable of specifically cleaving a non-glycosidic ether bond between a lignin or a derivative thereof and a saccharide. Alternatively, the polypeptide comprises or consists of the mature polypeptide of SEQ ID NO:50. In another embodiment, the present invention relates to isolated polypeptides having HLE activity that are encoded by polynucleotides that hybridize under very low stringency conditions, low stringency conditions, medium stringency conditions, medium-high stringency conditions, high stringency conditions, or very high stringency conditions with (i) the polypeptide coding sequence of SEQ ID NO:49 or the cDNA sequence thereof, or (ii) the full-length complement of (i). See Sambrook et al., 1989, Molecular Cloning, A Laboratory Manual, 2d edition, Cold Spring Harbor, N.Y., which is hereby incorporated by reference in its entirety.

A genomic DNA or cDNA library prepared from such other host strains may be screened for DNA that hybridizes with the probes described herein and encodes a polypeptide having HLE activity or capable of specifically cleaving a non-glycosidic ether bond between a lignin or a derivative thereof and a saccharide. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that is homologous with SEQ ID NO:1 or SEQ ID NO:3, or a subsequence thereof, the carrier material is used in a Southern blot.

Similarly, to identify a clone or DNA that is homologous with SEQ ID NO:49, or a subsequence thereof, the carrier material is used in a Southern blot.

For purposes of the present invention, hybridization indicates that the polynucleotide hybridizes to a labeled nucleic acid probe corresponding to SEQ ID NO:1 or the cDNA sequence thereof, or SEQ ID NO:3 or the cDNA sequence thereof; the mature polypeptide coding sequence of SEQ ID NO:1, or the mature polypeptide coding sequence of SEQ ID NO:3; the full-length complement thereof; or a subsequence thereof; under very low to very high stringency conditions. Molecules to which the nucleic acid probe hybridizes under these conditions can be detected using, for example, X-ray film or any other detection means known in the art.

Hybridization also includes that the polynucleotide hybridizes to a labeled nucleic acid probe corresponding to SEQ ID NO:49 or the cDNA sequence thereof; the mature polypeptide coding sequence of SEQ ID NO:49; the full-length complement thereof; or a subsequence thereof; under very low to very high stringency conditions. Molecules to which the nucleic acid probe hybridizes under these conditions can be detected using, for example, X-ray film or any other detection means known in the art.

In another embodiment, the present invention relates to isolated polypeptides having HLE activity encoded by polynucleotides having a sequence identity to the polypeptide coding sequence of SEQ ID NO: 1 or the cDNA sequence thereof, or the mature polypeptide coding sequence of SEQ ID NO: 3 or the cDNA sequence thereof, of at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or 100%.

In another embodiment, the present invention relates to isolated polypeptides having HLE activity encoded by polynucleotides having a sequence identity to the polypeptide coding sequence of SEQ ID NO: 49 or the cDNA sequence thereof, of at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or 100%.

In another embodiment, the present invention relates to variants of the mature polypeptide of SEQ ID NO: 2 or SEQ ID NO: 4, comprising a substitution, deletion, and/or insertion at one or more (e.g., several) positions. In an embodiment, the number of amino acid substitutions, deletions and/or insertions introduced into the mature polypeptide of SEQ ID NO: 2 or SEQ ID NO: 4 is not more than 10, e.g., 1, 2, 3, 4, 5, 6, 7, 8, 9, or 10. The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

In another embodiment, the present invention relates to variants of the mature polypeptide of SEQ ID NO: 50, comprising a substitution, deletion, and/or insertion at one or more (e.g., several) positions. In an embodiment, the number of amino acid substitutions, deletions and/or insertions introduced into the mature polypeptide of SEQ ID NO: 50 is not more than 10, e.g., 1, 2, 3, 4, 5, 6, 7, 8, 9, or 10. The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

The nucleic acid constructs may include an expression vector that includes a cDNA molecule encoding the polypeptide having HLE activity operably linked to one or more control sequences that direct the expression of the coding sequence in a suitable transformed host cell under conditions compatible with the control sequences.

Also included herein are methods of producing heterologous polypeptides of the present invention, comprising: (a) cultivating a recombinant or transformed host cell under conditions conducive for production of the polypeptide; and (b) recovering the heterologous polypeptide. The heterologous polypeptide may be defined herein as a polypeptide which is not native to the host cell, a native protein in which modifications have been made to alter the native sequence or a native protein whose expression is quantitatively altered as a result of a manipulation of the host cell by recombinant DNA techniques.

The recombinant or transformed host cells are cultivated in a nutrient medium suitable for production of the heterologous polypeptides using methods known in the art. For example, the cells may be cultivated by shake flask cultivation, or small-scale or large-scale fermentation (including continuous, batch, fed-batch, or solid state fermentations) in laboratory or industrial fermentors, in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the heterologous polypeptide is secreted into the nutrient medium, the heterologous polypeptide can be recovered directly from the medium. If the heterologous polypeptide is not secreted, it may be recovered from cell lysates.

The heterologous polypeptide may be detected using methods known in the art that are specific for the heterologous polypeptides. These detection methods include, but are not limited to, use of specific antibodies, formation of an enzyme product, or disappearance of an enzyme substrate. For example, an enzyme assay may be used to determine the activity of the polypeptide. The HLEs can be monitored or measured by gel permeation high pressure liquid chromatography (HPLC) or SDS-polyacrylamide gel electrophoresis (SDS-PAGE).

The heterologous polypeptide may be recovered using methods known in the art. For example, the heterologous polypeptide may be recovered from the nutrient medium by conventional procedures including, but not limited to, collection, centrifugation, filtration, extraction, spray-drying, evaporation, or precipitation and/or a combination thereof. In one aspect, the whole fermentation broth is recovered.

The heterologous polypeptide may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., Janson, J.-C. and Ryden, L. (eds), Protein Purification: Principles, High Resolution Methods and Applications, VCH Publishers, Inc., NY, 1989, which is hereby incorporated by reference in its entirety) to obtain substantially pure polypeptides.

According to the embodiments of the inventions, bioprospecting and developing polypeptides or enzymes that specifically cleave non-glycosidic ether bonds between a lignin or a derivative thereof and a polysaccharide (e.g., mannan or xylan) using a lignin fluorogenic analog (e.g., 4-methylumbelliferone derivative or 4-MU) based on hemicellulose are described in more detail in the sections that follow. Derivatization of a polysaccharide (e.g., galactomannan such as locust bean gum) can be carried out as follows: (a) solubilizing a polysaccharide in an aqueous solvent (e.g., water); (b) inducing or precipitating the solubilized polysaccharide with at least two volumes (50-100%) of dimethylformamide (DMF; an organic solvent) to form a gel, (c) optionally, washing the gel with additional dimethylformamide:water (2:1) mixture; (d) mixing the gel with a few drops of DMF, a 10-fold molar excess of a fluorescent phenylacetate derivative (wherein the reactant is a 4-methylumbelliferone derivative (e.g., 4-methylumbelliferyl acetate or a 4-methylumbelliferone esterified with a good leaving group) and a molar excess of a catalyst (e.g., N-bromosuccinamide or NBS); (e) incubating the gel mixture at a temperature ranging from at least about 25° C. to about 90° C. for about 1 hour to overnight (from about 60° C. to about 90° C.) to form a derivatized polysaccharide mixture; and (f) washing the derivatized polysaccharide mixture with a solvent (e.g., DMF and/or 95% ethanol; acetone to remove any free phenylacetate derivative. Examples of saccharides that contain 6-carbon sugars in a pyranose configuration may include, but are not limited to, mannose, mannan, galactomannan (e.g., locust bean gum), cellulose, galactan or hemicellulose. An example of a polysaccharide containing a 5 carbon sugar in the pyranose configuration is xylan. The derivatized polysaccharide, 4-methylumbellyferyl (4-MU)-locust bean gum (4MU-LBG)) can be measured or monitored by gel permeation HPLC. See Sun, X.-F. et al., Acetylation of sugarcane bagasse hemicelluloses under mild reaction conditions by using NBS as a catalyst, J. Appl. Polym. Sci., 95(1):53-61 (2004), which is hereby incorporated by reference in its entirety.

In another embodiment, an exemplary method for preparing a derivatized mixture of polysaccharide composed of 5-carbon sugars (e.g. 4-methylumbelliferyl (4-MU)-xylan) may encompass the following: (a) hydrolyzing a xylan polymer under controlled conditions to form a residue; (b) refluxing the xylan polymer residue in dry methanol to yield methylated free glycosidic hydroxyl groups; (c) benzylating non-glycosidic hydroxyl residues of the xylan polymer with benzyl bromide using DMSO as a solvent and crown ether (benzo-18-crown-6) as a catalyst; (d) displacing the benzyl groups with triflic (trifluoromethanesulfonic) anhydride to convert the hydroxyl groups of the xylan polymer to suitable leaving groups; (e) brominating with tetra-N-butylammonium bromide to displace the leaving groups with halide anions; and (f) reacting the brominated xylan polymer with a fluorescent phenylacetate derivative (4-MU) to form a derivatized xylan (4MU-xylan). The polysaccharide, as used herein, is composed primarily of 5-carbon sugars in a pyranose configuration (e.g., xylose or xylan) derivatized on C2 or C3. The derivatized polysaccharide, 4-methylumbellyferyl (4-MU)-xylan can also be measured or monitored by gel permeation HPLC, infrared spectroscopy or nuclear magnetic resonance (NMR).

EXAMPLES

Derivatizing Non-Glycosidic Carbons of Saccharides with Phenyl Ether Derivatives Most derivatives of saccharides (monosaccharides, disaccharides, oligosaccharides, galactomannan, cellulose, galactan or polysaccharides that incorporate 6-carbon sugars in the pyranose configuration or polysaccharides that incorporate sugars such as heptopyranoses or 5-carbon sugars in the pyranose configuration and that have primary hydroxyls) are prepared by completely solubilizing the polysaccharide in an aqueous or organic solvent. Polymeric material, especially natural polysaccharides, are diverse in molecular weight and their solubility varies with molecular weight. In this method, a solid-phase method was developed based on an unusual modification of a method in a previous study that devised a catalytic acetylation of xylan (a pentopyranose) in a semi-dry gel phase. See Sun, X. F. et al., 2004, supra.

Briefly, the water-solubilized polysaccharide was precipitated with two volumes (50-100% ratio) of dimethylformamide (DMF) to induce gel formation. The excess DMF/water solution was removed by filtration or by simply removing the gel to a fresh tube with forceps or some other simple method known to one skilled in the art. The gel may or may not be washed with additional DMF or DMF:water (2:1) mixture, and it may or may not be treated to increase its surface area to volume ratio, for example by mincing it manually with a razor blade. The gel was combined with a reactant composed of a phenyl acetate derivative (e.g., 4-methylumbelliferyl (4-MU) acetate, 4-MU, 4-MU-phosphate or 4-methylumbelliferone esterified with another leaving group) in approximately 10-fold molar excess to the number of residues of hexopyranose in the polysaccharide. N-bromosuccinamide (NBS) as a catalyst was added in very large molar excess. The mixture was incubated at elevated temperature (from at least about 37° C. to about 80° C.) for anywhere from one hour to overnight. During the incubation, the reaction mixture turned yellow within 10 minutes, then orange, and finally brown. The time course of the color change was dependent on the concentration of NBS, the nature and concentration of the phenyl acetate derivative and the incubation temperature.

Example 1

A 1% solution of locust bean gum (LBG) from *Ceratonia siligua* seeds (Sigma G0753) was prepared in water and heated gently to dissolve as much as possible. Ten ml of LBG suspension was combined with 5 ml of DMF. The mixture was vortexed and used immediately or stored at 4° C. overnight or longer. Afterwards, the precipitate was filtered on Whatman P9 or another coarse grade of filter paper in a Buchner funnel on an aspirator. The swollen gel was washed on the filter paper with additional DMF, but not dried further. Approximately half of the swollen gel (about 0.5 g of LBG) was transferred to an amber glass vial. Six mg of 4MU-Ac (4-methylumbelliferyl acetate, Sigma M0883) dissolved in about 50 microliters of DMF was added. About 0.1 g of dry NBS was added. The mixture was vortexed and incubated in the dark overnight at 65° C. in a heat block. The vials were periodically removed, mixed by vortexing and returned to the heat block. The next morning, 20 ml of 95% ethanol was added and vortexed. The mixture was filtered on a Buchner funnel and washed several times with ethanol and finally with acetone. Washing can be done in a number of solvents that do not dissolve the polysaccharides (e.g., ethanol, acetone or DMF). The resulting brownish powder was dried at room temperature in the dark until the acetone smell was gone and the material appeared dry.

Example 2

LBG was first partially hydrolyzed and filtered to decrease the viscosity and make the polymer size distribution narrower. For partial hydrolysis, 5 g LBG was gradually added to 400 ml distilled water, stirred for 2 hours at room temperature and refrigerated overnight or longer. The suspension was re-equilibrated to room temperature with stirring. The temperature was increased to 70° C. with stirring and held at 70° C. for 30 minutes while stirring. The preparation was allowed to cool to room temperature to form a viscous suspension. The pH was adjusted to 3 with acetic acid and the beaker was covered with aluminum foil. The preparation was autoclaved for 100 minutes at 130° C. to hydrolyze some of the glycosidic bonds in the polymer and reduce the viscosity. The autoclaved mixture was neutralized with 3M NaOH to a pH of approximately 5.5, allowed to cool to room temperature, and the pH was readjusted to 7.0. Large insoluble precipitates were removed by filtration through a Whatman P8 filter in a Buchner funnel attached to a water aspirator. The filtrate volume was reduced either by evaporation or by partial lyophilization, and the final volume was adjusted to 100 ml. Three volumes of 95% ethanol were added to the remaining solution with stirring. The solution was allowed to stir for several hours to ensure complete precipitation, and the precipitate was collected on a P8 filter as before, washed twice with 95% ethanol on the filter, and lyophilized. The dried LBG could be stored indefinitely at 4° C.

Prior to reaction with 4MU-acetate (4MU-Ac), the hydrolyzed LBG was re-equilibrated with DMF. 0.5 g of LBG prepared as above was combined with 8 ml of 100% DMF in a vial. The vial was put into a 65° C. heat block for 4 days (3 nights) with occasional mixing. 50 mg of 4MU-Ac was added and the vial was vortexed. 0.5 g NBS (N-bromosuccinamide, Sigma B81255) was immediately added and the vial was mixed again by vortexing. The lightly capped vial was incubated at 65° C. overnight, with frequent vortexing over the first few hours. Following the reaction, the reaction mix was transferred to a beaker, and 100 ml DMF was used to rinse the vial. The rinse was subsequently added to the beaker. The mixture was stirred for 10 minutes at room temperature and the precipitate was collected on a P8 filter as before. The precipitate was removed to a beaker and washed with 100 ml of 95% ethanol, and refiltered. This process was repeated twice, for a total of 3 washes in 95% ethanol. The final precipitate was lyophilized and the dry powder stored at −20° C.

Proof of Derivatization from Example 1:

1. Lack of underivatized 4MU. Free 4MU is highly fluorescent at alkaline pH. Ether-derivatized 4MU is not. See Robinson, D., The fluorometric determination of β-glucosidase: its occurrence in the tissues of animals, including insects, Biochem. J., 63:39 (1956), which is hereby incorporated by reference in its entirety. Consequently, an increase in fluorescence when a solution's pH is adjusted to alkaline can be indicative of the presence of free 4MU. When 4MU-LBG was dissolved in a balanced salt solution at pH 5.5 and adjusted to pH 10 with 0.1M borate buffer, the fluorescence was very similar to its fluorescence at pH 5.5.

2. Lack of glycosidic 4MU. The locust bean gum used in this example consisted of a polymannose backbone with single galactose residues on approximately every 5th mannose residue, linked to mannose residues by a 1-6 β-bond. Consequently, the vast majority of mannose residues did not have a free C1 hydroxyl, since those groups were already part of a glycosidic bond. Similarly, virtually all of the galactose residues did not have a free C1 hydroxyl as that group was part of the branching C1→C6 glycosidic bond. To determine whether any 4MU reacted with a C1 hydroxyl group, 4MU-LBG was digested with a commercial hemicellulase. Commercial hemicellulase is a mixture of enzymes containing, among others, mannanase, xylanase, β-galactosidase and β-mannosidase. The mixture digested hemicelluloses including mannans down to a mixture of mono-, di- and tri-saccharides. Therefore, the mixed hemicellulase may liberate any 4MU bound through a glycosidic bond, whether to mannose or to galactose. The fluorescence intensity at pH 10 was not increased by incubation with commercial hemicellulose.

To extend these results and rule out any incorporation of 4MU via α-glycosidic bonds, the derivatized LBG was digested with commercially available α- and β-mannosidases, as well as with commercially available α- and β-galactosidases. As a positive control, the commercially available 4MU-derivatized α- and β-mannose and α- and β-galactose were included as internal controls in some digestions. Table I shows the results. No enzyme liberated any fluorescence from 4MU-LBG. The presence of 4MU-LBG did not affect the hydrolysis of any of the commercial substrate, indicating a lack of competition of 4MU-LBG for any of the enzymes.

TABLE I

Effect of Commercial Glycoside Hydrolases on 4 MU-derivatized LBG.

| Enzyme | Negative Control | Cognate 4 MU-pyranoside | 4MU-LBG | 4 MU-LBG + cognate 4 MU-pyranoside (internal control) |
|---|---|---|---|---|
| α-galactosidase | 94 | 50,971 | 94 | 49,471 |
| β-galactosidase | 92 | 127,112 | 100 | 116,781 |
| α-mannosidase | 114 | 115,450 | 94 | 97,181 |
| β-mannosidase | 127 | 120,332 | 114 | 113,240 |

In addition, treatment of polysaccharides with 4% sulfuric acid at 250° C. for 60 minutes is a standard method to hydrolyze glycosidic bonds in polysaccharides. See Sluiter, A. et al., Determination of Structural Carbohydrates and Lignin in Biomass, Laboratory Analytical Procedure (LAP) (Version Jul. 8, 2011), Technical Report NREL/TP-510-42618 (2001), which is hereby incorporated by reference in its entirety.

Non-glycosidic ether bonds are not hydrolyzed by this procedure, however ester bonds are hydrolyzed. If 4MU is derivatized via a glycosidic ether bond or via an ester bond, the acid hydrolysis treatment should liberate free 4MU. Putatively labeled locust bean gum was hydrolyzed in 4% sulfuric acid at 250° C. for 60 minutes. The treated samples were adjusted to pH 10 with concentrated borate buffer and their fluorescence determined as above. No increase in fluorescence was found.

3. Presence of 4MU on high molecular weight material. 4MU-LBG was analyzed by GP-HPLC. The system had detectors for both refractive index changes and for $OD_{254}$ absorbance. A peak of UV absorbance was detected in the column flow and its retention volume was consistent with hemicellulose. FIG. 1 shows column profile at $OD_{254}$ for both 4MU-derivatized LBG and LBG that had been treated identically except that no 4MU acetate was added to the reaction tube. Locust bean gum that had been putatively derivatized with 4MU had significant absorbance at $OD_{254}$ at the RID peak (red line in FIG. 1) while underivatized locust bean gum had no absorbance at 254 nm at the peak of refractive index (blue line in FIG. 1).

Bioprospecting for Microorganisms that can Release 4MU from Hemicellulose Derivatized on Non-Glycosidic Carbons with 4MU Via Ether Bonds.

General Method

Soil samples were taken beneath sites of wood decay in Maine forests and shaken with a balanced salt solution to suspend soil microbes. Soil and debris were allowed to settle for 10-30 minutes, and the supernatant was decanted. Microorganisms in the supernatant were used directly or pelleted by centrifugation and resuspended in ¹/₂₀ of the original volume of sterile water or balanced salt solution. See Connell, L. et al., Distribution and abundance of fungi in the soils of Taylor Valley, Antarctica. Soil Biol. Biochem., 38:3083-3094 (2006), which is hereby incorporated by reference in its entirety. The suspended microorganisms were inoculated into a sterile minimal medium containing hemicellulose modified via a non-glycosidic ether bond to a lignin or a derivative thereof or a lignin mimic as the major carbon source (for example, Highley's Balanced Salt Solution (HBSS=2 g $KH_2PO_4$, 0.8 g $MgSO_4 \cdot 7H_2O$, 0.1 g $CaCl_2 \cdot 2H_2O$ per liter containing 2 ml per L of trace element mix from American Type Culture Collection (Manassas, Va. 20110), +0.1-1.0% LBG, either benzylated (see below), 4-MU-derivatized, native or a mix). Alternatively or in addition, a modification of a medium formulation that has been used to isolate anaerobic bacteria may be used, modified so as to include, as the major carbon source, hemicellulose derivatized via a non-glycosidic ether bond to a lignin monomer, lignin mimic or derivative thereof. See Warnick, T. A. et al., Clostridium phytofermentans sp. nov., a cellulolytic mesophile from forest soil, Int. J. Syst. Evol. Microbiol. 52:1155-1160 (2002), which is hereby incorporated by reference in its entirety.

Because previous researchers have found that ether bonds are more easily broken at more extreme pH values (see Alexander, M., Biodegradation: problems of molecular recalcitrance and microbial fallibility, Adv. Appl. Microbiol. 7:35-80 (1965), which is hereby incorporated by reference in its entirety), the pH of the media may be adjusted from about pH 4.5 to about pH 5. Each formulation of medium may be incubated as appropriate either aerobically or anaerobically under an oxygen-poor atmosphere (e.g., nitrogen atmosphere). The cultures may be incubated in the dark at room temperature and can be checked at least every week for the development of the products of cleavage of the non-glycosidic ether bond between hemicellulose and lignin or a derivative thereof or a lignin mimic. Fluorescence was measured in a Biotek Synergy 2 plate reader (Biotek Instruments, Inc., Winooski, Vt. 05404) equipped with an excitation filter for 340-380 nm and an emission filter for 440-480 nm.

When cleavage products were detected, culture samples were plated onto agar plates made in the same growth medium as used in the previous step. Once colonies developed, the plates were treated so as to reveal the cleavage product and examined to determine which colonies were cleaving non-glycosidic bonds between hemicellulose and lignin or a derivative thereof or a lignin mimic. Those colonies were picked and replated until 100% of the colonies on the plate were positive and all the colonies had the same appearance under a microscope.

Alternatively, when the extent of cleavage on the non-glycosidic ether bonds to hemicellulose began to decrease in the initial flasks, an aliquot of the culture was diluted 10-fold into fresh medium as before. The extent of cleavage was monitored at least once per week. Typically, fluorescence once again began to rise and eventually to decrease. When it began to decrease, this enrichment process was repeated. On the third or fourth enrichment, a sample of the culture was plated directly onto agar plates made with the growth medium used previously. Individual colonies were examined under an inverted microscope for morphology and growth characteristics. Well separated individual colonies were picked and streaked onto fresh plates. The process was continued until at least 3-4 replicates of each morphology and growth type were obtained. This process is well-known to those skilled in the art.

Because the assay for cleavage of non-glycosidic ether bonds between hemicellulose and lignin or a derivative thereof or a lignin mimic depends on fluorescence, the possibility of endogenous synthesis of fluorescent molecules by the isolated microbial strains was examined. Most simply, strains of microbes isolated as described were grown in liquid suspension cultures in the isolation medium. Once fluorescence had developed, spent medium was sampled and the cells were removed either by centrifugation or filtration through a 0.22μ syringe filter. Fresh substrate for the detection of cleavage of non-glycosidic ether bonds between hemicellulose and lignin or a derivative thereof or a lignin mimic was added to the cell-free medium and the development of fluorescence was monitored over time. A lack of continued increase in fluorescence may be due to the absence of synthesis of autofluorescent compounds, or to the absence of metabolic recharging of required energy or redox co-factors, or to the loss of enzyme activity that was anchored on cell membranes. However, increased fluorescence was interpreted as evidence for the presence of a soluble enzyme activity that may not require an energy or redox cofactor.

Figure 2:
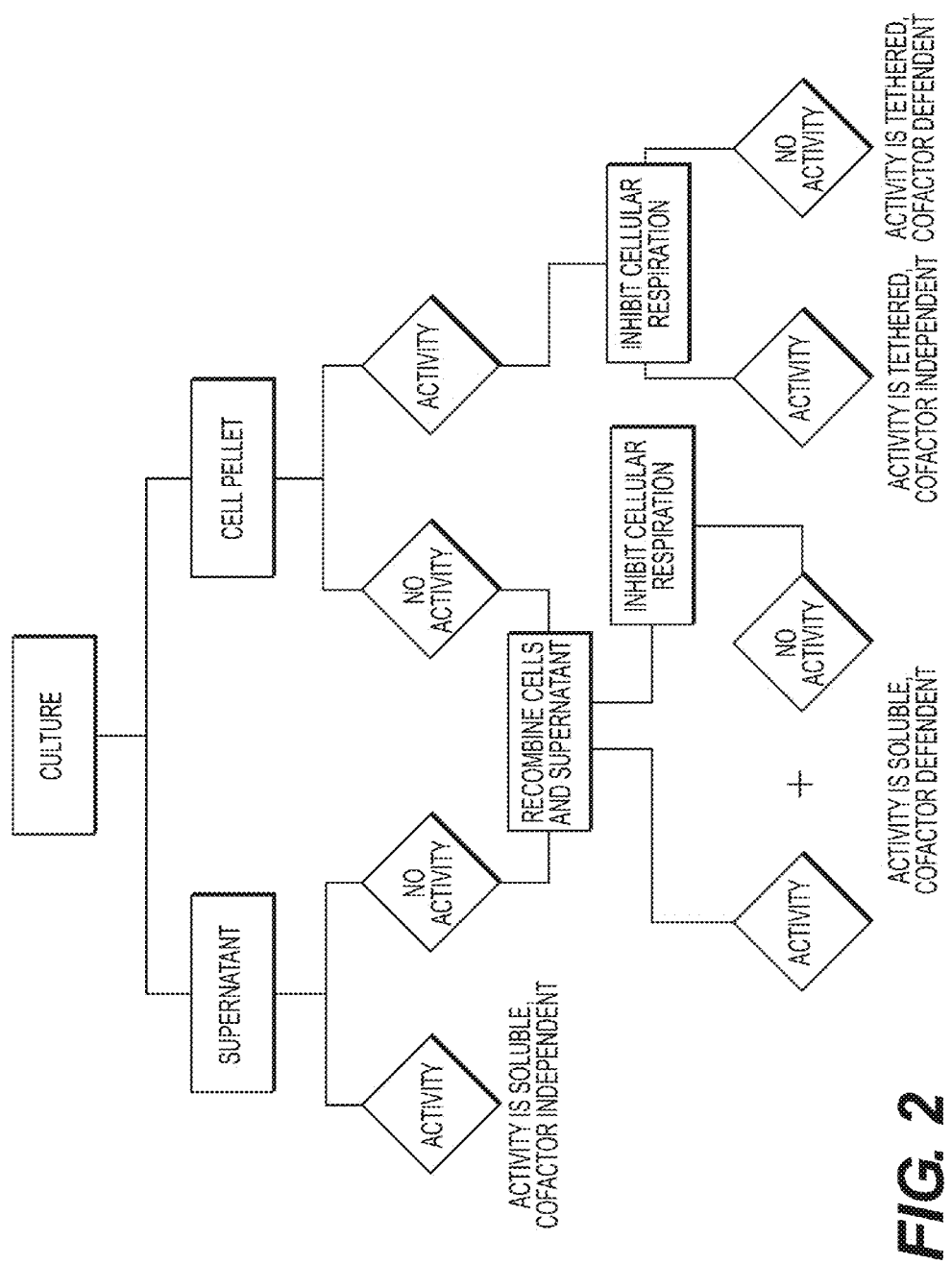
FIG. 2 shows a decision tree for determining if the enzyme activity is soluble, tethered, energy cofactor-dependent or energy cofactor-independent.

In all embodiments, those strains whose enzyme activity was not freely available in the culture medium may be characterized to determine whether the enzyme activity was free in the culture supernatant (soluble or tethered) and whether it used an energy cofactor (energy cofactor-dependent or -independent). The strategy can be summarized in a decision tree as shown in FIG. 2.

Experiment 1—The most effective cellulase systems are not freely secreted but are found tethered to the surface of anaerobic bacteria in a macromolecular structure called a cellulosome. See Chang, M. C Y., Harnessing energy from plant biomass, Curr. Op. Chem. Biol. 11:677-684 (2007), which is hereby incorporated by reference in its entirety. In addition, another enzyme targeting $C_2$ of sugars (2-pyranose oxidase) is tethered to the surface of basidiomycete fungi. See Danneel, H. J. et al., Purification and characterization of a pyranose oxidase from the basidiomycete *Peniophora gigantea* and chemical analyses of its reaction products, Eur. J. Biochem. 214(3):795-802 (1993) and Prongjit, M. et al., Kinetic mechanism of pyranose 2-oxidase from *Trametes multicolor*, Biochem. 48(19):4170-4180 (2009), both of which are hereby incorporated by reference in their entirety. The question of tethered versus free enzyme activity can be answered by separating cells from culture supernatant and challenging the resuspended cell pellet with fresh substrate. Cells that have been heat treated, protease treated, or fixative treated serve as controls. An increase in the concentration of cleavage products relative to controls can be taken as evidence for the presence of tethered enzyme on the washed cells, as long as the time course of generation of cleavage products from substrate is relatively fast. In the event that the activity is slow, the possibility of de novo synthesis of soluble enzyme activity may become significant. An inhibitor of protein synthesis (i.e., chloramphenicol or blasticidin S) may be added to ensure that the cells are not synthesizing and exporting an enzyme activity. Alternatively, the supernatant can be removed from the cells and given a second, separate incubation to see if a soluble activity is present. The latter does not make an a priori assumption that activity against the substrate is due to a protein.

Experiment 2—To test whether any putative enzyme activity uses a cofactor, the cell fraction from Experiment 1 may be treated with an inhibitor of cellular respiration. The final choice of inhibitor depends on the characteristics of the cells (prokaryotic or eukaryotic, aerobic or anaerobic, etc.). For example, the carboxamide antibiotics, directed against succinate dehydrogenase, may affect both bacteria and fungi. Following treatment with the inhibitor, cells can be incubated for 30 minutes to use up endogenous stores of cofactor, and fresh substrate may be added to ensure that the activity is not substrate-limited. The concentration of the cleavage products may be followed over time. If the concentration of cleavage products continues to increase, it can be tentatively conclude that an energy cofactor was not used for activity. In this situation, because cellular energy metabolism is used for protein synthesis, de novo synthesis of enzyme activity may not be a concern.

Experiment 3—To confirm that that a soluble activity uses an energy cofactor, particularly when there is no observable activity in Experiments 1-2, culture supernatant can be combined with either control cells or cells that have been washed and then treated with an inhibitor of cellular respiration. If activity can be restored by exposing inactive culture supernatant to cells that can make energy cofactors, cleavage activity may be presumed to be soluble with a need for an energy cofactor. Incubating culture supernatant with untreated washed cells may serve as a positive control. As before, if the time course of cleavage is slow, a protein synthesis inhibitor may be incorporated into the experiments.

Example 3

Soil samples were collected from beneath thoroughly rotted softwood and placed in sterile containers and were returned to the laboratory as quickly as possible. Fifty grams of soil was combined with 100 ml of sterile Highley's Balanced Salt Solution. The mixture was shaken gently at room temperature for 1 hour. Soil was permitted to settle for 10-30 minutes and the supernatant was decanted. Microorganisms in the supernatant were pelleted by centrifugation and resuspended in 1/20 of the original volume of sterile water. See Connell, L. et al., 2006, supra. One ml of the soil supernatant was inoculated into 10 ml of sterile culture medium in sterile 25 ml Erlenmeyer flasks. The culture medium consisted of HBSS supplemented with 2 g/L of ammonium nitrate and 0.3% 4MU-LBG. One flask was inoculated with sterile HBSS to serve as a non-inoculated control. The cultures were incubated at room temperature in the dark. At weekly intervals, 0.1 ml was withdrawn from each culture into a black 96 well plate. About 0.1 ml of 0.3M sodium borate, pH 9.8-10 added to intensify the fluorescence. Fluorescence was measured in a Biotek Synergy 2 plate reader (Biotek Instruments, Inc., Winooski, Vt. 05404) equipped with an excitation filter for 340-380 nm and an emission filter for 440-480 nm. The fluorescence was compared to that measured for non-inoculated control medium.

Over the course of 3-6 weeks, fluorescence developed in some of the flasks. When fluorescence began to decline, a sample of the culture was spread onto sterile petri dishes containing fresh medium solidified with 0.16% agar. When colonies developed, plates were examined using a hand-held UV light to note which colonies were fluorescent. Alternatively, a PVDF (polyvinylidene difluoride) membrane was overlaid on the plates. 4MU binds strongly to PVDF. The membrane was removed and rinsed pH 8-10 to intensify 4MU fluorescence. Fluorescence spots on the membrane were correlated to colonies on the plate. Fluorescent colonies were picked and re-spread on new plates. The process was repeated until pure cultures were obtained.

Putative positive colonies were grown in suspension cultures in the medium originally used for isolation (HBSS+ammonium nitrate+4MU-LBG). Spent culture medium was passed through a sterile filter to remove cells and fresh 4MU-LBG was added. If additional fluorescence developed, the culture was considered to be producing and exporting an enzyme that liberated 4MU from the substrate. If not, it was concluded that either:

a) the cells in the culture were producing an autofluorescent molecule, and once the cells were removed, no additional fluors could be synthesized; b) the enzyme was located on the cell surface (cellulosomal); or c) the enzyme required the on-going presence of an energy cofactor that required cellular metabolism to produce. Two or more of these explanations could be present simultaneously.

Autofluorescence was eliminated in two different ways. First, it was presumed that any fluorescent molecules synthesized by the cells would have different spectral characteristics than 4MU. Consequently, emission and excitation wavelength scans of spent medium were performed. Interference by contaminants in the LBG preparation rendered these tests inconclusive in some cases.

Alternatively, to eliminate false positives due to autofluorescence, the cells were grown in the presence of an enzyme substrate that would not yield fluorescence. A benzylated derivative of LBG was synthesized based on a method developed by Lu. See Lu, Y., Benzyl konjac glucomannan, Polymer 43:3979-3986, (2002), which is hereby incorporated by reference in its entirety.

Synthesis of Benzylated Locust Bean Gum (LBG), 10 Gram Scale

The synthesis of benzylated LBG, as illustrated in FIG. 3, was performed as follows:

(1) Locust bean gum (10 gm) was dissolved in 400 ml pure water with overhead stirring at 200 rpm. Tetrabutyl ammonium iodide (250 mg) was added to act as a phase transfer catalyst. The temperature was maintained at 40-45° C. with stirring for 1 hour.

(2) 100 grams of 40% (w/v) aqueous NaOH was added dropwise to the reaction mixture. The temperature was maintained at 40-45° C. with stirring for an additional hour.

(3) Approximately 25 ml benzyl chloride was added dropwise and the mixture was stirred overnight at 90° C.

(4) The reaction was cooled to room temperature and neutralized with acetic acid, leading to some precipitation of the benzylated material.

(5) Complete precipitation was accomplished by the addition of 300 ml of ethanol dropwise with stirring to a final concentration of ~60% (v/v).

(6) The benzylated LBG was filtered through P8 filter paper on a water aspirator. The precipitate was washed in a beaker with ~300 ml of 95% ethanol, added dropwise while stirring, and then stirred at room temperature for 1 hour.

(7) The washed precipitate was recovered by filtration as before and washed with 95% ethanol as before an additional two times.

(8) The final precipitate was dried on the aspirator for 30 minutes and then dried in an oven at ~70-75° C. overnight to yield a white and fluffy powder.

(9) The final product was stored at −20° C.

An aliquot of a putatively positive microbial strain was inoculated into each of two parallel suspension cultures. One flask's sole carbon source was LBG mixed with benzylated LBG. The second flask's sole carbon source was LBG mixed with 4MU-LBG. The total concentration of LBG+modified LBG was 0.3%, but the concentration of the modified LBG, whether benzylated or 4-methylumbelliferone-derivatized, ranged from 0.05% to 0.3%. The concentration of the modified LBG was kept consistent within a single experiment. If fluorescence that developed in the culture containing 4MU-LBG was significantly higher than the fluorescence developed in the culture containing benzylated LBG, it was presumed that the difference was due to the liberation of 4MU by enzymatic activity.

Microbial strains that synthesized a putative soluble and co-factor independent activity were identified by both fatty acid methyl ester analysis and by rDNA sequencing.

Example 4

Soil microorganisms were collected and incubated as in Example 3. However, when fluorescence of the primary cultures began to decline, 1 ml of the culture was inoculated into 10 ml of fresh medium. The new cultures were incubated as before, at room temperature in the dark without shaking, and the culture supernatant monitored as before by sterilely withdrawing an aliquot of culture supernatant, adjusting its pH to about 9.8, and comparing fluorescence to that of a non-inoculated control culture. This enrichment process was repeated 3-4 times.

After the 3rd and 4th enrichments, samples of the culture medium were plated onto HBSS+ammonium nitrate+0.3% LBG+0.16% agar. Plates were incubated at room temperature and examined daily to determine the numbers and morphologies of the colonies present. Several colonies for each morphology found were individually picked into fresh liquid medium and resuspended. Each enriched culture yielded about 15-30 colony types.

Each individual colony suspension was replated individually. Each plate was examined for purity, and colonies re-picked. The process was repeated until all the different isolates were pure. Frozen stocks were made for each colony.

Each individual freezer stock was inoculated into a suspension culture in which the growth medium's sole carbon source was LBG mixed with 4MU-LBG. However, in some cases, additional sources of organic nitrogen like yeast extract or malt extract were also added, adding a small amount of additional carbon source. The total concentration of LBG+modified LBG was 0.3%, but the concentration of the 4MU-LBG ranged from 0.05% to 0.3%. The concentration of the modified LBG was kept consistent within a single experiment. The culture supernatant was monitored at least twice weekly for the development of fluorescence as previously described. Cultures that developed fluorescence were further screened for autofluorescence by one of the methods as described in Example 3.

For both Examples 3 and 4, microbial strains that synthesized a putative soluble and co-factor independent activity were selected and identified by both fatty acid methyl ester analysis and by rDNA sequencing. In some cases, fatty acid methyl ester analysis was not performed and two independent rDNA sequence analyses were performed.

Figure 4:
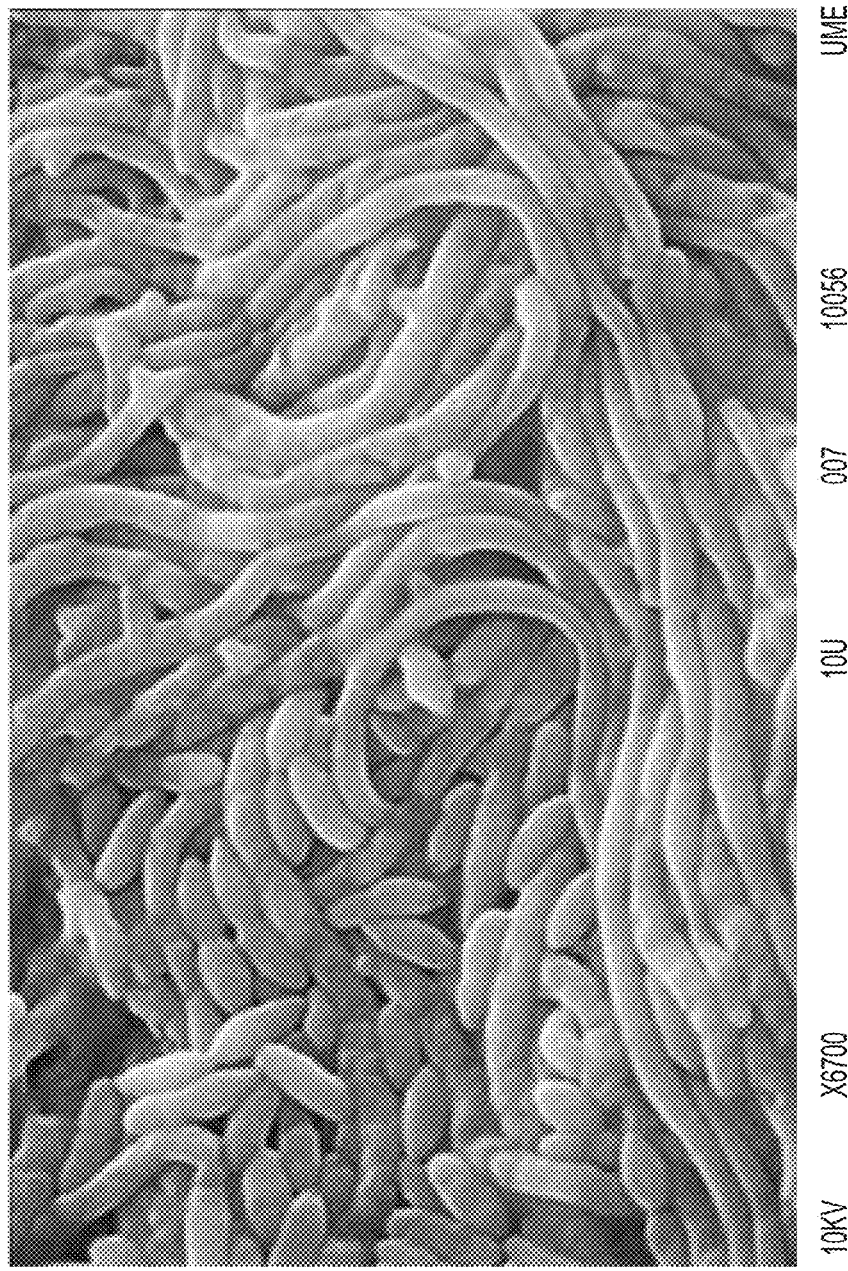
FIG. 4 shows the scanning electron micrograph of strain B603.

A novel bacterial strain, B603, was isolated. Fatty acid methyl ester analysis indicated an excellent (similarity index/standard deviation of 0.396) match to *Xanthomonas axonopodis vasculorum*. rDNA analysis indicated a 100% match to *Luteibactor rhizovicina* (strains 1176, 1196, and 1199) as well as some *Dyella* species. See Stark, M. et al., MLTreeMap—accurate Maximum Likelihood placement of environmental DNA sequences into taxonomic and functional reference phylogenies, BMC Genomics 11:461 (2010), which is hereby incorporated by reference in its entirety. It is believed that B603 is closely related to *Luteibactor rhizovicinus*. A scanning electron micrograph is shown in FIG. 4.

Example 5

A novel microorganism that can release 4MU from xylan derivatized on non-glycosidic carbons with 4MU via phenolic ether bonds.

A fluorogenic substrate analogous to 4MU-LBG was constructed based on a commercial xylan prepared from birchwood. Unlike mannan, xylan is based on a 5 carbon sugar, xylose. Derivatization of chains of hexoses in the pyranose configuration can take place at a primary hydroxyl. However, in xylan, the chains of 5 carbon sugars in the pyranose configuration lack primary hydroxyl groups for derivatization. Derivatization, therefore, may be at a secondary hydroxyl, a more difficult challenge energetically. In addition, the carbons with secondary hydroxyls, $C_2$ and $C_3$ of xylose, are anomeric. Depending on the mechanisms of derivatization steps, the stereoconfirmation of the xylose residue may be altered, changing the nature of the sugar residues.

A more conventional method of derivatization was devised to avoid changing the stereoconfirmation and to overcome the lower reactivity of the secondary hydroxyl groups.

Step 1: Controlled hydrolysis of xylan. The length of the xylan polymer affects solubility in the solvents needed for the synthesis. A controlled hydrolysis at pH 3 was used to increase xylan's solubility in DMSO and pyridine. Approximately 10 g of xylan from birchwood (Sigma Cat. No. X0502) was placed into a beaker containing 250 mL water (adjusted to pH=3 using glacial acetic acid). The solution was autoclaved for 100 min at 130° C. After autoclaving, the material was neutralized with 3-10 M sodium hydroxide and lyophilized overnight. The xylan was then washed by stirring it with ethanol for 60 minutes followed by filtration through P8 paper at room temperature. The wash was repeated. The residue was dried under vacuum and then lyophilized.

Step 2: Glycosylation. Free glycosidic hydroxyls were methylated by refluxing the xylan in dry methanol. The xylan was then dissolved in 100 ml hot water, and precipitated by adding 200 ml 95% ethanol (dropwise), and filtered using P8 filter paper. The precipitate was oven dried overnight at 70° C. Xylan was then quickly transferred to a 200 ml RB (round bottom) flask pre-flushed with $N_2$ and fitted with an air cooling condenser. A solution of 1 ml of conc. HCl in 25 ml of anhydrous methanol was transferred to the reaction flask. The reaction was stirred at reflux temperature (~85° C.) overnight. The reaction was cooled down in an ice bath for ½ h and then filtered through P8 filter paper. The precipitate was dissolved in 50 ml of water and neutralized using $NaHCO_3$. The xylan was reprecipitated with 100 ml of ethanol and the precipitate was separated by filtration through P8 filter paper and dried at 70° C. overnight.

Step 3: Benzylation. The residue was placed into a dry RB flask (flushed with nitrogen), followed by the addition of dry DMSO (210 mL). The mixture was stirred at 70° C. for 3 h, cooled to room temperature, and then powdered potassium hydroxide (9 mol KOH per mol OH group) was added. A catalytic amount of crown ether (benzo-18-crown-6) was added to the mixture. The mixture was stirred overnight at 50° C. An ice bath was used to cool the mixture down to 0° C., followed by dropwise addition of benzyl bromide (3 mol benzyl bromide/mol OH group) through a septum. After 15 minutes, the temperature was increased to 70° C. and the mixture was stirred overnight. The mixture was cooled in an ice bath, methanol (500 mL) was added to precipitate the polysaccharide, and the xylan was separated by filtration though a P8 filter paper. The precipitate was washed at least twice in methanol, ethanol or acetone. The wash could be on filter paper, or with resuspension in a beaker with or without stirring and at room temperature or up to 70° C. followed by filtration through P8 paper. Sometimes the xylan was resuspended in water and neutralized, followed by precipitation and drying or lyophilization.

Step 4: Triflation. The benzylated xylan was added to a dry RB flask that was flushed with nitrogen. Pyridine (3 mL) was added to the flask and the solution stirred for 30 min at 60° C. The reaction mixture was cooled to room temperature, then to 0° C. using an ice bath, and finally to −20° C. with an isopropanol bath (stored at −80° C.). Triflic anhydride (1-2 mL) was carefully added to the solution. The reaction was stirred for 15 min at −20° C., then at room temperature overnight. The mixture was frozen at −80° C., and subsequently lyophilized. Ethanol (95%) was used to wash the residue for 15-30 min. The mixture was filtered through P8 paper, then the residue dried over vacuum for 15 min, and finally lyophilized.

Step 5: Bromination. The triflated material was placed into a dry RB flask and an air condenser was attached to the flask. Dioxane (100 mL) was added to the flask, and nitrogen was used to purge the system of moisture. Dry tetra-n-butylammonium bromide (10.65 g) was added through the septum on the condenser. The mixture was refluxed at 105° C. for 24 h, cooled to room temperature, frozen and finally lyophilized. Ethanol (300 mL) was added to the residue and the mixture was stirred for 1 h. The mixture was filtered and the residue was washed two more times, followed by lyophilization.

Step 6: Addition of 4-MU. 4-MU was added to a dry RB flask followed by addition of dry DMSO (25 mL). The flask was placed into an ice bath and sodium hydride (0.5 g) added dropwise. The flask was purged of moisture using nitrogen. The reaction was allowed to stir for 30 min, followed by the addition of the brominated xylan. The reaction was stirred overnight. Ethanol (100 mL) was added slowly to the flask at 0° C. The suspension was filtered, and the precipitate was washed three times with ethanol and lyophilized. The preparation of xylan derivatized with 4MU was qualified by similar experiments to those used on derivatized LBG, including digestion with commercially available α- and β-xylosidases.

For bioprospecting using xylan derivatized with 4MU, soil samples were taken beneath sites of well-rotted hardwood in Maine forest. As described above, the soil was shaken with a balanced salt solution to suspend soil microbes. Soil and debris were allowed to settle for 10-30 minutes, and the supernatant was decanted. Optionally, the supernatant may be diluted. See Connell, L. et al., 2006, supra. The suspended microorganisms were inoculated into a sterile minimal medium (HBSS containing 2 ml/L of trace element mix from American Type Culture Collection, +0.1-1.0% birchwood xylan (Sigma Cat. No. X0502) as the sole or major carbon source. The xylan was either 4-MU-derivatized, native, benzylated (xylan prepared for derivatization with 4MU, but the preparation stopped after benzylation [see Step 3 above]) or a mix. In addition, a modification of a medium formulation that has been used to isolate anaerobic bacteria was used. See Warnick, T. A. et al., 2002, supra. However, because previous researchers have found that ether bonds are more easily broken at more extreme pH values, the pH of the media was adjusted to pH 4.5-5. See Alexander, M., (1965), supra. Each formulation of medium was incubated both aerobically and anaerobically under a nitrogen atmosphere. The cultures were incubated in the dark at room temperature and checked every week for the development of fluorescence.

When fluorescence developed and began to decrease in the initial flasks, 1 ml of culture was diluted into 10 ml of fresh medium as above as an enrichment step. The fluorescence was monitored at least once per week. Typically, fluorescence once again began to rise and eventually to decrease. When fluorescence began to decrease, the enrichment process was repeated. Concurrently with each enrichment step, a sample of the culture was plated directly onto agar plates made with the growth medium described above but using xylan instead of 4MU-xylan. Individual colonies were examined under an inverted microscope for morphology and growth characteristics. Well separated individual colonies were picked and streaked onto fresh plates. The process was continued until at least 3-4 replicates of each morphology and growth type were obtained. Each isolate was then grown under the same conditions as in the enrichment flasks to see if fluorescence developed. Those isolates that did not develop fluorescence were discarded.

Any fluorescence that developed in cultures of the isolated colonies could have been due to generation of 4MU from the substrate and/or to autofluorescence. To eliminate those colonies that were merely autofluorescent and did not generate 4MU from the substrate, strains of isolates were grown in liquid suspension cultures in the isolation medium. Once fluorescence had developed, spent medium was sampled and the cells were removed either by centrifugation or by filtration through a 0.22µ syringe filter. Fresh 4MU-derivatized xylan (4MU-X) was added to the cell free medium and the development of fluorescence was monitored over time. A lack of continued increase in fluorescence could be due to the absence of synthesis of autofluorescent compounds, or to the absence of metabolic recharging of required energy or redox co-factors, or to loss of enzyme activity anchored on cell membranes. Increased fluorescence was interpreted as evidence for the presence of a soluble enzyme activity that did not require an energy or redox cofactor.

Surprisingly, 12 prokaryote strains and 1 mycelial fungus were isolated whose cell-free culture supernatant could release 4MU from 4MU-X. Some of the 12 prokaryotes were closely related to one another. For example, three prokaryotes were different *Paenibacillus* strains, and two isolates were different *Burkholderia* strains. One of the *Paenibacillus* strains, E518, was more extensively studied. Its rDNA sequence's closest homologies were *Paenibacillus* sp. Y412MC10, *Paenibacillus polymyxa*, and *Paenibacillus terse* HPL-003.

Novel Enzymes that Cleave Non-Glycosidic Bonds Between Hemicellulose and Lignin or Derivative Thereof or a Lignin Mimic The activity that cleaved non-glycosidic phenolic ether bonds between lignin and mannan from B603 and the activity that cleaved non-glycosidic phenolic ether bonds between lignin and xylan from E518 were shown to be due to proteinaceous enzymes by a pre-digestion of the culture supernatants with proteases. The incubation with protease destroyed activity for both B603 supernatant and E518 supernatant. An example of a protease digestion experiment is shown in Table II for B603. These results were repeated with multiple different proteases for both B603 and E518 supernatants.

TABLE II

Effect of *S. griseus* protease on HLE activity

| Substrate | Percent Relative to Control-Untreated | Percent Relative to Control-Protease Treated |
|---|---|---|
| Fluorogenic model substrate 1 | 100% | 19.8% |
| Fluorogenic model substrate 2 | 100% | 21.4% |

Culture supernatant from B603 was filtered through 0.45µ filters to remove cells and incubated with 2 different preparations of fluorogenic model compound for 24 hrs at 24° C.
Numbers shown are the averages of the two replicates.

The activity isolated from B603, is referred herein as MLE (mannan:lignin etherase). MLE is the only enzyme known to cleave 4MU from 4MU-LBG. Glycosidases that have been tested against 4MU-LBG and do not release 4MU are listed in Table III.

The activity isolated from E518, is referred herein as XLE, (xylan:lignin etherase). XLE is the only enzyme known to cleave 4MU from 4MU-xylan (see Table III). Similarly, none of the carbohydrate-active enzymes tested released 4MU from 4MU-xylan. MLE also does not release 4MU from 4MU-xylan.

TABLE III

Effect of Various Carbohydrate-Active Enzymes on 4 MU-LBG and 4 MU-Xylan

| Enzymes Unable to Cleave 4 MU from either 4 MU-LBG or 4 MU-Xylan | Enzymes Able to Cleave4MU from 4 MU-LBG |
|---|---|
| Cellulase from *Trichoderma reesei* ATCC 26921 | MLE |
| Hemicellulase from *Aspergillus niger* | |
| Isoamylase from *Pseudomonas* sp. | Enzymes Able to Cleave 4 MU from 4 MU-Xylan |
| Pullulanase from *Klebsiella pneumoniae* | |
| Xylanase from *Thermomyces lanuginosus* | XLE |
| α-Amylase from *A. oryzae* | |
| α-Galactosidase from green coffee beans | |
| α-Mannosidase from *Canavalia ensiformis* | |
| β-Galactosidase from *Aspergillus oryzae* | |
| β-Mannosidase from *Helix pomatia* | |
| β-Xylosidase (CAZyme Xylosidase 1) | |

For all the enzymes listed in Table III, control experiments with commercially available substrates were tested in parallel to confirm that the enzymes were active and that the experimental conditions were consistent with activity of the enzymes. Where conditions permitted, internal controls were used, as previously shown and discussed in Table I.

Table IV lists some of the glycosidase substrates tested with MLE under conditions in which MLE is known to be active (pH 5-5.5, 50-150 mM ionic strength, 30° C., presence of a trace mineral supplement). Each substrate was shown to be cleavable by a known enzyme in parallel to the MLE digestion. In addition, every experiment included a parallel experiment in which the MLE preparation was tested against 4MU-LBG to ensure that the MLE used was active.

TABLE IV

Effect of MLE on Various Glycosidase Substrates

| Substrates Unaffected by MLE | Substrates Cleaved by MLE |
|---|---|
| Hydroxyethylcellulose dyed with Ostazin red | 4 MU-LBG |
| 4-O-Methyl-D-glucurono-D-xylan-Remazol blue | |
| Glycogen azure | |
| Azo-carob galactomannan | |
| Carboxymethyl cellulose | |
| 4-Methylunbelliferyl-β-D-lactoside | |
| 4-Methylumbelliferyl-α-D-mannopyranoside | |
| 4-Methylumbelliferyl-β-D mannopyroside | |
| 4-Methylunbelliferyl-β-D xylopyranoside | |
| 4 Nitrophenyl-α-D-mannopyranoside | |
| 4 Nitrophenyl-β-D-mannopyranoside | |
| p-Nitrophenol-β-D-glucopyranoside | |
| Starch Azure | |
| 4-Methylunbelliferyl-β-D xylan | |

Recombinant MLE (rMLE) also shows activity against native cellulosic biomass (see below).

Since the activity of MLE is novel, there was no available genetic or protein probe to use to isolate the gene of interest from B603. The gene was cloned based on its encoded enzyme's activity against the macromolecular substrate, 4MU-LBG. Because 4MU-LBG is a mix of very large macromolecules, there was little likelihood that it would be able to enter the cells and encounter recombinant enzyme once it was expressed in a cloning host such as *Escherichia coli*. Consequently, a bacteriophage lambda cloning system was chosen. Bacteriophage lambda causes extensive cell lysis, releasing the recombinant protein into the surrounding medium, where it can come into contact with its potential substrate, 4MU-LBG.

A cDNA library was prepared from B603 mRNA isolated from cells that were expressing the enzyme. To obtain the mRNA, B603 cells were grown in medium containing 4MU-LBG as the sole carbon source (see above for complete medium composition). At times bracketing the usual expression times for MLE, approximately 200 ml of cells were harvested and samples of the culture supernatant were assayed for MLE activity. Because assay for MLE activity takes at least 24 hours, RNA was prepared at all time points, and those preparations of RNA from cells which were not expressing MLE were discarded. Total RNA was prepared using Ribo-Pure kit for bacteria from Ambion (now Life Technologies, Grand Island, N.Y. 14072). Briefly, cell walls were disrupted by mixing cells with an RNase inhibitory solution, and vortexing them with zirconia beads. The lysate was then extracted with chloroform to yield an upper aqueous phase that contained the RNA. The RNA was further purified by dilution with ethanol and bound to a silica filter followed by an aqueous, low ionic strength elution. The RNA was stored frozen at −80° C. until needed. In some cases, the cell pellets were frozen in liquid nitrogen, stored at −80° C., and the RNA extraction was performed at a later time point. RNA preparations or frozen cell pellets from time points at which no MLE activity was detected in culture supernatants were discarded. Quality of the RNA preparation was checked by gel electrophoresis.

The 16S and 23S rRNA background was reduced using the MICROBExpress™ Bacterial mRNA Enrichment Kit from Ambion (now Life Technologies, Grand Island, N.Y. 14072) following manufacturer's directions. The kit contained magnetic beads derivatized with oligosequences complementary to conserved regions of 16S and 23S prokaryotic ribosomal RNA. A large part of the rRNA in the B603 RNA preparation hybridized to the beads and was removed from the solution, enriching the preparation for mRNA. The purified mRNA was reverse-transcribed using random primers and ligated into the XhoI-EcoR1 site of Lambda-ZAP II according to manufacturer's directions (Stratagene, now Agilent Technologies, Santa Clara, Calif. 95051). The titer of the library was measured as recommended by the manufacturer.

An aliquot of the λ library was plated onto a lawn of XL1-Blue *E. coli* according to manufacturer's directions (Stratagene, now Agilent Technologies, Santa Clara, Calif. 95051) except that 4MU-LBG (0.25% w/v) which had been briefly treated with a commercial hemicellulase was incorporated into the top agarose. Once plaques were visible in the top agarose, the plates were overlaid with PVDF membranes that had been wetted in methanol and rinsed in sterile Highley's buffer to remove the methanol. The lifts were rinsed briefly in 0.1M borate buffer, pH 9.0 to intensify the 4MU fluorescence and examined under shortwave UV light.

The plaques corresponding to the fluorescent spots on the filter paper were excised as agarose plugs, and the phage contained in the plugs were eluted into SM (0.1M NaCl, 8 mM MgSO$_4$, 50 mM Tris, pH 7.5). The eluted phage were replated and rescreened as before until all plaques on the plate were fluorescent in the plaque lift assay. An additional round of plating, screening, and picking of an isolated plaque from the putatively purified phage clone was performed to guarantee purity. Individual fluorescent plaques were selected from the final pure plate and eluted from the top agarose into SM with 50% glycerol to create a freezer stock. Each freezer stock was used to create plasmids in BlueScript using LambdaZapII's autosubcloning feature according to manufacturer's directions (Stratagene, now Agilent Technologies, Santa Clara, Calif. 95051). Several well separated colonies of *E. coli* containing the plasmids were used to create independent freezer stocks for each putative positive. See Sambrook et al., 1989, supra.

Some false positives were eliminated by testing the phage stocks for inducible expression. Each independently cloned phage stock was plated onto an *E. coli* lawn in the absence of fluorogenic substrate, allowed to grow overnight and lifted onto PVDF membrane as before. Plaque lifts were rinsed with 0.1M borate buffer, pH 9, dried, and examined under short-wave UV light. Those phage preparations that were strongly positive in the absence of a fluorogenic substrate were tentatively considered to be false positives. Sequence analysis of the false positives was performed using primers based on the T3 and T7 sites of the Bluescript vector. Most of the false positives were clearly ribosomal DNA, probably resulting from rRNA that was not removed during the mRNA enrichment. These inserts had no significant open reading frames and appeared to fortuitously produce short peptides that had some intrinsic fluorescence. Other false positives also appeared to produce short fluorescent peptides.

The phages from the remaining positives were amplified in broth culture, and supernatant from the lysates was filtered and incubated with 4MU-LBG to determine whether activity against the substrate was present. Those clones without activity against the substrate were discarded.

The phagemids from positive lambda isolates were excised from the rest of the lambda DNA and transformed into SOLR cells using the ExAssist helper phage, following the manufacturer's protocol (Stratagene, now Agilent Technologies, Santa Clara, Calif. 95051). The cells harboring the excised phagemids were plated, and single, well-isolated colonies were picked for characterization. 5 to 10 individual colonies were picked from each plated excision. Each colony pick was amplified in broth and the plasmids extracted using the Genecatch Plus Plasmid Miniprep Kit (Epoch Life Science, Sugar Land, Tex. 77496). The plasmids were digested with KpnI, and EcoRI/KpnI (Promega Corporation, Madison, Wis., 53711), and the bands separated by gel electrophoresis to confirm that all of the inserts in the phagemid were the same for each particular isolate. The size of the insert was also estimated from the gel at the same time.

Once it was certain that an isolate was a pure culture, a second activity confirmation was carried out. The cells were grown, and induced with IPTG (isopropylthiogalactoside) following the manufacturer's protocol (Stratagene, now Agilent Technologies, Santa Clara, Calif. 95051). The cells were lysed by sonication and the cell lysate was used in an activity assay against 4MU-LBG.

Ultimately, a subclone (clone 17-2) of a single plaque from the library screen was isolated that had an IPTG inducible activity against 4MU-LBG and an insert size of approximately 800 bp. The sequence of the positive insert was determined by sequencing the phagemid with standard T3/T7 primers. The sequences from the forward and reverse primers were read using Chromas (Technelysium Pty Ltd, South Brisbane QLD 4101, Australia) or Geneious 5.0 (Biomatters Inc. San Francisco, Calif. 94107) software, and a consensus sequence was generated. The ~800 bp insert contained an open reading frame of 582 bp, corresponding to a 193 amino acid peptide with a calculated pI of 5.97. The nucleotide sequence (SEQ ID NO:3) and translated amino acid sequence (SEQ ID NO:4) of the open reading frame are both shown in FIG. 5. Since there was no identifiable ribosome binding site or −10 sequence, it was concluded that the cDNA encoded an active fragment of the complete polypeptide. As shown in FIG. 6, the nucleotide sequence of the gene fragment from the phagemid (SEQ ID NO:3) showed 75% identity with the nucleotide sequence of a glycogen debranching enzyme from Burkholderia glumae BGR1 (SEQ ID NO:5).

Genomic DNA was extracted from B603 strain using the cetyltrimethyl ammonium bromide (CTAB) method with multiple phenol extractions. See Ausubel, F. et al., Short Protocols in Molecular Biology, Wiley and Sons, NY (1995), which is hereby incorporated by reference in its entirety. The genomic DNA was digested with a panel of restriction endonucleases and the digests were electrophoresed on agarose gels. Biotin-labeled probe to clone 17-2 was prepared by PCR using a kit from Jena Bioscience GmbH (D-07749 Jena, Germany) according to manufacturer's directions. The probe was prepared using primers G3-1 and G3-2 (see Table V), resulting in a 558 bp biotinylated oligonucleotide, which was separated from unincorporated nucleotides using a PCR purification kit (Promega Corporation, Madison, Wis., 53711), again according to manufacturer's instructions. A Southern blot analysis using the biotinylated probe indicated that the gene corresponding to clone 17-2 is single copy and is contained in an EcoR1 fragment of approximately 6-7 kb (FIGS. 7A and 7B). See Ausubel, F. et al., 1995, supra.

"Walking" and genomic cloning strategies were used to obtain the complete gene sequence (see SEQ ID NO:1), along with the 5' and 3' untranslated regions of the cDNA. Primers were designed to regions just upstream of the translation start site and downstream of the stop signal. The OligoCalc oligonucleotide properties calculator was used to determine primer fitness. See Kibbe, W. A., OligoCalc: an online oligonucleotide properties calculator, Nucl. Acids Res., 35(2):W43-W46 (2007), which is hereby incorporated by reference in its entirety. The primers that were used to determine the sequence are listed in Table V.

TABLE V

Primers for Sequencing the MLE Gene and Its Surrounding Gene Regions

| Name | Specificity | Sequence (5' to 3') | SEQ ID NO. |
|---|---|---|---|
| G3-1 | upstream clone | AGCTGCGATCGCCACGAGGGTGAAGCGCGCCAT | 8 |
| G3-2 | downstream clone | GTGCGTTTAAACTGCCGGTTCGGTCCGGACAAT | 9 |
| G3-3 | 161 internal | GGAGCTGACCGACTTCGTGGCGCGGCTGG | 10 |
| G3-4 | 161 reverse | CCAGCCGCGCCACGAAGTCGGTGAGCTCC | 11 |
| G3-5 | 281 internal | AGGTGGCATGGTTCGACGAGAGTGG | 12 |
| G3-6 | 281 reverse | CCACTCTCGTCGAACCATGCCACCT | 13 |
| G7 | G7 upstream reverse | CGTTGGCGTCGTTGTGTTTGTCGTTGT | 14 |
| G8 | G8 upstream reverse | CTTCGCCGTTGGCGTCGTTGTGTTTGTCG | 15 |
| G9 Biotin | G9 biotin internal Southern probe | GCGACGCCCGAGACCCATGTGTTC | 16 |
| Sac1.7P1F | primer for walk | GGGCAATGTCGAGATCG | 17 |
| Sac1.7P1R | primer for walk | TTCTCCACCGGCAGGG | 18 |
| F − 519 | upstream forward primer | GATCACCAGCGGCGAAAGCCCT | 19 |
| R − 519 | upstream reverse complement of −519 | AGGGCTTTCGCCGCTGGTGATC | 20 |
| F + 718 | downstream forward primer | GATCGCGCAGTTTCCCGGTGAG | 21 |
| R + 718 | downstream reverse complement of 718 | CTCACCGGGAAACTGCGCGATC | 22 |
| F + 1205 | downstream forward primer | CGACGACTTCCACAATGCGCTGCAC | 23 |
| R + 1205 | downstream reverse primer | GTGCAGCGCATTGTGGAAGTCGTCG | 24 |

TABLE V -continued

Primers for Sequencing the MLE Gene and
Its Surrounding Gene Regions

| Name | Specificity | Sequence (5' to 3') | SEQ ID NO. |
|---|---|---|---|
| Fminus474 | upstream forward primer | GCGCACGACGGCTTCACGCTG | 25 |
| Rminus474 | upstream reverse primer | CAGCGTGAAGCCGTCGTGCGC | 26 |
| cc148R | upstream reverse primer HLE | GCTCGGGCGCGAAGAAGGCAAGCGTG | 27 |
| 2A1bF671 | 2A1 from F993 middle of seq | CTGCGAGGCAAGGATAACGAAGAGC | 28 |
| 4A5bF600 | 4A4 from R849 middle of seq forward | CAAGCCATGCACGCCGGGATACCG | 29 |
| hle2up554 | middle of cc148R seq upstream HLE | CATGTTCATAGCCGACTGACGAGGAAATC | 30 |

As described above, genomic DNA has been shown by Southern blotting to contain an EcoR1 fragment of 6-7 kB that contains the MLE gene (FIG. 7B). For genomic cloning, a large Eco R1 digest of genomic DNA was electrophoresed on a preparative gel and the band region between 6 and 7 KB was excised. The DNA was purified using a Gene Jet Gel extraction kit (Thermo Fisher Scientific, Inc., Waltham, Mass. 02451) and the purified DNA was ligated into pUC19. The plasmids were transformed into an *E coli* host, and the transformants were diluted and spread on 150 mm petri dishes. Once the colonies were grown, they were overlaid with sterile Hi-Bond N membranes (Amersham). The adherent cells were lysed in situ using 0.5N NaOH, neutralized with 1M Tris-HCl, pH 7.5 and washed in 0.5 M Tris-HCl, pH 7.5, 1.25M NaCl. See Ausubel, F. et al., 1995, supra. DNA on the membranes was cross-linked to the membranes with short-wave UV light. The blots were processed as for Southern blots using a probe prepared by PCR from genomic DNA using primers G3-1 and G3-2 (see Table V) and a kit from Jena Bioscience GmbH (D-07749 Jena, Germany) according to manufacturer's directions. The PCR resulted in a 558 bp biotinylated oligonucleotide that was separated from unincorporated nucleotides using a PCR purification kit (Promega Corporation, Madison, Wis., 53711), again according to manufacturer's instructions. Areas of the blots reacting with biotinylated probe was detected with streptavidin-conjugated to alkaline phosphatase and visualized with nitroblue tetrazolium and 5-bromo-4-chloro-3-indolyl phosphate. See Ausubel, F. et al., 1995, supra. Colonies corresponding to purple spots were excised and replated until 100% of the colonies on the plate were positive when a membrane overlay of the plate was reacted with the probe. Then a single well-separated colony was chosen as a stock. The presence of the insert was confirmed by PCR with relevant primers. Several independent genomic clones containing an insert were isolated and sequenced.

Once plasmids containing the desired gene region were purified, the upstream and downstream regions were sequenced by "walking" New primers were made based on the known gene sequences to sequence upstream and downstream from the known region, as discussed above (see Table V). When the new regions were sequenced, new forward and reverse primers were designed to amplify more upstream or downstream gene region, as well as read back to the previously known region to confirm the sequence. The upstream and downstream gene regions of the MLE gene are shown in FIGS. 10A and 10C and designated as SEQ ID NOS:6 and 7, respectively.

DNA sequences determined from clones and from walking experiments were proofread using an on-line Geneious sequence analysis software (Biomatters Incorporated, San Francisco, Calif. 94107) supplemented with manual inspection and sequence reconciliation.

The gene encoding MLE, designated herein as SEQ. ID NO:1 (see FIG. 8B) was determined to have an EcoR1 site upstream of the original fragment isolated from the bacteriophage lambda library, and consequently the genomic fragment isolated from the EcoR1 digest did not contain the entire MLE coding region. Therefore, a second round of genomic cloning was carried out as above using a Pst1 digest of genomic DNA instead of an EcoR1 digest.

Although the original cDNA isolated from the lambda library appeared to contain the 3' end of the MLE gene, the region downstream was also sequenced to confirm this hypothesis. 4400 bases of sequence upstream of the known fragment were determined. The genes and promoter and start sites were predicted from this sequence using an on-line Softberry analysis (Softberry, Inc. Mount Kisco, N.Y. 10549).

DNA sequences from all stages of the genomic sequencing project were assembled into a consensus sequence using the on-line Geneious software (Biomatters Inc., San Francisco, Calif. 94107) and BLAST (Basic Local Alignment Search Tool) online software accessible from the NCBI website, and the predicted sequence was analyzed with the ExPASY translation tool from SIB, the Swiss Institute of Bioinformatics. See Artimo P. et al., ExPASy:SIB bioinformatics resource portal, Nucl. Acids Res., 40(W1):W597-W603, 2012, which is hereby incorporated by reference in its entirety. The genomic cloning project yielded a DNA sequence with a single open reading frame containing the cDNA sequence. The open reading frame predicted a polypeptide of 702 amino acids, as shown in SEQ ID NO:2 (see FIG. 9). The predicted complete polypeptide showed a 65% identity to its best match against the National Library of Medicine database using BLAST. That match is a hypothetical protein from *Herbaspirillum massiliense* that appears to belong to the glycogen debranching family.

The DNA sequence of the originally isolated cDNA clone (SEQ ID NO:3) contains a single base change from the same region of the genomic DNA (SEQ ID NO:1). The genomic sequence (SEQ ID NO:1) had an adenine (A) at position 2047, giving a codon of ATT, which encodes isoleucine (I). In the equivalent position, the original non-genomic sequence (SEQ ID NO:3; catalytic fragment) had a thymine (T), yielding a codon of TTT and encoding a phenylalanine (F). In short, the genomic DNA encoded an isoleucine at amino acid position 683 (SEQ ID NO:2), but the original cDNA clone expressed a phenylalanine at the same position (see SEQ ID NO:4). Both the isoleucine-containing polypeptide encoded by the genomic clone (SEQ ID NO:2) and the phenylalanine-containing peptide encoded by the cDNA clone (SEQ ID NO:4) have activity against the substrate.

The restriction map for the complete sequence was determined using RestrictionMapper, an on-line restriction mapping program developed by Peter Blaiklock. The information from all of these sources was used to select restriction enzymes to excise the gene from the genome to create a complete cDNA clone (as shown in SEQ ID NO:1), as well as to generate appropriate cloning primers with restriction enzyme recognition sites for cloning the gene into various plasmid expression vectors.

Clones of the complete genomic MLE DNA (SEQ ID NO:1) and the c-terminal MLE cDNA (SEQ ID NO:3) expressing amino acids 509 through the C-terminus at amino acid 702 (SEQ ID NO:4) and possessing catalytic activity have been constructed (see Table VI).

was pelleted by centrifugation, the supernatant was sterile-filtered to remove any particulates, and the supernatant was lyophilized and redissolved in 0.1 volumes of distilled water. As shown in FIG. 10, colored material was removed from the pulp. Standard TAPPI protocols for quantitative measurement of lignin release call for measurement at $OD_{280}$ for soluble lignin (See Dence, C. W., The determination of lignin, In: Methods in Lignin Chemistry, S. Y. Lin and C. W. Dence (eds), pp. 33-61, Springer-Verlag, Berlin Heidelberg (1992), which is hereby incorporated by reference in its entirety) or at $OD_{205}$ for the release of acid-soluble lignin (See TAPPI UM 250, Acid-soluble lignin in wood and pulp, In: Technical Association of the Pulp and Paper Industry Useful Methods, 1991 TAPPI, Atlanta, Ga. 1991, pp. 47-48, which is hereby incorporated by reference in its entirety) because of possible interference by furfurals formed during acid treatment. $OD_{200}$ has been found to be more effective for softwood lignins See Maekawa, E., An evaluation of the acid-soluble lignin determination in analysis of lignin by the sulfuric acid method, J. Wood Chem. Technol. 9(4):549-569 (1989), which is hereby incorporated by reference in its entirety. However, cell culture supernatants already have significant amounts of material absorbing at UV wavelengths that interfere with lignin measurement. An alternative measurement was developed.

Culture supernatant containing HLE activity was combined with kraft-cooked softwood pulp. A sample was withdrawn immediately or after 24 hrs of incubation at 30° C. Pulp was removed by centrifugation followed by filtration, and optical density was measured at 205 nm, 280 nm and 405 nm wavelengths. To read OD at 205 nm, the supernatant was diluted 500 fold. To read OD at 280 nm, the

TABLE VI

Constructs expressing containing complete and C-terminal MLE

| Insert | Vector (and source) | Host(s) | Expression inducer | Expression tag | Activity |
|---|---|---|---|---|---|
| Complete genomic MLE | pHIS525 (MoBiTec GmbH)* | B. megaterium B. subtilis | xylose | C-terminal 6X his | None |
| Catalytic (cDNA) fragment | pHIS525 (MoBiTec GmbH)* | B. megaterium B. subtilis | xylose | C-terminal 6X his | None |
| Complete genomic MLE | pAES40 (Athena Environ. Sci.)** | E. coli | IPTG/lactose | C-terminal 6X his | Good |
| Catalytic (cDNA) fragment | pAES40 (Athena Environ. Sci.)** | E. coli | IPTG/lactose | C-terminal 6X his | Poor |
| Complete genomic MLE | pHT43 (MoBiTec GmbH)* | B. subtilis | IPTG | None | Poor |
| Catalytic (cDNA) fragment | pHT43 (MoBiTec GmbH)* | B. subtilis | IPTG | None | Good |
| Complete genomic MLE | Bluescript SK⁻ (Stratagene) | E. coli | IPTG | None | Poor |
| Catalytic (cDNA) fragment | Bluescript SK⁻ (Stratagene) | E. coli | IPTG | None | Fair |
| Complete genomic MLE | pFN6A (Promega) | E. coli | IPTG | N-terminal Halo-Tag ® (MKHQHQHQAIA) | Poor |
| Catalytic (cDNA) fragment | pFN6A (Promega) | E. coli | IPTG | N-terminal Halo-Tag ® (MKHQHQHQAIA) | Poor |

*MoBiTec GmbH, 37083 Göttingen Germany
**Athena Environmental Science, Baltimore, MD 21227

Effect of rMLE on Native Substrates

Small Scale Treatment of the Pulp with rMLE Active Fragment—Lignin Removal.

A small sample of kraft softwood pulp was combined with a cell-free supernatant from *E. coli* expressing a pBluescript SK⁻ fusion protein of the active site of HLE fused to the α-peptide of β-galactosidase. Following incubation, the pulp supernatant was diluted 8 fold. To read OD at 405 nm, the supernatant was not diluted. In culture supernatants, aromatic and other organic compounds formed and released during growth of *E. coli* may be interfering with the measurement of molecules released from pulp. However, measurement at 405 nm to quantitate the yellow-orange color released was effective. The color may be due to the conversion of lignin subunits to quinones. See Agarwal U. P., Assignment of the photoyellowing-related 1675 cm Raman/IR band to p-quinones and its implications to the mechanism of color reversion in mechanical pulps, Journal of Wood Chem. and Technol. 18(4):381-402 (1998) and Spender, J., Photostabilization of High-Yield Pulps Reaction of Thiols and Quinones with Pulp, a master's thesis for the Department of Chemistry, University of Maine (2001), both of which are hereby incorporated by reference in their entirety.

TABLE VII

Solubilization of Lignin Measured at Different Wavelengths

| Sample | $A_{205}$ | $A_{280}$ | $A_{405}$ |
|---|---|---|---|
| M9 medium | 0 | 0 | 0 |
| Culture supernatant mixed with pulp, time 0 | −0.069 | −0.297 | .159 |
| Culture supernatant mixed with pulp, time 24 hrs | −.272 | −.483 | 0.363 |

Pilot Scale Treatment of Pulp with rMLE Active Fragment. Effect on Pulp Properties.

Clone 17-2 in phage λ was excised in vivo in using a helper phage as recommended by the manufacturer (Stratagene, now Agilent Technologies, Santa Clara, Calif. 95051) to yield the active fragment of MLE, amino acids 509-702 (SEQ ID NO:4) of the complete polypeptide (SEQ ID NO:2) fused in frame to the α-peptide of β-galactosidase. The construct in E. coli BL21 was grown overnight in 5 or 7 liter New Brunswick Scientific bioreactors (Enfield, Conn. 06082) in M9 medium containing 0.4% glycerol as the sole carbon source and 2 ml per liter of Trace Minerals (ATCC), and expression of the fusion protein was induced with 1 mM IPTG. The fusion protein was not exported actively into the medium, resulting in a very low concentration of enzyme in the culture supernatant.

Approximately 800 g of acid washed and oven-dried softwood kraft pulp at 15.37% consistency was washed 3× with distilled water, about 20 liters each wash. Between washes, the pulp was wrung dry in small batches in fine mesh bags. The pulp was then washed three times in MM9 (modified M9 medium containing 0.4% glycerol as the carbon source and 2 ml per liter of Trace Mineral Mix from ATCC). Between washes, the pulp was wrung dry as above. A small sample of the pulp was oven-dried to determine that the final consistency was 25.4%. 850 g of the pulp (corresponding to about 216 g of oven-dry pulp) was placed in each of 3 buckets. Buckets 1 and 2 were combined with 5 liters of fresh MM9. The third bucket was combined with 5 liters of culture supernatant. The pH of each bucket was adjusted to pH 5.0-5.5 with 1M citric acid. Each pulp mixture was heat-sealed into a plastic bag and incubated at 30° C. on a rotating platform for 24-36 hours. This process was repeated 2 times.

Between the incubations, the pulps were squeezed dry and usually added immediately to fresh MM9 or fresh culture supernatant. In some cases it was necessary to store the pulps for 1-2 days between incubations. In those cases, the pulps were individually washed several times with water, squeezed dry, and stored at 4° C. Before use, the individual pulps were again washed in fresh MM9 several times, squeezed dry, and then fresh MM9 or culture supernatant was added.

Following the incubations in MM9 and culture supernatants, the pulps were washed ×3 in water, squeezed dry, and resuspended in a final volume of 5 liters of 20 mM citrate buffer, pH 3.5. To Pulp 2 was added 5MU of commercial isoamylase (Sigma-Aldrich Corporation, St. Louis, Mo. 63178) to give a final concentration of 1 KU/ml. The pulps were incubated at 45° C. Pulps 1 and 3 were stopped after 2 hours. Pulp 2 was incubated overnight at 45° C. After the incubations were stopped, each pulp was washed extensively in distilled water.

The pulps were then delignified in a pilot scale oxygen delignifier at the Process Development Center (PDC) at the University of Maine. PDC measured a variety of pulp parameters in the starting pulp and the three experimental pulps. The results are summarized in Table VIII.

TABLE VIII

Effect of MLE pretreatment on Oxygen Delignified Pulp

| Pulp treatment Change relative to buffer treated controls | MLE (Probability of significance compared to control by t-test) | Isoamylase (Probability of significance compared to control by t-test) |
|---|---|---|
| Kappa number | −0.3 (87%) | +0.1 (<50%) |
| Brightness | −0.3 (81%) | −0.3 (81%) |
| Intrinsic viscosity | −10 (94%) | −2 (<50%) |

Effect of rMLE on Hardwood Biomass Substrate

Samples of hardwood biomass substrates pretreated with two different proprietary regimes were generously supplied by Mascoma Corporation (Waltham, Mass. 02451). The pulps were washed three times with 10 mM sodium citrate, pH 5.5 in HBSS by centrifugation to lower the initial pH. Aliquots of 0.5 g washed pulp were incubated with either 0.5 ml of cell-free culture supernatant or 0.5 ml of culture supernatant from the corresponding untransformed host strain. Each incubation was carried out at 29° C. with gentle shaking over the course of 72 hours. The samples were returned to Mascoma Corporation (Waltham, Mass. 02451) for saccharification to monosaccharides and subsequent quantification by HPLC analysis. For Substrate 1, the MLE catalytic fragment (SEQ ID NO:4) increased glucose concentration by about 20%, but the full length rMLE had little or no effect. For Substrate 2, the reverse held true. The catalytic fragment had no effect, and the full length MLE (SEQ ID NO:2) increased glucose concentration by about 5%. Treatment of Substrate 1 with the catalytic fragment also showed an increase in xylose recovery. However, treatment of the pulps with the complete recombinant MLE had little effect on xylose recovery.

TABLE IX

Effect of Recombinant MLE on Hardwood Pulp Sugar Recovery-% increase over relevant control.

| | Treatment | |
|---|---|---|
| Pulp | Catalytic fragment[1] | Complete genomic MLE[2] |
| Substrate 1 Glucose content, g/L | 20.4% | −0.2% |
| Substrate 1 Xylose content, g/L | 21.7% | 4.3% |

TABLE IX-continued

Effect of Recombinant MLE on Hardwood Pulp Sugar Recovery-% increase over relevant control.

| Pulp | Treatment | |
|---|---|---|
| | Catalytic fragment[1] | Complete genomic MLE[2] |
| Substrate 2 Glucose content | 0.1% | 5.1% |
| Substrate 2 Xylose content | 0.0% | 0.0% |

[1]Culture supernatant from a *B. subtilis* host transformed with pHT43 to expressthe catalytic fragment of MLE fused to an export sequence, grown in M9 minimal medium and induced with IPTG.
[2]Culture supernatant from an *E. coli* host transformed with pAES40 to express the complete MLE fused to an export sequence, grown in M9 minimal medium and induced with IPTG/lactose.

Example 6

Cloning of xle

XLE activity was identified using zymography, an electrophoretic technique that reveals protein bands based on their enzymatic activity. Non-denaturing polyacrylamide gels were based on the original Laemmli formulation of polyacrylamide gels, (see Laemmli, "An efficient polyacrylamide gel electrophoresis system for proteins separation." Nature 227: 690-695 (1970), which is incorporated herein by reference in its entirety), but sodium dodecyl sulfate and β-mercaptoethanol were eliminated from the running gel, stacking gel and sample buffer. E518 cells were grown in shake flasks at 34° C. in HBSS containing 2 ml per L of trace element mix from American Type Culture Collection (Manassas, Va. 20110) containing either 0.4% oligoxylose (Cascade Analytical Reagents and Biochemicals, Corvallis, Oreg.) or a mix of 0.35% oligoxylose and 0.05% benzylated xylan. Samples were taken from each culture after 29 hours of growth at 34° C. Each sample was desalted vs HBSS without ammonium nitrate and concentrated on a spin column with a molecular weight cut-off of 2 KD preconditioned according to manufacturer's protocol (Sartorius Stedim North America Inc. Bohemia, N.Y. 11716) or 3 KD (Amicon, EMD Millipore, Billerica Mass. 01821) and lyophilized. After lyophilization, each sample was dissolved in about 1/150 of its original volume.

Figure 11:
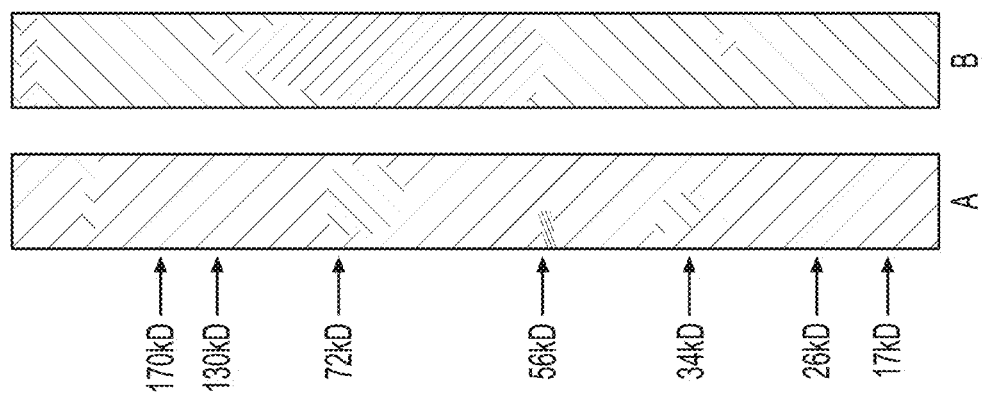
FIG. 11 shows the zymography of E518 culture supernatant. Culture supernatant from E518 grown for 29 hours in medium containing oligoxylan and benzylated xylan. The culture supernatants were diafiltered and concentrated using a Sartorius 2 kD cutoff spin column, lyophilized, and redissolved in native gel sample buffer at a final concentration of about 150 fold. Duplicate samples were loaded onto wells of a 10% native gel. One half of the gel was stained with Coomassie Blue G250 and the other half was soaked in HBSS without ammonium nitrate for 10 minutes to exchange the buffer and then blotted dry with filter paper and overlaid with 2 ml of 4MU-xylan in 0.175% agarose. The gel-overlay sandwich was incubated for 8 to 10 minutes, and removed. A pieced of PVDF membrane (wetted and equilibrated with HBSS) was applied to the non-overlay side of the gel for 5 minutes. The PVDF membrane was incubated with 0.1M sodium borate, pH 9.9, for 1 minute, illuminated with short-wave UV light, and photographed. Lane a shows the Coomassie stain, and Lane b is the zymograph of the PVDF membrane corresponding to the duplicate lane that was zymographed.

Each sample was run in duplicate on the same gel which was then cut in half. One half of the gel was stained with Commassie Brilliant Blue G-250 (Thermo Fisher Scientific, Waltham, Mass. USA 02451) and the other half was zymographed. Zymography was performed after exchanging the gel buffer by soaking the gel for 10 minutes in HBSS containing 1% Triton X-100. The gel was then overlaid with 0.35% agarose in HBSS containing 4MU-xylan substrate and allowed to remain on the gel for 8 minutes. The agarose was then removed and a wetted PVDF membrane was immediately overlaid onto the gel for 5 minutes. The membrane was carefully removed. The membrane and the gel piece were then rinsed with 0.1 M sodium borate buffer at pH 9.9 and photographed (FIG. 11). Pieces of Coomassie stained gels corresponding to the regions of the strongest zymographic activity were sent for protein microsequencing to the Protein and Nucleic Acid Analysis Core Facility at the Maine Medical Center Research Institute (Scarborough, Me. 04074).

The microsequencing process revealed a number of peptides whose likely polypeptides of origin were determined by comparison to a Uniprot *Paenibacillus* database. See The UniProt Consortium, Activities at the Universal Protein Resource (UniProt), Nucleic Acids Res. 42: D191-D198, 2014, which is incorporated herein by reference in its entirety. Six peptides were investigated that had the best chance of being from an XLE polypeptide. These were peptides identified as originating from polypeptides belonging to 1) bacterial flagellin, 2) hydrolase, 3) licheninase, 4) esterase, 5) toxic anion resistance protein and 6) unknown families of proteins.

The DNA sequences corresponding to each of the candidate peptides from *Paenibacillus* species were determined from the UniProtKB and NIH genomic databases. PCR primer sets were designed for each of the peptides using the OligoCalc oligonucleotide properties calculator, as described above. The PCR primers were tested against genomic DNA from E518 to confirm that they would indeed generate a DNA fragment of the expected size. If not, the gene family members from *Paenibacillus* species in the UniProtKB and NIH genome databases were aligned and examined for highly conserved regions, and those regions were used for primer redesign. After any primer redesign, the resulting primers were tested against genomic DNA from E518. This process also served to choose PCR conditions. In addition, primer sets were tested against *E. coli* DNA, to ensure that there were no host reactions to complicate the PCR assay. In some cases, the primer pairs were used to amplify genomic DNA from E518 for DNA sequencing. This sequence was then used to design unambiguous primers.

TABLE X

Screening Primers for Genes That May Encode XLE

| Primer name | Sequence | SEQ ID NO. |
|---|---|---|
| R9LCP9FM3 | ATGGGGGAACAAYGAACTKCAGTAYYATA | 31 |
| R9LCP9MRCAL | AAMCKTTGGTTRTTGGCGRMRTAG | 32 |
| R9seqF1 | CAGGTGACGGGTGGAAATCTGG | 33 |
| R9seqR1 | CTGCTGAATCTTCGCTCCGCTG | 34 |
| G0VVFM3 | GGATGGGGAAACAATGARCTGCAGTAYTAT | 35 |
| G0VVRM3 | CCARTTYCCGCCRACCGCNARRTTCAG | 36 |
| C6D588F3 | GAGCTGGCTACACAATCCGCGAACGGT | 37 |
| C6D588R6 | CAGAACGCCTTGCGGTTGTTGATTAGCTTG | 38 |
| S3AYW2F2 | GGAGTCCTGGAGCGTGTGACGATGC | 39 |
| S3AYW2R2A | AATGCCGAAAGGCGCTCGCAAAGCT | 40 |
| E0IAJ1F1 | CTCACCCGAAGAACGCCAGCTGATGAAC | 41 |
| E0IAJ1R2 | GTGTACGTAATGCGGGGGAACGAAC | 42 |
| T2LU54F1 | TTGAGGTAGCCAGCCCGGAAGAGATCA | 43 |
| T2LU54R2A | GTGTACGTAATGCGGGGGAACGAAC | 44 |

In order to generate a genomic library, the genome size of E518 was assumed to be similar to those of its closest relatives: *Paenibacillus lautus* Y412MC10, 7.1 Mb (See Mead et al., "Complete Genome Sequence of *Paenibacillus* strain Y4.12MC10, a Novel *Paenibacillus lautus* strain Isolated from Obsidian Hot Spring in Yellowstone National Park," Standards in Genomic Science 6:3 (2012), which is incorporated herein by reference in its entirety), *Paenibacillus polymyxa* E681, 5.4 Mb (See Kim J F, et al., "Genome sequence of the polymyxin-producing plant-probiotic *rhizobacterium Paenibacillus polymyxa* E681," J. Bacteriol. 192 (22), 6103-6104 (2010), which is incorporated herein by reference in its entirety), *Paenibacillus polymyxa* SC2, 6.21 Mb (See Ma et al., "Complete genome sequence of *Paenibacillus polymyxa* SC2, a strain of plant growth-promoting *Rhizobacterium* with broad-spectrum antimicrobial activity," J. Bacteriol. 193(1): 311-312 (2011), which is incorporated herein by reference in its entirety), and *Paenibacillus terrae* HPL-003, 6.1 Mb (See Shin et al., "Genome sequence of *Paenibacillus terrae* HPL-003, a xylanase-producing bacterium isolated from soil found in forest residue," J. Bacteriol. 2012 194(5):1266 (2012), which is incorporated herein by reference in its entirety). These values were all about 6±1 Mb.

The probability that a gene of interest will be covered in a random library of fragments of genomic DNA is $$N = \frac{\ln(1-P)}{\ln(1-a/b)}$$

wherein N is the number of recombinants to be screened, P=the probability of including a particular sequence in a random genomic library, a=the mean size of the fragments divided by the genome size, and b=the genome size (See Clarke et al., "A colony bank containing synthetic CoI EI hybrid plasmids representative of the entire *E. coli* genome," Cell 9: 91-99 (1976), which is incorporated herein by reference in its entirety). Creating the library in cosmid vectors, where the average insert size is 40 kB, reduces the number of clones to be screened for a 95% chance of finding the gene to about 500, which is a reasonable number to screen by a PCR assay. If the library is created in a standard cloning vector with an average insert size of 2 kB, the number of recombinants to be screened would be close to 10,000, which may not be a reasonable number to screen by PCR.

Genomic DNA was prepared from E518 bp lysing the cells using B-Per reagent (Thermo Fisher Scientific Inc., Rockford, Ill. USA 61101) following manufacturer's instructions, except that 2.5 µg/ml RNase A, 0.016 U/ml *B. subtilis* protease, 0.1 mg/ml lysozyme, and 60 µg/ml proteinase K were added instead of DNase I and any vigorous pipetting was avoided. The resulting supernatant containing genomic DNA was extracted twice with phenol:chloroform, and the DNA was precipitated from the aqueous layer with ethanol. The pellet was allowed to air-dry for at least 1 hour and resuspended gently in TE buffer to a final concentration of approximately 0.4 µg/µl.

The genomic DNA was sheared to an average size of approximately 40 kB by passing it through a 200 µl pipette tip about 50-70 times. The size range of the resulting fragments was tested by gel electrophoresis. Multiple preparations of genomic DNA were used for library preparation, and each preparation was tested individually for the appropriate number of passes through a pipette tip to generate fragments with an average size of 40 kB. Sheared DNA was separated by gel electrophoresis on low melting-point agarose. Each DNA sample was loaded into two lanes: a control lane for location and a lane with a higher concentration of DNA for isolation. Once the gel was run, the portions containing the control sample lanes along with a lane containing a cosmid size marker supplied with the pWEB kit were cut off and stained with ethidium bromide. The region corresponding to approximately 40 kB was cut out of the unstained portion of the gel and the DNA was isolated from the gel as recommended by the manufacturer of the pWEB kit (Epicentre Biotechnologies, Madison, Wis. 53719).

A cosmid library from E518 genomic DNA was constructed and plated using a pWEB cosmid kit (Epicentre Biotechnologies, Madison, Wis. 53719) following manufacturer's directions. Individual colonies were picked into individual wells of 96 deep well plates, each well containing 400 µl of *E. coli* growth medium, as well as to a gridded petri dish. When the cultures in the 96 well plate were grown up, 150 µl of each well's contents was removed and combined with similar aliquots from 7 other wells in a microfuge tube. The cells from the pooled cultures in the tubes were pelleted by centrifugation and washed twice with distilled water. 1 µl of a 1:10 dilution of the pooled pelleted cell pellets was used for each PCR assay. Each of the original wells of the deep well plates (now containing 250 µl of cell culture) was mixed with 50% glycerol to a final concentration of 25% and the plates were frozen and stored at −80° C. The gridded petri dishes were grown overnight and stored at 4° C. until needed.

When a pooled cell mixture showed a positive reaction by PCR, the eight individual colonies of the pool were picked from the colonies on the gridded plate that corresponded to the wells used to construct the pool. Each of those colonies was inoculated to an individual petri dish as well as to an individual LB broth culture. The cell pellets obtained from the individual broth cultures were tested by PCR, and the single positive isolate was further purified by amplifying its individual colonies and retesting by PCR. Freezer stock was made from several isolates of each positive.

Interestingly, clones positive for the licheninase primer pair were also positive for the hydrolase primer pair. The DNA sequence of the PCR product generated using the hydrolase primer pair was determined and shown to encode the amino acid sequence of the peptide previously identified as being from an enzyme belonging to the licheninase family. It seemed likely that both the licheninase and hydrolase peptides identified by microsequencing were part of the same polypeptide. The identical origin of both peptides was confirmed by a PCR analysis. When the forward primer for the licheninase gene was paired with the reverse primer for the hydrolase gene, a ~700 bp band was generated. It was evident that the two peptide fragments were in fact part of the same gene.

The PCR positive isolates were further tested by assaying for XLE activity. Broth cultures were grown in M9 complete medium and the cells pelleted by centrifugation. The cell pellets were washed twice with HBSS without ammonium nitrate and the drained pellets were weighed, treated with protease inhibitor cocktail (P8465, Sigma-Aldrich Chemicals, St. Louis, Mo. 63178) and frozen. To assay the pellets for XLE activity, the pellets were thawed on ice, treated with B-Per reagent (Thermo Fisher Scientific Inc., Rockford, Ill. USA 61101) containing 2.5 µg/ml RNase A, 0.1 mg/ml lysozyme, and 1 ml/g cells protease inhibitor cocktail, and incubated at room temperature for 10 minutes. 1.5 volumes of HBSS without ammonium nitrate was then added to the treated cells, and the lysed cells were heated to 65° C. for 10 minutes. The tubes were centrifuged, and the supernatant used in an assay for XLE activity as above. Culture supernatant from E518 served as a positive control and HBSS was the negative control. Of the five individual clones tested, two were more strongly positive than the E518 control, one was approximately as positive as the E518 control, and two were clearly negative.

Cosmid DNA was extracted from the PCR positive isolates in an attempt to sequence the gene. However, the sequence generated from the cosmids was not clean enough for a confident sequence. An alternative sequencing approach looked for those cosmids in which the xle gene was close enough to the cosmid insertion site that an xle primer paired with a cosmid primer could amplify previously unsequenced regions of the xle gene. All of the PCR positive isolates were tested. One isolate, 5-1F, generated an approximate 1 kb band when the T7 (cosmid vector) primer was paired with the R9seqR1 primer. The sequence generated from this PCR fragment was used to obtain the start site and some upstream region of the gene. When the cosmid M13 primer was paired with R9seqF1, two other isolates, 3-2G and 4-5F yielded a 4 kb and a 2 kb fragment respectively. These isolates were used to determine the remaining downstream sequence of xle.

When the entire xle gene sequence was put together, it was discovered that there was no BamHI site present in the gene. Isolate 1-8C had XLE activity but did not show a PCR fragment from any vector primer combined with any xle primer despite having been positive with licheninase and hydrolase primers, indicating that the xle gene was likely both to be complete and to be located far from the insertion site. Consequently, a substantial portion of the upstream and downstream gene regions were likely to be present. 1-8C was digested with BamHI and the fragments ligated into the BamHI site of pUC19. Individual transformants were screened by PCR using primers R9seqF1 and R9seqR1 (see Table X). One positive, named pUCXLE44, was found with an insert of approximately 8 kb. pUC19XLE44 was grown overnight in LB broth culture, and the plasmid purified using the GenCatch Plasmid Mini-Prep Kit (Epoch Life Sciences Inc, Sugar Land, Tex. 77496). The insert DNA was sequenced using pUC19 primers and with the primers developed for PCR of xle from cosmids and E518. Additional primers required to complete the sequence were developed as sequence data became available and are listed in Table XI.

TABLE XI

Additional xle Sequencing Primers

| Primer name | Sequence | SEQ ID NO. |
|---|---|---|
| XLEfor1 | GCAAAGTCATGGATGTGGTCGATG | 45 |
| XLErev2 | TAATATCCGCCTCCGACATCCACGG | 46 |
| INR9revF1 | CCAGATTTCCACCCGTCACCTG | 47 |
| INR9revR1 | CAGCGGAGCGAAGATTCAGCAG | 48 |

DNA sequences determined from clones and from walking experiments were proofread using a Geneious sequence analysis software (Biomatters Incorporated, San Francisco, Calif. 94107) supplemented with manual inspection and sequence reconciliation. An on-line Softberry analysis (Softberry, Inc. Mount Kisco, N.Y. 10549) suggested that the xle gene is an independent transcriptional unit and not part of an operon.

The xle gene (SEQ ID NO:49, FIG. 12) encodes 412 amino acids (SEQ ID NO:50, FIG. 13), and is both preceded and succeeded by multiple stop codons. A BLAST search (see Altschul et al., "Gapped BLAST and PSI-BLAST: a new generation of protein database search programs," Nucleic Acids Res. 25:3389-3402 (1997), which is hereby incorporated by reference in its entirety) using either the protein sequence or the DNA sequence revealed its closest relatives (approximately 80% identity in either case) to be members of the laminarinase-like subfamily of glycoside hydrolase family 16 with activity towards 1,3 β-glucans. The highest levels of identity were with genes from other members of the *Paenibacillus* genus and with a *Bacillus circulans* strain. In addition, there is high homology (~80% identity at the amino acid level) with a xylanase from *Paenibacillus* sp. JCM 10914.

There is a relationship between 1,3 β-glucanase and XLE. Xylose in xylan is in the pyranose conformation, and it has the same stereochemistry at carbons 1, 2, 3 and 4 as glucose in β-glucan. The major difference between the two sugars as residues in a polysaccharide chain is whether a C6 group is attached to C5.

In addition, the carboxyterminus of the sequence contains a sugar binding site of the ricin superfamily, composed of three repeats of a QXW motif (see Hazes, "The (QxW)3 domain: a flexible lectin scaffold," Protein Sci. 5(8):1490-1501 (1996), which is hereby incorporated by reference in its entirety). In XLE, the QXW repeats consist of two QQW and one QRW domains (underlined, as shown in FIG. 13).

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

REFERENCES

Ragauskas, A. J., Williams, C. K., Davison, B. H., Britovsek, G., Cairney, J., Eckert, C. A., Frederick, W. J. Jr., Hallett, J. P., Leak, D. J., Liotta, C. L., Mielenz, J. R., Murphy, R., Templer, R. and Tschaplinski, T. 2006. The path forward for biofuels and biomaterials. Science 311:484-489.

ICIS Chemical Business, Feb. 11, 2008. Biofuels backlash grows in fuel versus food debate. Simon Robinson/London.

Werpy, T. and Peterson, G. 2004. Top value-added chemicals from biomass, volume I. Results of screening for potential candidates from sugars and synthesis gas. U.S. Department of Energy, National Renewable Energy Laboratory, Publication No. DOE/GO-102004-1992.

van Heiningen, A. 2006. Converting a kraft pulp mill into an integrated forest biorefinery. Pulp and Paper Canada 107: 38-43.

Sun, X. F., Sun, R. C., Zhao, L., and Sun, J. X. 2004. Acetylation of sugarcane bagasse hemicelluloses under mild reaction conditions by using NBS as a catalyst. Journal of Applied Polymer Science 92: 53-61.

Robinson, D. 1956. The fluorometric determination of β-glucosidase: its occurrence in the tissues of animals, including insects. Biochemical Journal 63:39.

Sluiter, A., Hames, B., Ruiz, R., Scarlata, C., Sluiter, J., Templeton, D., and Crocker, D. 2011. Determination of structural carbohydrates and lignin in biomass. Laboratory Analytical Procedure (LAP) (Version Jul. 8, 2011). Technical Report NREL/TP-510-42618.

Warnick, T. A., Methe, B. A. and Leschine, S. B. 2002. *Clostridum phytofermentans* sp. nov., a cellulolytic mesophile from forest soil. Int. J. Systemat. Evolut. Microbiol. 52:1155-1160.

Alexander, M. 1965. Biodegradation: problems of molecular recalcitrance and microbial fallibility. Adv. Appl. Microbiol. 7:35-80.

Chang, M. C Y. 2007. Harnessing energy from plant biomass. Curr Op Chem Biol. 11:677-684.

Danneel, H.-J., Rossnerz, E. Zeeck, A. and Giffhor, F. 1993. Purification and characterization of a pyranose oxidase from the basidiomycete Peniophora gigantea and chemical analyses of its reaction products. Eur. J. Biochem. 214:795-802

Connell, L., Redman, R., Craig, S., and Rodriguez, R. 2006. Distribution and abundance of fungi in the soils of Taylor Valley, Antarctica. Soil Biol. Biochem. 38:3083-3094.

Lu, Y. 2002. Benzyl konjac glucomannan. Polymer 43:3979-3986.

Stark, M., Berger, S. A., Stamatakis, A., von Mering, C. 2010. MLTreeMap—accurate Maximum Likelihood placement of environmental DNA sequences into taxonomic and functional reference phylogenies. BMC Genomics 11:461 doi:10.1186/1471-2164-11-461 http://www.biomedcentral.com/1471-2164/11/461.

Ausubel, F., Brent, R., Kingston, R. E., Moore, D. D., Seidman, J. G., Smith, J. A., and Struhl, K. A. 1995. Short Protocols in Molecular Biology. Wiley and Sons, NY.

Dence, C. W. 1992. The determination of lignin. In Methods in Lignin Chemistry, S. Y. Lin and C. W. Dence eds. Springer-Verlag, New York.

Technical Association of the Pulp and Paper Industry, Atlanta 1991. Official Test Method UM250. Acid-soluble lignin in wood and pulp. Useful Methods. pp. 47-48.

Maekawa, F. Ichizawa, T. and Koshijima, T. 1989. An evaluation of the acid-soluble lignin determination in analysis of lignin by the sulfuric acid method. J. Wood Chem. Technol. 9:549-569.

Agarwal U. P. 1998. Assignment of the photo-yellowing-related 1675 $cm^{-1}$ Raman/IR band to p-quinones and its implications to the mechanism of color reversion in mechanical pulps. Journal of Wood Chemistry and Technology 18:381-402.

Spender, J. 2001. Photostabilization of high-yield pulps reaction of thiols and quinones with pulp, a master's thesis for the department of Chemistry, University of Maine.

Samuel, R., Foston, M., Jiang, N., Allison, L., and Ragauskas, A. J. 2011. Structural changes in switchgrass lignin and hemicelluloses during pretreatments by NMR analysis. Polym. Degrad. Stabil. 96(11):2002-2009.

Dayhoff (ed.). 1978. Atlas of Protein Sequence and Structure, Vol. 5, Suppl. 3, Natl. Biomed. Res. Round., Washington D.C., pp. 345-352.

Henikoff, S. and Henikoff, J. G. 1992. Amino acid substitution matrices from protein blocks. Proc. Natl. Acad. Sci. USA, 89:10915-10919.

Sambrook et al. 1989. Molecular Cloning, A Laboratory Manual, 2d edition, Cold Spring Harbor, N.Y.

Altschul, S. F., Madden, T. L., Scháffer, A. A., Zhang, J., Zhang, Z., Miller, W. and Lipman, D. J. 1997. Gapped BLAST and PSI-BLAST: a new generation of protein database search programs. Nucleic Acids Res., 25:3389-3402.

Nielsen, H., Engelbrecht, J., Brunak, S., and von Heijne, G. 1997. Identification of prokaryotic and eukaryotic signal peptides and prediction of their cleavage sites. Protein Eng. 10:1-6.

Prongjit, M., Sucharitakul, J., Wongnate, T., Haltrich, D. and Chaiyen, P. 2009. Kinetic mechanism of pyranose 2-oxidase from Trametes multicolor. Biochem. 48(19):4170-4180.

Kibbe, W. A. 2007. OligoCalc: an online oligonucleotide properties calculator. Nucl. Acids Res., 35(2):W43-W46.

Janson, J.-C. and Ryden, L. (eds). 1989. Protein Purification: Principles, High Resolution Methods and Applications, VCH Publishers, Inc., New York.

Sievers, F., Wilm, A., Dineen, D., Gibson, T. J., Karplus, K., Li, W., Lopez, R., McWilliam, H., Remmert, M., Södding, J., Thompson, J. D., Higgins, D. G. 2011. Fast, scalable generation of high-quality protein multiple sequence alignments using Clustal Omega. Mol. Syst. Biol., 7(539):1-6.

---

What is claimed is:

1. A cDNA encoding a polypeptide that specifically cleaves a non-glycosidic ether bond between a lignin or a derivative thereof and a saccharide wherein said polypeptide comprises an amino acid sequence having at least 85% sequence identity to the amino acid sequence of SEQ ID NO:2 or SEQ ID NO:4 or SEQ ID NO: 50.

2. The cDNA of claim 1, wherein cleavage of the non-glycosidic ether bond is between an aromatic carbon of the lignin or the derivative thereof and the saccharide.

3. The cDNA of claim 1, wherein cleavage of the non-glycosidic ether bond is between a non-aromatic carbon of the lignin or the derivative thereof and the saccharide.

4. The cDNA of claim 3, wherein said non-aromatic carbon of the lignin is an α-linked benzyl carbon or a β-linked benzyl carbon.

5. The cDNA of claim 1, wherein said saccharide is selected from the group consisting of a monosaccharide, a disaccharide, an oligosaccharide, and a polysaccharide.

6. The cDNA of claim 1, wherein said saccharide is a polysaccharide and said polysaccharide is hemicellulose.

7. The cDNA of claim 1 wherein the polypeptide comprises an amino acid sequence having at least about 90-95% sequence identity to the amino acid sequence of SEQ ID NO:2 or SEQ ID NO: 4 or SEQ ID NO: 50.

8. The cDNA of claim 1, wherein said cDNA comprises a nucleotide sequence of SEQ ID NO:1 or SEQ ID NO:3 or SEQ ID NO: 49.

9. A nucleic acid construct or an expression vector comprising the cDNA of claim 1 wherein said cDNA is operably linked to one or more control sequences that direct the expression of the polypeptide in an expression host.

10. The nucleic acid construct or expression vector of claim 9, wherein said construct or vector is selected from the group consisting of pHIS525-cMLE, pHIS525-cfMLE, pAES40-cMLE, pAES40-cfMLE, pHT43-cMLE, pHT43-cfMLE, pBluescript SK-cMLE, pBluescript SK-cfMLE, pFN6A-cMLE and pFN6A-cfMLE.

11. A transformed host cell comprising an expression vector that comprises the cDNA of claim 1 wherein said cDNA is operably linked to one or more control sequences that direct the production of the polypeptide.

12. The transformed host cell according to claim 11, wherein said host cell is selected from the group consisting of *B. megaterium* (pHIS525-cMLE), *B. subtilis* (pHIS525-cMLE), *B. megaterium* (pHIS525-cfMLE), *B. subtilis* (pHIS525-cfMLE), *E. coli* (pAES40-cMLE), *E. coli* (pAES40-cfMLE), *B. subtilis* (pHT43-cMLE), *B. subtilis* (pHT43-cfMLE), *E. coli* (pBluescript SK⁻-cMLE), *E. coli* (pBluescript SK⁻-cfMLE), *E. coli* (pFN6A-cMLE) and *E. coli* (pFN6A-cfMLE).

13. A method of producing a heterologous polypeptide that specifically cleaves a non-glycosidic ether bond between a lignin or a derivative thereof and a saccharide, comprising:

(a) Cultivating the transformed host cell of claim 12 under conditions conducive for production of the heterologous polypeptide; and
(b) recovering the heterologous polypeptide.

14. The cDNA of claim 1, wherein said polypeptide comprises the amino acid sequences of SEQ ID NO:50.

15. The cDNA of claim 14, wherein said polypeptide comprises an amino acid sequence having at least about 85% sequence identity to the amino acid sequence of SEQ ID NO:50.

16. The cDNA of claim 15 wherein said polypeptide comprises an amino acid sequence having at least about 90-95% sequence identity to the amino acid sequence of SEQ ID NO:50.

17. The cDNA of claim 1, wherein said cDNA comprises a nucleotide sequence of SEQ ID NO:49.

* * * * *

SEQUENCE LISTING

```
<160> NUMBER OF SEQ ID NOS: 50

<210> SEQ ID NO 1
<211> LENGTH: 2109
<212> TYPE: DNA
<213> ORGANISM: Escherichia coli

<400> SEQUENCE: 1
atgcctgcac ttcccgaacg catgcagtcc ggcacgccgt accccctggg tgcgacctgt      60
gacggcatgg gtaccaactt tgccgtcttc tccgcccacg cggagcgcat cgaattgtgc     120
ctgttcgatc cctccggcaa gcgggagatc gcgcgctacg acctgcccga gtgcaccgac     180
gaaacctggc atggttatct gccgcgcgtc cgtggtggca cgctctacgg cttccgggcg     240
tacgggcctt acgagcccga ggaggggcat cggttcaatc cgaacaaact cctcctcgat     300
ccgtatgcgc gcctgttgca cgggcaggtg cgctggtcgg acgccctgca tggttaccgg     360
gtttcctcgc cgcgcgccga tctgtcattc gaccggcggg acagtgccgc ggccatgccc     420
aaggcggtgg tggtcgacga gcccatgcac tggaccgggg gcaaccggcc gcataccccg     480
tggaacgaga cgatcatcta cgagacgcac ctgcggggtt tcacgcgcac gctaaagcga     540
attcgccaga acgagcgcgg cacgttcatt gccctggccg atccctacgt gatcgactat     600
```

```
ctggtcaaac tgggcatcac cgcggtggaa ctcctgcccg tgcacgcctt cgtgcaggac    660
cgtcgtctca ccgagatgaa gctgcgcaat tactggggct acaacacgct tgccttcttc    720
gcgcccgagc cggggtacat ggccgaagga gcgctcaacg agatacgcgc cgcggtgcag    780
gcgttgcatg cggcggggat cgaggtgatc ctcgacgtgg tctacaacca cacctgcgag    840
ggcagcgaac tgggtacgac gatgtcgttc cgtgggctgg acaacaaaag ctattaccgg    900
ctcatgccgg acaatccgcg ctactgcatc aacgataccg gtaccggcaa cacggtcaac    960
acggcgcacc cgcgggtcat ccagctggtg atggactcgc tgcgctactg ggtgcagacc   1020
ttccacatcg acggcttccg cttcgatctc ggcgtaagcc tggacgtgat ggaccaaggg   1080
ttcgatccct gctgcggcct gttcgacgcg atgcgccagg atcccgtgct cgccaacgtg   1140
aagttgatct ccgagccgtg ggacatcggc cctggtggct atcaactggg caatcatccg   1200
ccgggcttcg ccgagtggaa cgggcagttc cgcgacgaca tccgtaagtt ctggaagggc   1260
gattcgaata tgcggggcat ccttgccggc cggctccagg catccggcga actgttcgat   1320
caccagcggc gaaagccctg ggcctcggtg aacttcgtca ccgcgcacga cggcttcacg   1380
ctggaagacc tggtcagcta caacgacaaa cacaacgacg ccaacggcga agaaaatcgc   1440
gatggcggca acgataacga gagctacaac cacggtgtgg aggggccgag cgacgatccg   1500
gccgttcgta ttccgcgcga tcgcgtgaag gcgccatgc tggcgacgat gttcttctcg   1560
cacggcacgc ccatgctact gggggggcgac gagttcggcc gtacgcaaca gggcaacaac   1620
aatgcctatt gccaggacaa cgaattgtca tggtacgact ggaagctcgc cacgtcggag   1680
cagggcaggg agctgaccga cttcgtggcg cggctggcac ggttgcgcga acagcacccc   1740
acgttgcgcg ccgcgcattt cctgcgtggc gataaggagg tcgcgccggg tatgcgcgag   1800
gtggcatggt tcgacgagag tggcgcggag atgacccagg aaacctgggg ttatacagag   1860
gggcgcctgc ttgccctgcg tcgcgcccag gcgtacggcg agaagcgcgc cgacgtgacc   1920
ctcgtgctga tcaacgcgac gcccgagacc catgtgttcc atctgccggc acccgcggtc   1980
aactggcgga tgcgctgcaa cagtgcggtg cctgacgcaa ccgaggtcgc atggaccgat   2040
tcgaccattg cggtcgaagg gcgcagcgtg atcctgctcg gctcgattgt ccggaccgaa   2100
ccggcatga                                                          2109
```

<210> SEQ ID NO 2
<211> LENGTH: 702
<212> TYPE: PRT
<213> ORGANISM: Escherichia coli

<400> SEQUENCE: 2

Met Pro Ala Leu Pro Glu Arg Met Gln Ser Gly Thr Pro Tyr Pro Leu
1               5                   10                  15

Gly Ala Thr Cys Asp Gly Met Gly Thr Asn Phe Ala Val Phe Ser Ala
            20                  25                  30

His Ala Glu Arg Ile Glu Leu Cys Leu Phe Asp Pro Ser Gly Lys Arg
        35                  40                  45

Glu Ile Ala Arg Tyr Asp Leu Pro Glu Cys Thr Asp Glu Thr Trp His
    50                  55                  60

Gly Tyr Leu Pro Arg Val Arg Gly Gly Thr Leu Tyr Gly Phe Arg Ala
65                  70                  75                  80

Tyr Gly Pro Tyr Glu Pro Glu Glu Gly His Arg Phe Asn Pro Asn Lys
                85                  90                  95

```
Leu Leu Leu Asp Pro Tyr Ala Arg Leu Leu His Gly Gln Val Arg Trp
            100                 105                 110

Ser Asp Ala Leu His Gly Tyr Arg Val Ser Pro Arg Ala Asp Leu
        115                 120                 125

Ser Phe Asp Arg Arg Asp Ser Ala Ala Ala Met Pro Lys Ala Val Val
    130                 135                 140

Val Asp Glu Pro Met His Trp Thr Gly Gly Asn Arg Pro His Thr Pro
145                 150                 155                 160

Trp Asn Glu Thr Ile Ile Tyr Glu Thr His Leu Arg Gly Phe Thr Arg
                165                 170                 175

Thr Leu Lys Arg Ile Arg Gln Asn Glu Arg Gly Thr Phe Ile Ala Leu
            180                 185                 190

Ala Asp Pro Tyr Val Ile Asp Tyr Leu Val Lys Leu Gly Ile Thr Ala
        195                 200                 205

Val Glu Leu Leu Pro Val His Ala Phe Val Gln Asp Arg Arg Leu Thr
210                 215                 220

Glu Met Lys Leu Arg Asn Tyr Trp Gly Tyr Asn Thr Leu Ala Phe Phe
225                 230                 235                 240

Ala Pro Glu Pro Gly Tyr Met Ala Glu Gly Ala Leu Asn Glu Ile Arg
                245                 250                 255

Ala Ala Val Gln Ala Leu His Ala Ala Gly Ile Glu Val Ile Leu Asp
            260                 265                 270

Val Val Tyr Asn His Thr Cys Glu Gly Ser Glu Leu Gly Thr Thr Met
        275                 280                 285

Ser Phe Arg Gly Leu Asp Asn Lys Ser Tyr Tyr Arg Leu Met Pro Asp
    290                 295                 300

Asn Pro Arg Tyr Cys Ile Asn Asp Thr Gly Thr Gly Asn Thr Val Asn
305                 310                 315                 320

Thr Ala His Pro Arg Val Ile Gln Leu Val Met Asp Ser Leu Arg Tyr
                325                 330                 335

Trp Val Gln Thr Phe His Ile Asp Gly Phe Arg Phe Asp Leu Gly Val
            340                 345                 350

Ser Leu Gly Arg Glu Asp Gln Gly Phe Asp Pro Cys Cys Gly Leu Phe
        355                 360                 365

Asp Ala Met Arg Gln Asp Pro Val Leu Ala Asn Val Lys Leu Ile Ser
    370                 375                 380

Glu Pro Trp Asp Ile Gly Pro Gly Gly Tyr Gln Leu Gly Asn His Pro
385                 390                 395                 400

Pro Gly Phe Ala Glu Trp Asn Gly Gln Phe Arg Asp Asp Ile Arg Lys
                405                 410                 415

Phe Trp Lys Gly Asp Ser Asn Met Arg Gly Ile Leu Ala Gly Arg Leu
            420                 425                 430

Gln Ala Ser Gly Glu Leu Phe Asp His Gln Arg Arg Lys Pro Trp Ala
        435                 440                 445

Ser Val Asn Phe Val Thr Ala His Asp Gly Phe Thr Leu Glu Asp Leu
    450                 455                 460

Val Ser Tyr Asn Asp Lys His Asn Asp Ala Asn Gly Glu Glu Asn Arg
465                 470                 475                 480

Asp Gly Gly Asn Asp Asn Glu Ser Tyr Asn His Gly Val Glu Gly Pro
                485                 490                 495

Ser Asp Asp Pro Ala Val Arg Ile Pro Arg Asp Arg Val Lys Arg Ala
            500                 505                 510

Met Leu Ala Thr Met Phe Phe Ser His Gly Thr Pro Met Leu Leu Gly
```

```
                515                 520                 525
Gly Asp Glu Phe Gly Arg Thr Gln Gln Gly Asn Asn Asn Ala Tyr Cys
    530                 535                 540

Gln Asp Asn Glu Leu Ser Trp Tyr Asp Trp Lys Leu Ala Thr Ser Glu
545                 550                 555                 560

Gln Gly Arg Glu Leu Thr Asp Phe Val Ala Arg Leu Ala Arg Leu Arg
                565                 570                 575

Glu Gln His Pro Thr Leu Arg Ala Ala His Phe Leu Arg Gly Asp Lys
            580                 585                 590

Glu Val Ala Pro Gly Met Arg Glu Val Ala Trp Phe Asp Glu Ser Gly
        595                 600                 605

Ala Glu Met Thr Gln Glu Thr Trp Gly Tyr Thr Glu Gly Arg Leu Leu
    610                 615                 620

Ala Leu Arg Arg Ala Gln Ala Tyr Gly Glu Lys Arg Ala Asp Val Thr
625                 630                 635                 640

Leu Val Leu Ile Asn Ala Thr Pro Glu Thr His Val Phe His Leu Pro
                645                 650                 655

Ala Pro Ala Val Asn Trp Arg Met Arg Cys Asn Ser Ala Val Pro Asp
            660                 665                 670

Ala Thr Glu Val Ala Trp Thr Asp Ser Thr Ile Ala Val Glu Gly Arg
        675                 680                 685

Ser Val Ile Leu Leu Gly Ser Ile Val Arg Thr Glu Pro Ala
    690                 695                 700

<210> SEQ ID NO 3
<211> LENGTH: 585
<212> TYPE: DNA
<213> ORGANISM: Escherichia coli

<400> SEQUENCE: 3
gtgaagcgcg ccatgctggc gacgatgttc ttctcgcacg gcacgcccat gctactgggg     60
ggcgacgagt tcggccgtac gcaacagggc aacaacaatg cctattgcca ggacaacgaa    120
ttgtcatggt acgactggaa gctcgccacg tcggagcagg gcagggagct gaccgacttc    180
gtggcgcggc tggcacggtt gcgcgaacag caccccacgt tgcgcgccgc gcatttcctg    240
cgtggcgata aggaggtcgc gccgggtatg cgcgaggtgg catggttcga cgagagtggc    300
gcggagatga cccaggaaac ctggggttat acagaggggc gcctgcttgc cctgcgtcgc    360
gcccaggcgt acggcgagaa gcgcgccgac gtgaccctcg tgctgatcaa cgcgacgccc    420
gagacccatg tgttccatct gccggcaccc gcggtcaact ggcggatgcg ctgcaacagt    480
gcggtgcctg acgcaaccga ggtcgcatgg accgattcga cctttgcggt cgaagggcgc    540
agcgtgatcc tgctcggctc gattgtccgg accgaaccgg catga                   585

<210> SEQ ID NO 4
<211> LENGTH: 194
<212> TYPE: PRT
<213> ORGANISM: Escherichia coli

<400> SEQUENCE: 4

Val Lys Arg Ala Met Leu Ala Thr Met Phe Phe Ser His Gly Thr Pro
1               5                   10                  15

Met Leu Leu Gly Gly Asp Glu Phe Gly Arg Thr Gln Gln Gly Asn Asn
            20                  25                  30

Asn Ala Tyr Cys Gln Asp Asn Glu Leu Ser Trp Tyr Asp Trp Lys Leu
        35                  40                  45
```

```
Ala Thr Ser Glu Gln Gly Arg Glu Leu Thr Asp Phe Val Ala Arg Leu
 50                  55                  60
Ala Arg Leu Arg Glu Gln His Pro Thr Leu Arg Ala Ala His Phe Leu
 65                  70                  75                  80
Arg Gly Asp Lys Glu Val Ala Pro Gly Met Arg Glu Val Ala Trp Phe
                 85                  90                  95
Asp Glu Ser Gly Ala Glu Met Thr Gln Glu Thr Trp Gly Tyr Thr Glu
                100                 105                 110
Gly Arg Leu Leu Ala Leu Arg Arg Ala Gln Ala Tyr Gly Glu Lys Arg
                115                 120                 125
Ala Asp Val Thr Leu Val Leu Ile Asn Ala Thr Pro Glu Thr His Val
    130                 135                 140
Phe His Leu Pro Ala Pro Ala Val Asn Trp Arg Met Arg Cys Asn Ser
145                 150                 155                 160
Ala Val Pro Asp Ala Thr Glu Val Ala Trp Thr Asp Ser Thr Phe Ala
                165                 170                 175
Val Glu Gly Arg Ser Val Ile Leu Leu Gly Ser Ile Val Arg Thr Glu
                180                 185                 190
Pro Ala
```

<210> SEQ ID NO 5
<211> LENGTH: 274
<212> TYPE: DNA
<213> ORGANISM: Burkholderia glumae

<400> SEQUENCE: 5

```
cgctcggcac cccgatgctg ctcggcggcg acgagttcgg ccgcagccag cagggcaaca      60
acaatgccta ttgccaggac accgagctcg cgtggttcga ctgggaggcc gccgccagcg     120
acgccgggcg ccggctcacc ggcttcgtcg cgcggctcgc cgcgctgcgc cgcgagcacc     180
cgctgctgtc ggggccgggc tatccgtcgg cgaccgcgga ggccgcgccg gggctgcgcg     240
agatcgactg gttcgacgag cgcggcgagg cgat                                  274
```

<210> SEQ ID NO 6
<211> LENGTH: 3076
<212> TYPE: DNA
<213> ORGANISM: Escherichia coli

<400> SEQUENCE: 6

```
tttcctgcgt aaccagggcg atgcctggcg ctggacgctg gacttcctgc gccgcagcta      60
cgacgagtac agccactcca acgatgacga gcgccgtgcg gaaatcgaag gtggctacga     120
tgcgttcgcc gccgcggtgg gtacgcgtct gggcgagctg catgcgctgt tggcgaagcc     180
gtcggagttt ccggcgttcg atccggaagc ggccacggcg ccgtggcgc atgcctggcg     240
cgacagcgtt cgtgagcagg tgaagcgcgc ggcgggttcg ctcgatcgtg cgacggaggt     300
atccgaaagc gtccaccgtg atatcgaggc ggtgcacgga ctcatcggcg cgctggacaa     360
gcgcatcggg gagctgtcga aggcgggcga gggtgcgttg ctcacccgca cccatggcga     420
tttccatctg gtcagatcc tcgtggtcca ggacgatgcc tacatcatcg atttcgaagg     480
cgagcctgcc cgctcgctgg aagaacgccg tggcaagcac acgccactgc gcgacgtcgc     540
cggcttcctg cgctcactgc attacgcggc cgccatggcc cgccgtggtg aagacggcct     600
ggcaccggtg gaagacgagg gcttcggtca gtacctggcc cgattccgcg cgcgctcgtc     660
gcgggttttc ctggaagcct accggctgt actggatgcg cgcccgtgc gctgggtcaa     720
```

```
tgcaggcgac ctcgtgccgc tgctcgaact tttcatcatc gaaaaggcgg cctacgaggt      780
cagctacgaa gcggcgaatc ggcccggctg gctcgacgtg ccactgcgtg gcctgctcga      840
tgccgcccgc ggcgataccg ctaccgaact gaaggagggt acgtgactga cgcacgtagc      900 tacgactga gcgacgccgc cgcggtggcc gcgctggtgg agggccgcca cggcgacccc       960
ttcgccctgc tgggaccgca cacggtcgac gggcggcgtg tcgtgcgcac cttgcaaccc     1020
ggtgcgctcg gtgtcgaact gatcgacgcg gcaggcaagc cggtcgcgga actgcggcgc     1080
gtccacgacg gaggtctttt cgccgggtgc gctcccgacg gctccgggta ccggctgcgc     1140
gttcgctggt ccggggcaag ccatgacacg cacgatcctt acagcttcgg caccctgttg     1200
gccgacgacg atctcgcacg gatggccgag gggacgcatg tcgaactgtt ccgcgtcctc     1260
ggtgcgcatc ccatcaccat cgatggcgtg cacggcgtac gcttcgctgt ctgggcaccg     1320
aacgcgcagc gggtaagcgc ggtcggcgac ttcgacagct gggacggacg ccgtcacccg     1380
atgcgaaaac gcgtgccctc gggcgtgtgg gaactgttcg ttcccggcct gctcgccggc     1440
gcacgctata aatacgagat ctggggagct gatgggtcgc tcacgcaacg tgccgatccg     1500
gtcgcgctgg ccgcggaact gccgccggcc acgggatcca tcgtggccga cccgaccgcc     1560
ttccactgga cggacgggga gtggctgcgc aagcgtggcg cgctccacca cgccgggtcg     1620
ccgttgtcga tctacgaact gcacgccggc tcctggctgc gaggcaagga taacgaagag     1680
ctgcactggg acgacatcgg cgaacggctg attccctacg tcgcggggat gggcttcacg     1740
cacatcgaac tgctgccgat ttcagagcac ccgttcggtg gttcgtgggg gtaccagccc     1800
ctgggccagt tcgccccgac atcgcgtttc ggtacgcccg aagccttcgc ccggttcgtg     1860
gaccgctgcc atgaagccgg cgttggcgtg atcgtcgact gggtgcctgc gcatttcccc     1920
accgatatcc acggcctggc gcacttcgac ggtacgccgt tgtacgagca cgcggacccg     1980
cgcgaaggtt tccatcagga ctggaacacc ctgatcttca acctcggtcg caacgaggta     2040
tcgggcttcc ttgtcgcgag cgcgctggcc tggcttgaac gtttccatgt cgacgggctt     2100
cgtgtcgatg cggtcgcgtc gatgctctat cgcgactaca gccgcaagca tggcgagtgg     2160
gtaccgaaca agtacggtgg ccgcgagaac ctcgaatcga tcgacttcct gcgccgggtg     2220
aaccagctcg ttgccgaacg ccatcccgat tgcatgacca ttgccgagga atccacggcg     2280
tggccgggcg taacccagcc ggtggagcag ggtgggctcg gcttcacctt caagtggaac     2340
atgggctgga tgcacgattc gctcgacttc atgacgcacg atccgatcca tcgccgctgg     2400
caccacggcg agatgacctt cagcatggtt tatgcgtatt cggagaagtt cgtgcttccg     2460
ctgtcgcacg acgaagtggt gcacggcaag cgatccctcc tgggtcgcat gcctggcgac     2520
gagtggcaga aattcgccaa cctgcgtgcc tattacggct tcatgtgggg gcacccaggc     2580
aagaagctgc tgttcaccgg cggggagatc gcccagccgc gcgaatggaa tcacgacgcg     2640
cagattgcct ggagttgctc gatcatccgc tgcacctggc gtgcagaact ggtgcgtgac     2700
ctaaaccagc tctacgccgc cacccccggca ctccatgcct gggattcgga tccccgcggg    2760
tttcgctggg tcatcggcga cgatgccgag cagagtgtgt tcgcctggct gcgcatggcc     2820 gatgcggcc gcaccgttct ggtggtcagc aacatgacgc cgacacacgg catggcttcc      2880
gcatcggcgt gcccgaaggc ggccgttggc gtgaggcgct gaattccgac gcggtcgagt     2940
acggcggctc gggcatcggc aacgaaggtg aacgccatgc ccaggcggtg cctgcacaca     3000
gcttcgctca gtcgctcgta ctcagcttgc cgccgttgtc gacggtcatg ttcatagccg     3060
```
actgacgagg aaatcg                                                3076

<210> SEQ ID NO 7
<211> LENGTH: 1882
<212> TYPE: DNA
<213> ORGANISM: Escherichia coli

<400> SEQUENCE: 7
gcgcccgcta cgtgcatgcg atgccttacg gcgcgcgatc gctgggcgat ggcaccaccc     60
gtttccggct gtgggcacct gatctggaag cggtgtcgct cgagtgcgac accgggcaca    120
cggcgcccat gcggtcgctc gacgacggct ggttcgagtg catctgcccc gccgaggtgg    180
gcgtgggcta ccgcttccgg atcaacgcgt ccctggcggt gccggatccc cgtcgcggc     240
gccagcgcgg cggcgatgtg catggttata gcgtcgttac cgatcctctc gccttcgagt    300
ggcgcaatac ggcgtggaag ggaaggccct ggcgcgagtc ggtcatctac gagctccacg    360
tgggtgtgct cggcgggttt catggcgtcg aaatgatcct gccgcacctg gcgtcacttg    420
gcgtcacggc gatcgagctc atgccgatcg cgcagtttcc cggtgagcgt aactgggtt     480
acgatggcgt gcttccgtac gcaccggccg acgcttacgg ttcgccggaa gatctcaagg    540
ccatgatcga cacagcgcac gatctcggtc tgatggtctt cctcgatgtg gtctacaacc    600
atttcgggcc cgatgggaat taccttggtg cctatgcctc gcggtttttc gacgagggag    660
tgcacacgcc ctggggtgcc gcgatcgtg tctcatcgcc acaggtgggc gactactttg     720
ttcacaacgc gctctactgg atccaggaat ttcgcttcga cggcctgcgt ttcgacgctg    780
tccacgcgat cggtaatccc ggttggctgg cgtcgctggc cagccgcgtc cacgccgccg    840
tcggaccgga tcgccatgtg cacctgatcc tcgagaacga ggccaaccaa gccaacctgc    900
tcggtcgcg tcgcttcgac gcgcagtgga acgacgactt ccacaatgcg ctgcacgtac     960
tgctcacgga tgagggtgag ggttattacg ctcactacca ggcgccgatg acaagctac    1020
ttaggacgtt gcgcgaaggc tttgcctacc agggcgaact gatgggctcg cgtcgtcgtg   1080
gcgagccgag tggcacctg gcgccgtcgc gcttcgtgaa cttcctgcag aaccacgacc    1140
aggtcggcaa ccgggccttc ggcgagcgcc tgacgtcgct ggtcgatccc gcaacgatgg   1200
aagcggcgct ggcgctgctc ctgcttgctc ccttcgtgcc gatgctttc atgggcgagg     1260
aatgggcgag ccgcacgccg ttcctgtatt tcaccgactt cagcgatgac gaacttcgtg   1320
atgcggttcg tgacggtcgt cgtaaggaat ttgccgcgtt caccagcttc ggaggcgaag   1380
aaattcccga tccgaacgag tacagcacct tcaccgcgtc gattcccgag cgcgatatca   1440
cagagggcga gcatcggcgc ctctatatcc gcgacctggt cgcccttcgc cataaatacg   1500
tggcgcccta tatcgacgat gcacgtagcc tcggcgctga agctctcggt gagcgtgctt   1560
tcaaggcgtc gtggtcgctc ggcggtcagg tactgaccgt gttcgtcaac ctcggcaaca   1620
ccgacgtcac catcgtgcag ccaccatcgc cctcggcggc gtggctgcac ggcgacgccg   1680
ccgagattgc ctctgtatcg cgtggcctgc ttcccgcacg ccgcaccgtt gcctgcctgg   1740
agtcctgagc cgtgaacgcc cccctcgacg atcgtctcgc cctgctagcg gaacaggccg   1800
gcgtgtacgt gtattggcgc gacgcgctgg atcgtccgca gtccacgccc gccgacacgt   1860
tacgcgccgt cctgcgggcc ct                                           1882

<210> SEQ ID NO 8
<211> LENGTH: 33
<212> TYPE: DNA
<213> ORGANISM: Artificial Sequence

```
<220> FEATURE:
<223> OTHER INFORMATION: G3-1, upstream clone

<400> SEQUENCE: 8
agctgcgatc gccacgaggg tgaagcgcgc cat                              33

<210> SEQ ID NO 9
<211> LENGTH: 33
<212> TYPE: DNA
<213> ORGANISM: Artificial Sequence
<220> FEATURE:
<223> OTHER INFORMATION: G3-2, downstream clone

<400> SEQUENCE: 9
gtgcgtttaa actgccggtt cggtccggac aat                              33

<210> SEQ ID NO 10
<211> LENGTH: 29
<212> TYPE: DNA
<213> ORGANISM: Artificial Sequence
<220> FEATURE:
<223> OTHER INFORMATION: G3-3, 161 internal

<400> SEQUENCE: 10
ggagctgacc gacttcgtgg cgcggctgg                                   29

<210> SEQ ID NO 11
<211> LENGTH: 29
<212> TYPE: DNA
<213> ORGANISM: Artificial Sequence
<220> FEATURE:
<223> OTHER INFORMATION: G3-4, 161-reverse

<400> SEQUENCE: 11
ccagccgcgc cacgaagtcg gtgagctcc                                   29

<210> SEQ ID NO 12
<211> LENGTH: 25
<212> TYPE: DNA
<213> ORGANISM: Artificial Sequence
<220> FEATURE:
<223> OTHER INFORMATION: 281 internal

<400> SEQUENCE: 12
aggtggcatg gttcgacgag agtgg                                       25

<210> SEQ ID NO 13
<211> LENGTH: 25
<212> TYPE: DNA
<213> ORGANISM: Artificial Sequence
<220> FEATURE:
<223> OTHER INFORMATION: G3-6, 281 reverse

<400> SEQUENCE: 13
ccactctcgt cgaaccatgc cacct                                       25

<210> SEQ ID NO 14
<211> LENGTH: 27
<212> TYPE: DNA
<213> ORGANISM: Artificial Sequence
<220> FEATURE:
<223> OTHER INFORMATION: G7 upstream reverse

<400> SEQUENCE: 14
cgttggcgtc gttgtgtttg tcgttgt                                     27
```

```
<210> SEQ ID NO 15
<211> LENGTH: 29
<212> TYPE: DNA
<213> ORGANISM: Artificial Sequence
<220> FEATURE:
<223> OTHER INFORMATION: G8 upstream reverse

<400> SEQUENCE: 15
cttcgccgtt ggcgtcgttg tgtttgtcg                                          29

<210> SEQ ID NO 16
<211> LENGTH: 24
<212> TYPE: DNA
<213> ORGANISM: Artificial Sequence
<220> FEATURE:
<223> OTHER INFORMATION: G9 biotin internal southern probe

<400> SEQUENCE: 16
gcgacgcccg agacccatgt gttc                                               24

<210> SEQ ID NO 17
<211> LENGTH: 17
<212> TYPE: DNA
<213> ORGANISM: Artificial Sequence
<220> FEATURE:
<223> OTHER INFORMATION: Sac1.7p1F, primer for walk

<400> SEQUENCE: 17
gggcaatgtc gagatcg                                                       17

<210> SEQ ID NO 18
<211> LENGTH: 16
<212> TYPE: DNA
<213> ORGANISM: Artificial Sequence
<220> FEATURE:
<223> OTHER INFORMATION: Sac1.7p1R, primer for walk

<400> SEQUENCE: 18
ttctccaccg gcaggg                                                        16

<210> SEQ ID NO 19
<211> LENGTH: 22
<212> TYPE: DNA
<213> ORGANISM: Artificial Sequence
<220> FEATURE:
<223> OTHER INFORMATION: F-519, upstream forward primer

<400> SEQUENCE: 19
gatcaccagc ggcgaaagcc ct                                                 22

<210> SEQ ID NO 20
<211> LENGTH: 22
<212> TYPE: DNA
<213> ORGANISM: Artificial Sequence
<220> FEATURE:
<223> OTHER INFORMATION: R-519, upstream reverse complement of -519

<400> SEQUENCE: 20
agggctttcg ccgctggtga tc                                                 22

<210> SEQ ID NO 21
<211> LENGTH: 22
<212> TYPE: DNA
<213> ORGANISM: Artificial Sequence
<220> FEATURE:
<223> OTHER INFORMATION: F+718, downstream forward primer
```

<400> SEQUENCE: 21
gatcgcgcag tttcccggtg ag                                          22

<210> SEQ ID NO 22
<211> LENGTH: 22
<212> TYPE: DNA
<213> ORGANISM: Artificial Sequence
<220> FEATURE:
<223> OTHER INFORMATION: R+718, downstream reverse complement of 718

<400> SEQUENCE: 22
ctcaccggga aactgcgcga tc                                          22

<210> SEQ ID NO 23
<211> LENGTH: 25
<212> TYPE: DNA
<213> ORGANISM: Artificial Sequence
<220> FEATURE:
<223> OTHER INFORMATION: F+1205, downstream forward primer

<400> SEQUENCE: 23
cgacgacttc cacaatgcgc tgcac                                       25

<210> SEQ ID NO 24
<211> LENGTH: 25
<212> TYPE: DNA
<213> ORGANISM: Artificial Sequence
<220> FEATURE:
<223> OTHER INFORMATION: R+1205, downstream reverse primer

<400> SEQUENCE: 24
gtgcagcgca ttgtggaagt cgtcg                                       25

<210> SEQ ID NO 25
<211> LENGTH: 21
<212> TYPE: DNA
<213> ORGANISM: Artificial Sequence
<220> FEATURE:
<223> OTHER INFORMATION: Fminus474, upstream forward primer

<400> SEQUENCE: 25
gcgcacgacg gcttcacgct g                                           21

<210> SEQ ID NO 26
<211> LENGTH: 21
<212> TYPE: DNA
<213> ORGANISM: Artificial Sequence
<220> FEATURE:
<223> OTHER INFORMATION: Rminus474, upstream reverse primer

<400> SEQUENCE: 26
cagcgtgaag ccgtcgtgcg c                                           21

<210> SEQ ID NO 27
<211> LENGTH: 26
<212> TYPE: DNA
<213> ORGANISM: Artificial Sequence
<220> FEATURE:
<223> OTHER INFORMATION: cc148R, upstream reverse primer HLE

<400> SEQUENCE: 27
gctcgggcgc gaagaaggca agcgtg                                      26

<210> SEQ ID NO 28

```
<211> LENGTH: 25
<212> TYPE: DNA
<213> ORGANISM: Artificial Sequence
<220> FEATURE:
<223> OTHER INFORMATION: 2A1bF671, 2A1 from F993 middle of seq

<400> SEQUENCE: 28
ctgcgaggca aggataacga agagc                                           25

<210> SEQ ID NO 29
<211> LENGTH: 24
<212> TYPE: DNA
<213> ORGANISM: Artificial Sequence
<220> FEATURE:
<223> OTHER INFORMATION: 4A5bF600, 4A4 from R849 middle of seq forward

<400> SEQUENCE: 29
caagccatgc acgccgggat accg                                            24

<210> SEQ ID NO 30
<211> LENGTH: 29
<212> TYPE: DNA
<213> ORGANISM: Artificial Sequence
<220> FEATURE:
<223> OTHER INFORMATION: hle2up554, middle of cc148r seq upstream hle

<400> SEQUENCE: 30
catgttcata gccgactgac gaggaaatc                                       29

<210> SEQ ID NO 31
<211> LENGTH: 29
<212> TYPE: DNA
<213> ORGANISM: Artificial Sequence
<220> FEATURE:
<223> OTHER INFORMATION: R9LCP9FM3
<220> FEATURE:
<221> NAME/KEY: misc_feature
<222> LOCATION: (13)..(13)
<223> OTHER INFORMATION: y is c or t
<220> FEATURE:
<221> NAME/KEY: misc_feature
<222> LOCATION: (19)..(19)
<223> OTHER INFORMATION: k is g or t
<220> FEATURE:
<221> NAME/KEY: misc_feature
<222> LOCATION: (25)..(26)
<223> OTHER INFORMATION: y is c or t

<400> SEQUENCE: 31
atgggggaac aaygaactkc agtayyata                                       29

<210> SEQ ID NO 32
<211> LENGTH: 24
<212> TYPE: DNA
<213> ORGANISM: Artificial Sequence
<220> FEATURE:
<223> OTHER INFORMATION: R9LCP9MRCAL
<220> FEATURE:
<221> NAME/KEY: misc_feature
<222> LOCATION: (3)..(3)
<223> OTHER INFORMATION: m is a or c
<220> FEATURE:
<221> NAME/KEY: misc_feature
<222> LOCATION: (5)..(5)
<223> OTHER INFORMATION: k is g or t
<220> FEATURE:
<221> NAME/KEY: misc_feature
<222> LOCATION: (12)..(12)
<223> OTHER INFORMATION: r is a or g
<220> FEATURE:
<221> NAME/KEY: misc_feature
```

```
<222> LOCATION: (19)..(19)
<223> OTHER INFORMATION: r is a or g
<220> FEATURE:
<221> NAME/KEY: misc_feature
<222> LOCATION: (20)..(20)
<223> OTHER INFORMATION: m is a or c
<220> FEATURE:
<221> NAME/KEY: misc_feature
<222> LOCATION: (21)..(21)
<223> OTHER INFORMATION: r is a or g

<400> SEQUENCE: 32
aamckttggt trttggcgrm rtag                                           24

<210> SEQ ID NO 33
<211> LENGTH: 22
<212> TYPE: DNA
<213> ORGANISM: Artificial Sequence
<220> FEATURE:
<223> OTHER INFORMATION: R9seqF1

<400> SEQUENCE: 33
caggtgacgg gtggaaatct gg                                             22

<210> SEQ ID NO 34
<211> LENGTH: 22
<212> TYPE: DNA
<213> ORGANISM: Artificial Sequence
<220> FEATURE:
<223> OTHER INFORMATION: R9seqR1

<400> SEQUENCE: 34
ctgctgaatc ttcgctccgc tg                                             22

<210> SEQ ID NO 35
<211> LENGTH: 30
<212> TYPE: DNA
<213> ORGANISM: Artificial Sequence
<220> FEATURE:
<223> OTHER INFORMATION: GOVVFM3
<220> FEATURE:
<221> NAME/KEY: misc_feature
<222> LOCATION: (18)..(18)
<223> OTHER INFORMATION: r is a or g
<220> FEATURE:
<221> NAME/KEY: misc_feature
<222> LOCATION: (27)..(27)
<223> OTHER INFORMATION: y is c or t

<400> SEQUENCE: 35
ggatggggaa acaatgarct gcagtaytat                                     30

<210> SEQ ID NO 36
<211> LENGTH: 27
<212> TYPE: DNA
<213> ORGANISM: Artificial Sequence
<220> FEATURE:
<223> OTHER INFORMATION: GOVVRM3
<220> FEATURE:
<221> NAME/KEY: misc_feature
<222> LOCATION: (4)..(4)
<223> OTHER INFORMATION: r is a or g
<220> FEATURE:
<221> NAME/KEY: misc_feature
<222> LOCATION: (7)..(7)
<223> OTHER INFORMATION: y is c or t
<220> FEATURE:
<221> NAME/KEY: misc_feature
<222> LOCATION: (13)..(13)
<223> OTHER INFORMATION: r is a or g
<220> FEATURE:
```

```
<221> NAME/KEY: misc_feature
<222> LOCATION: (19)..(19)
<223> OTHER INFORMATION: n is a, c, g, or t
<220> FEATURE:
<221> NAME/KEY: misc_feature
<222> LOCATION: (21)..(22)
<223> OTHER INFORMATION: r is a or g

<400> SEQUENCE: 36
ccarttyccg ccraccgcna rrttcag                                              27

<210> SEQ ID NO 37
<211> LENGTH: 27
<212> TYPE: DNA
<213> ORGANISM: Artificial Sequence
<220> FEATURE:
<223> OTHER INFORMATION: C6D588F3

<400> SEQUENCE: 37
gagctggcta cacaatccgc gaacggt                                              27

<210> SEQ ID NO 38
<211> LENGTH: 30
<212> TYPE: DNA
<213> ORGANISM: Artificial Sequence
<220> FEATURE:
<223> OTHER INFORMATION: C6D588R6

<400> SEQUENCE: 38
cagaacgcct tgcggttgtt gattagcttg                                           30

<210> SEQ ID NO 39
<211> LENGTH: 25
<212> TYPE: DNA
<213> ORGANISM: Artificial Sequence
<220> FEATURE:
<223> OTHER INFORMATION: S3AYW2F2

<400> SEQUENCE: 39
ggagtcctgg agcgtgtgac gatgc                                                25

<210> SEQ ID NO 40
<211> LENGTH: 25
<212> TYPE: DNA
<213> ORGANISM: Artificial Sequence
<220> FEATURE:
<223> OTHER INFORMATION: S3AYW2R2A

<400> SEQUENCE: 40
aatgccgaaa ggcgctcgca aagct                                                25

<210> SEQ ID NO 41
<211> LENGTH: 28
<212> TYPE: DNA
<213> ORGANISM: Artificial Sequence
<220> FEATURE:
<223> OTHER INFORMATION: E0IAJ1F1

<400> SEQUENCE: 41
ctcacccgaa gaacgccagc tgatgaac                                             28

<210> SEQ ID NO 42
<211> LENGTH: 25
<212> TYPE: DNA
<213> ORGANISM: Artificial Sequence
<220> FEATURE:
<223> OTHER INFORMATION: E0IAJ1R2
```

```
<400> SEQUENCE: 42
gtgtacgtaa tgcgggggaa cgaac                                          25

<210> SEQ ID NO 43
<211> LENGTH: 27
<212> TYPE: DNA
<213> ORGANISM: Artificial Sequence
<220> FEATURE:
<223> OTHER INFORMATION: T2LU54F1

<400> SEQUENCE: 43
ttgaggtagc cagcccggaa gagatca                                        27

<210> SEQ ID NO 44
<211> LENGTH: 25
<212> TYPE: DNA
<213> ORGANISM: Artificial Sequence
<220> FEATURE:
<223> OTHER INFORMATION: T2LU54R2A

<400> SEQUENCE: 44
gtgtacgtaa tgcgggggaa cgaac                                          25

<210> SEQ ID NO 45
<211> LENGTH: 24
<212> TYPE: DNA
<213> ORGANISM: Artificial Sequence
<220> FEATURE:
<223> OTHER INFORMATION: XLEfor1

<400> SEQUENCE: 45
gcaaagtcat ggatgtggtc gatg                                           24

<210> SEQ ID NO 46
<211> LENGTH: 25
<212> TYPE: DNA
<213> ORGANISM: Artificial Sequence
<220> FEATURE:
<223> OTHER INFORMATION: XLErev2

<400> SEQUENCE: 46
taatatccgc ctccgacatc cacgg                                          25

<210> SEQ ID NO 47
<211> LENGTH: 22
<212> TYPE: DNA
<213> ORGANISM: Artificial Sequence
<220> FEATURE:
<223> OTHER INFORMATION: INR9revF1

<400> SEQUENCE: 47
ccagatttcc acccgtcacc tg                                             22

<210> SEQ ID NO 48
<211> LENGTH: 22
<212> TYPE: DNA
<213> ORGANISM: Artificial Sequence
<220> FEATURE:
<223> OTHER INFORMATION: INR9revR1

<400> SEQUENCE: 48
cagcggagcg aagattcagc ag                                             22

<210> SEQ ID NO 49
```

```
<211> LENGTH: 1239
<212> TYPE: DNA
<213> ORGANISM: Escherichia coli

<400> SEQUENCE: 49
atgcgaagaa aaggaaagat gctttgcctg atggtgctgt tcagtctttt gattgccatg      60
atgcctgcta acgtcacgaa tgcggctccg acctggaatt tggtatggag cgatgaattt     120
aacggaactt cttttggacaa gtccaattgg aaagcgaaa tcggaaccgg cagcggcggg     180
tggggcaaca acgagcttca gtattacacg gaccgcccgg agaatgtcca ggtgacgggt     240
ggaaatctgg tcattaccgc tcgcaaagaa gcctacggcg gatgaatta cacgtcggca     300 cggattaaaa cgcaagggct gcgcagcttt acgtacggaa agatcgaagc gcgtatcaag     360
ctgccgtcgg gacaaggatt atggccggct ttttggatgc tgggaacgaa catcgattcc     420
gtcggatggc ccaagagcgg agaaacggac attatggagc gggtcaacaa caatccttac     480
gtaaacggta ccgtgcactg ggatgccaat ggccaagccg attatgggca ggtatccgga     540
aatcttgatt ttacccaata tcatgtatat agcgttgaat gggattccaa gtatattaaa     600
tggttcgtcg acggccagca gtataacgca ttctacatcg aaaacggtac aggtaacacg     660
gaggaattcc aactgccgtt cttcctgctg ctgaatctgg cggtcggtgg caattggccg     720
ggtagcccga taattctac gcagttccct gcccaaatgc tggtcgatta cgtacgggta     780
tatcagagct ctgatgcgcc caatattgtg agcggcggca tttacacgat cgggaacaag     840
gccagcggca agtcatgga tgtggtcgat gtatcgacgg ccagcggagc gaagattcag     900
cagtggacca actacagcgc caataaccaa agattcaaga tcgaaagcac cggagacggc     960
ttctataagc tcacggccgt gcacagcggg aaggtactgg acgtgccgaa ttcttcgaca    1020
gcgaccggcg ttcagctgca gcaatgggac gacaacggga cgaatgcgca gcggtggagc    1080
accgtggatg tcggaggcgg atattacaaa ctggtatcca agtgagcgg actggtcgcc    1140 gactatcgg gatcttccag cgctgacggg gccgtggtcc agcagtggag cgacaacggt    1200
accgatgccc agaagtggtc gtttacgaaa gtgaattaa                          1239

<210> SEQ ID NO 50
<211> LENGTH: 412
<212> TYPE: PRT
<213> ORGANISM: Escherichia coli

<400> SEQUENCE: 50

Met Arg Arg Lys Gly Lys Met Leu Cys Leu Met Val Leu Phe Ser Leu
1               5                   10                  15

Leu Ile Ala Met Met Pro Ala Asn Val Thr Asn Ala Ala Pro Thr Trp
            20                  25                  30

Asn Leu Val Trp Ser Asp Glu Phe Asn Gly Thr Ser Leu Asp Lys Ser
        35                  40                  45

Asn Trp Lys Ala Glu Ile Gly Thr Gly Ser Gly Gly Trp Gly Asn Asn
    50                  55                  60

Glu Leu Gln Tyr Tyr Thr Asp Arg Pro Glu Asn Val Gln Val Thr Gly
65                  70                  75                  80

Gly Asn Leu Val Ile Thr Ala Arg Lys Glu Ala Tyr Gly Gly Met Asn
                85                  90                  95

Tyr Thr Ser Ala Arg Ile Lys Thr Gln Gly Leu Arg Ser Phe Thr Tyr
            100                 105                 110

Gly Lys Ile Glu Ala Arg Ile Lys Leu Pro Ser Gly Gln Gly Leu Trp
        115                 120                 125
```

-continued

```
Pro Ala Phe Trp Met Leu Gly Thr Asn Ile Asp Ser Val Gly Trp Pro
            130                 135                 140

Lys Ser Gly Glu Thr Asp Ile Met Glu Arg Val Asn Asn Asn Pro Tyr
145                 150                 155                 160

Val Asn Gly Thr Val His Trp Asp Ala Asn Gly Gln Ala Asp Tyr Gly
                165                 170                 175

Gln Val Ser Gly Asn Leu Asp Phe Thr Gln Tyr His Val Tyr Ser Val
                180                 185                 190

Glu Trp Asp Ser Lys Tyr Ile Lys Trp Phe Val Asp Gly Gln Gln Tyr
            195                 200                 205

Asn Ala Phe Tyr Ile Glu Asn Gly Thr Gly Asn Thr Glu Glu Phe Gln
            210                 215                 220

Leu Pro Phe Phe Leu Leu Leu Asn Leu Ala Val Gly Gly Asn Trp Pro
225                 230                 235                 240

Gly Ser Pro Asn Asn Ser Thr Gln Phe Pro Ala Gln Met Leu Val Asp
                245                 250                 255

Tyr Val Arg Val Tyr Gln Ser Ser Asp Ala Pro Asn Ile Val Ser Gly
                260                 265                 270

Gly Ile Tyr Thr Ile Gly Asn Lys Ala Ser Gly Lys Val Met Asp Val
            275                 280                 285

Val Asp Val Ser Thr Ala Ser Gly Ala Lys Ile Gln Gln Trp Thr Asn
            290                 295                 300

Tyr Ser Ala Asn Asn Gln Arg Phe Lys Ile Glu Ser Thr Gly Asp Gly
305                 310                 315                 320

Phe Tyr Lys Leu Thr Ala Val His Ser Gly Lys Val Leu Asp Val Pro
                325                 330                 335

Asn Ser Ser Thr Ala Thr Gly Val Gln Leu Gln Gln Trp Asp Asp Asn
                340                 345                 350

Gly Thr Asn Ala Gln Arg Trp Ser Thr Val Asp Val Gly Gly Gly Tyr
            355                 360                 365

Tyr Lys Leu Val Ser Lys Val Ser Gly Leu Val Ala Asp Leu Ser Gly
            370                 375                 380

Ser Ser Ser Ala Asp Gly Ala Val Val Gln Gln Trp Ser Asp Asn Gly
385                 390                 395                 400

Thr Asp Ala Gln Lys Trp Ser Phe Thr Lys Val Asn
                405                 410
```